(12) United States Patent
Buturovic et al.

(10) Patent No.: US 7,747,547 B1
(45) Date of Patent: Jun. 29, 2010

(54) SYSTEMS AND METHODS FOR DIAGNOSING A BIOLOGICAL SPECIMEN USING PROBABILITIES

(75) Inventors: Ljubomir J. Buturovic, East Palo Alto, CA (US); Glenda G. Anderson, San Jose, CA (US)

(73) Assignee: Pathwork Diagnostics, Inc., Redwood City, CA (US)

( * ) Notice: Subject to any disclaimer, the term of this patent is extended or adjusted under 35 U.S.C. 154(b) by 0 days.

(21) Appl. No.: 12/378,165

(22) Filed: Feb. 10, 2009

Related U.S. Application Data

(63) Continuation of application No. 11/982,104, filed on Oct. 31, 2007, now abandoned.

(51) Int. Cl.
G06F 15/18 (2006.01)
C12Q 1/68 (2006.01)
(52) U.S. Cl. .................. 706/12; 435/6; 702/19
(58) Field of Classification Search .............. 706/12, 706/45, 20; 435/6; 702/19, 20, 188; 703/11
See application file for complete search history.

(56) References Cited

U.S. PATENT DOCUMENTS

| | | | |
|---|---|---|---|
| 6,327,581 B1 | 12/2001 | Platt | |
| 6,427,141 B1 | 7/2002 | Barnhill | |
| 6,658,395 B1 | 12/2003 | Barnhill | |
| 6,789,069 B1 | 9/2004 | Barnhill et al. | |
| 6,882,990 B1 | 4/2005 | Barnhill et al. | |
| 6,920,451 B2 | 7/2005 | Shaw | |
| 6,944,602 B2 | 9/2005 | Cristianini | |
| 6,996,549 B2 | 2/2006 | Zhang et al. | |
| 7,117,188 B2 | 10/2006 | Guyon et al. | |
| 7,299,213 B2 | 11/2007 | Cristianini | |
| 7,318,051 B2 | 1/2008 | Weston et al. | |
| 7,353,215 B2 | 4/2008 | Bartlett et al. | |

(Continued)

FOREIGN PATENT DOCUMENTS

WO  WO 2004/053630 A2  6/2004

OTHER PUBLICATIONS

Agresti, 1996, *An Introduction to Categorical Data Analysis*, John Wiley & Sons, pp. 103-144.

(Continued)

*Primary Examiner*—David R Vincent
(74) *Attorney, Agent, or Firm*—Jones Day

(57) ABSTRACT

Apparatus, systems and methods for determining, for each respective phenotypic characterization in a set of $\{T_1, \ldots, T_k\}$ characterizations, that a test specimen has the respective characterization are provided. A pairwise probability function $g_{pq}(X, W_{pq})$, for a phenotypic pair $(T_p, T_q)$ in $\{T_1, \ldots, T_k\}$ is learned using a training population. $W_{pq}$ is a set of parameters derived from Y for $(T_p, T_q)$ by substituting each $Y_i$ in Y into $g_{pq}(X, W_{pq})$, as X, where $Y_i$ is the set of cellular constituent abundance values from sample i in the training population exhibiting $T_p$ or $T_q$. The learning step is repeated for each $(T_p, T_q)$ in $\{T_1 \ldots, T_k\}$, thereby deriving pairwise probability functions $G=\{g_{1,2}(X, W_{1,2}), \ldots, g_{k-1,k}(X, W_{k-1,k})\}$. Pairwise probability values $P=\{p_{1,2}, \ldots, p_{k-1,k}\}$ are computed, where each $p_{pq}$ is equal to $g_{pq}(Z, W_{pq})$ in G, the probability that the test specimen has $T_p$ and not $T_q$, where Z is cellular constituent abundance values of the test specimen.

25 Claims, 3 Drawing Sheets

U.S. PATENT DOCUMENTS

| | | | |
|---|---|---|---|
| 7,366,719 | B2 | 4/2008 | Shaw |
| 7,383,237 | B2 | 6/2008 | Zhang et al. |
| 7,512,497 | B2 * | 3/2009 | Periwal ............... 702/19 |
| 2003/0182066 | A1 | 9/2003 | Konishi |
| 2004/0111453 | A1 | 1/2004 | Harris et al. |
| 2006/0265138 | A1 | 11/2006 | Bowtell et al. |
| 2007/0166707 | A1 * | 7/2007 | Schadt et al. ........... 435/6 |
| 2007/0269804 | A1 * | 11/2007 | Liew et al. ............. 435/6 |
| 2008/0294403 | A1 * | 11/2008 | Zhu et al. .............. 703/11 |

OTHER PUBLICATIONS

Ben-Dor et al., 2000, "Tissue Classification with Gene Expression Profiles," Journal of Computational Biology 7, 559-583.

Draghici, 2003, *Data Analysis Tools for DNA Microarrays*, Chapman & Hall/CRC Mathematical Biology and Medicine Series, pp. 246-307.

Duda et al., 2001, *Pattern Classification*, John Wiley & Sons pp. 395-409, 282-349, and 537-563.

Duda et al., 1973, *Pattern Classification and Scene Analysis*, John Wiley & Sons, Inc. pp. 211-256.

Furey et al., 2000, "Support vector machine classification and validation of cancer tissue samples using microarray expression data," Bioinformatics 16, 906-914.

Hastie et al., 2001, *The Elements of Statistical Learning Data Mining, Inference, and Prediction*, Springer Series, Chapters 6, 9, 10, 11, 12 and 13.

Hinton et al., Jul. 28, 2006, "Reducing the Dimensionality of Data with Neural Networks," Science 313, 504-507.

Hinton et al., 1995, "The 'Wake-Sleep' Algorithm for Unsupervised Neural Networks," Science 268, 1158-1161.

Hsu et al., 2007, "A Practical Guide to Support Vector Classification," Department of Computer Science, National Taiwan University, pp. 1-14.

Huang et al., Jan. 1, 2006, "Generalized Bradley-Terry Models and Multi-class Probability Estimates," Journal of Machine Learning Research 7, 85-115.

Lin et al., 2003, "A Note on Platt's Probabilistic Outputs for Support Vector Machines," Technical Report, Department of Computer Science and Information Engineering, pp. 1-8.

Mjolsness et al., 2001, "Machine Learning for Science: State of the Art and Future Prospects," Science 293, 2051-2055.

Platt, 1999, "Probabilistic Outputs for Support Vector Machines and Comparisons to Regularized Likelihood Methods," MIT Press, pp. 1-11.

Ramaswamy et al., 2001, "Multiclass cancer diagnosis using tumor gene expression signatures," Proceedings National Academy of Sciences USA 98, 15149-15154.

Wang et al., 2007, "Accurate Cancer Classification Using Expressions of Very Few Genes," IEEE/ACM Transactions on Computational Biology and Bioinformatics 4, 40-53.

Wu et al., 2004, "Probability Estimates for Multi-class Classification by Pairwise Coupling," Journal of Machine Learning Research 5, 975-1005.

\* cited by examiner

Pathwork TOO  
Clinical Validation

Pathwork Tissue of Origin Test

Sample ID: J06_0317P2A  Date/Time Processed: 19Mar2007 22:57PDT  PathWork Accession: 11568  
Microarray Type: PathChip  Version: TOO v21.2  Source Filename: J06_0317P2Acel

| TISSUE OF ORIGIN | SIMILARITY SCORE |
|---|---|
| Thyroid | 91.3 |
| Breast | 3.4 |
| Ovarian | 2.3 |
| Kidney | 1.0 |
| Non-small Cell Lung | 0.4 |
| Pancreas | 0.3 |
| Colorectal | 0.3 |
| Germ Cell | 0.2 |
| Non-Hodgkin's Lymphoma | 0.2 |
| Soft Tissue Sarcoma | 0.2 |
| Bladder | 0.1 |
| Hepatocellular | 0.1 |
| Prostate | 0.1 |
| Gastric | 0.1 |
| Melanoma | 0.1 |

The performance characteristics of this system have not been established. Not for use in diagnostic procedures.

SYSTEMS AND METHODS FOR DIAGNOSING A BIOLOGICAL SPECIMEN USING PROBABILITIES

CROSS REFERENCE TO RELATED APPLICATIONS

This application is a continuation of application Ser. No. 11/982,104, filed on Oct. 31, 2007 now abandoned which is hereby incorporated by reference herein in its entirety.

1 FIELD OF THE INVENTION

The field of this invention relates to computer systems and methods for determining a phenotypic characterization of a specimen from among a plurality of phenotypic characterizations.

2 BACKGROUND OF THE INVENTION

The phenotypic characterization of a specimen is a tool that has wide ranging diagnostic applications. For instance, phenotypic characterization of a specimen is needed for tumors in which a tumor's origin cannot be readily identified. These types of tumors are frustrating for pathologists, who are unable to provide a definitive diagnosis, and to oncologists, who thus lack information needed to begin standard-of-care, tissue-directed therapy. Such uncertain results can also add to patient suffering and prevent the efficient use of healthcare resources.

The National Comprehensive Cancer Network's (NCCN) guidelines emphasize the significance of identifying the tissue of origin so that cancer-specific management recommendations can be followed. In a prospective clinical study, Abbruzzese et al. concluded that, for certain challenging cases, "the survival duration of patients in whom the primary tumor was diagnosed was superior to that of patients in whom the primary tumor remained unknown." See, Abbruzzese et al., 1995, J Clin Oncol. 13: 2094-2103.

In some cases, a battery of tests is performed, yet still fails to definitively identify the primary tumor site. In some especially challenging cases, current pathological techniques, including immunohistochemistry (IHC) and imaging studies, such as x-rays and computed tomography (CT), identify the primary tumor site only 25 percent of the time. Hillen, 2000, Postgrad Med J. 76: 690-693. Clearly, there is a need for a more robust diagnostic solution. This is particularly important, given the availability of newer, more specific, and more effective therapeutic options that target cells of the primary tumor site.

There are a number of tools for determining a phenotypic characterization of a specimen from among a plurality of phenotypic characterizations. One example is immunohistochemistry (IHC), which is a type of assay in which specific antigens are visualized using fluorescent dye or enzyme markers. IHC studies can sometimes identify the primary tumor, even in poorly differentiated metastases. See, for example, Pavlidis et al., 2003, Eur J Cancer. 39: 1990-2005. However, currently available IHC markers do not address the full range of potential tumor types. Another example is cytogenetic methods, which assess chromosomal abnormalities to pinpoint the primary cancer tumor site. While cytogenic methods can provide insights in a number of specific situations, they generally are not in a comprehensive manner. Thus, in the case of cancer, cytogenetic methods are limited because only a few diagnostic chromosomal abnormalities have been identified to date. See, for example, Pavlidis et al., 2003, Eur J Cancer. 39: 1990-2005.

Yet another tool for determining a phenotypic characterization of a specimen from among a plurality of phenotypic characterizations is imaging. CT scans, mammography, magnetic resonance imaging (MRI) and fluorodeoxyglucose (FDG) positron emission tomography (PET) are representative examples of imaging. However, imaging has limitations. For example, in the case of cancer of unknown origin, these various imaging techniques can often be ineffective at determining the origin of the tissue. There are many reasons for the failure of imaging techniques to determine the site of origin of a tumor. These include very small tumor size and confounding structural abnormalities, as well as the limitations of each imaging modality.

Yet another tool for determining a phenotypic characterization of a specimen from among a plurality of phenotypic characterizations is microarray analysis. Although several groups have demonstrated the feasibility of using microarrays to classify uncertain tumors according to tissue of origin, (e.g., Su et al., 2001, Cancer Res. 61: 7388-7393; Ramaswamy, 2002, J Clin Oncol 20: 1932-1941; Giordano et al., 2001, Am J Pathol 159: 1231-1238; Bloom 2004, Am J Pathol 164: 9-16; Buckhaults et al., 2003, Cancer Res 63: 4144-4149; Tothill et al., 2005, Cancer Res 65: 4031-4040; and Ma et al. 2006, Arch Pathol Lab Med 130: 465-473) the application of these varied technologies in the clinical setting has proved a challenge due to the inherent complexity of accurately interrogating and interpreting expression signals from the thousands of distinctive genes that represent the dozen or more tissue types of highest interest. This is the fundamental informatics challenge involving any highly multiplex data. See, for example, Yeang et al., 2001, Bioinformatics 17: S316-S322. While microarrays are theoretically suited to this high degree of multiplexy, no test to date has demonstrated reliability in classifying large numbers of specimens involving the full range of potential tissue types.

The cost to determine a phenotypic characterization of a specimen from among a plurality of phenotypic characterizations can be significant, given that traditional approaches involve multiple technologies that are often run in parallel. For example, in the case of cancer, one study showed that, for certain challenging cases, the primary cancer site was found in only four (7.1 percent) of the 56 cases studied. The average cost of diagnosis was over seventeen thousand dollars. See Tong et al., Poster presented at annual meeting of American Society of Clinical Oncology; Jun. 2-6, 2006; Atlanta, Ga. Another study showed that, in Medicare patients, medical payments averaged $38,000 per patient per year. Tong et al. Poster presented at annual meeting of American Society of Clinical Oncology; Jun. 2-6, 2006; Atlanta, Ga. By rapidly identifying phenotypic characterization of a specimen from among a plurality of phenotypic characterizations, clinicians could potentially apply more appropriate therapies more quickly, potentially enabling improved patient outcomes and a better use of healthcare resources.

When a phenotypic characterization of a specimen from among a plurality of phenotypic characterizations has been made, physicians can provide far better, more focused therapeutic regimens. For instance, in the case of cancer, physicians increasingly have more tissue-specific treatment options. For example, 5-fluorouracil (5-FU)-based therapy was historically the treatment of choice for essentially all gastrointestinal adenocarcinoma tumors, whether they were colonic, pancreatic, or gastroesophageal in origin. However, each of these entities might be treated now with a more individualized approach (e.g., 5-FU/leucovorin with irinotecan or oxaliplatin for colonic, gemcitabine for pancreatic, and perhaps epirubicin, cisplatin, and 5-FU or a taxane for gastroesophageal primaries).

A prevalent problem in the art is the identification of which tissue originated a particular cancer. This is particularly a problem in instances where the cancer is not discovered before it has spread to multiple locations in the body. Of concern in such instances is determining which of the tissues the cancer originated, because such determination will affect the treatment regimen that is prescribed and will improve clinical outcome. For example, if the cancer originated in the bladder, a treatment regimen optimized to treat bladder cancer will be followed, whereas if the cancer originated in the breast, a treatment regimen optimized for breast cancer will be followed.

Identifying the tissue of origin of a poorly-differentiated or undifferentiated tumor at initial presentation can be challenging. Oncology treatment decisions are largely based on the tissue of origin, which makes proper identification vital to selection of the appropriate diagnostic and therapeutic cascades. The National Comprehensive Cancer Network (NCCN) Practice Guidelines recommend that, whenever possible, the tissue of origin should be identified so that the patient may be treated per the NCCN disease-specific guideline. Current diagnostic procedures include a physical examination and full medical history of the patient, laboratory and radiological evaluation, and pathologic assessment. Methods used to characterize a poorly-differentiated or undifferentiated tumor specimen include histologic, immunohistochemical and, when appropriate, electron microscopic evaluations. However, these techniques are limited in their ability to assess the tissue of origin for many poorly-differentiated or undifferentiated tumors. Improved methods are needed to obtain a more definitive diagnosis.

Given the above-background, what are needed in the art are improved systems and methods for phenotypic characterization of a specimen from among a plurality of phenotypic characterizations.

Discussion or citation of a reference herein will not be construed as an admission that such reference is prior art to the present invention.

3 SUMMARY OF THE INVENTION

The present invention addresses the shortcomings in the prior art. In the present invention, systems and methods for determining a phenotypic characterization of a test biological specimen from among a plurality of phenotypic characterizations are provided. Advantageously, for each respective pair (p, q) of phenotypic characterizations formed from the plurality of phenotypic characterizations, a pairwise probability that the test biological specimen has phenotypic characterization $T_p$ are computed, thereby forming several pairwise probabilities. The pairwise probabilities are useful for determining not only the most probable phenotypic characterization for the test biological specimen, but also whether the most probable phenotypic characterization is the clear choice over other phenotypic characterization pairs. Optionally, the pairwise probabilities can be computed as a set of probabilities, where each probability $p_i$ in the set of probabilities is a probability for a phenotypic characterization in the plurality of phenotypic characterizations such that $$\sum_{i=1}^{k} p_i = \text{is equal to a predetermined constant.}$$

In some embodiments, the predetermined constant is 1, 100, or some other number. The $p_i$ are useful for determining not only the most probable phenotypic characterization for the test biological specimen, but also whether the most probable phenotypic characterization is the clear choice over other phenotypic characterizations.

One aspect of the present invention provides a method of determining, for each respective phenotypic characterization in a set of $\{T_1, \ldots, T_k\}$ phenotypic characterizations, a probability that a test biological specimen has the respective phenotypic characterization. The method comprising a learning step in which a pairwise probability function $g_{pq}(X, W_{pq})$ is learned for a pair of phenotypic characterizations $(T_p, T_q)$ in the set of $\{T_1, \ldots, T_k\}$ phenotypic characterizations using a training population, wherein (i) there are at least five training samples in the training population for each phenotypic characterization in the set of $\{T_1, \ldots, T_k\}$ phenotypic characterizations; (ii) Y is the set of all training samples in the training population that exhibits either phenotypic characterization $T_p$ or phenotypic characterization $T_q$, and each $Y_i$ in Y is the set of $\{y_{i1}, \ldots, y_{in}\}$ cellular constituent abundance values for a plurality of cellular constituents measured from a sample i, from the training population, which exhibits either phenotypic characterization $T_p$ or phenotypic characterization $T_q$; (iii) $W_{pq}$ is a set of parameters derived from Y in the learning step for a pair of phenotypic characterizations $(T_p, T_q)$ by substituting each $Y_i$ into $g_{pq}(X, W_{pq})$, as X, during the learning step; (iv) k is 3 or greater; (v) n is at least 1; and (vi) p is not equal to q. The learning step is can be repeated for a different pair of phenotypic characterizations $(T_p, T_q)$ for all unique pairs of phenotypic characterizations in the set of $\{T_1 \ldots, T_k\}$ phenotypic characterizations, thereby deriving a plurality of pairwise probability functions $G=\{g_{1,2}(X, W_{1,2}), \ldots, g_{k-1, k}(X, _{k-1, k})\}$. One of skill in the art will recognize that different instances of the learning step can be executed simultaneously for different pairs of phenotypic characterizations $(T_p, T_q)$. Such concurrent learning is considered herein to be a "repeat" of the learning step even f such concurrent learning is performed contemporaneously. Once the plurality of pairwise probability functions $G=\{g_{1,2}(X, W_{1,2}), \ldots, g_{k-1,k}(X, W_{k-1, k})\}$ have been learned, a plurality of pairwise probability values $P=\{p_{1,2}, \ldots, p_{k-1, k}\}$ is computed, where each pairwise probability value $p_{pq}$ in P is equal to $g_{pq}(Z, W_{pq})$ in G, the probability that the test biological specimen has phenotypic characterization $T_p$ and does not have phenotypic characterization $T_q$, where Z is a set of $\{z_1, \ldots, z_n\}$ cellular constituent abundance values measured from the test biological specimen for the plurality of cellular constituents. Optionally, P is converted to a set M of k probabilities, where $M=\{p_1, p_2, \ldots, p_k\}$, and where each probability $p_j$ in M is a probability for a phenotypic characterization in the set of $\{T_1, \ldots, T_k\}$ phenotypic characterizations that the biological specimen has the phenotypic characterization such that $$\sum_{j=1}^{k} p_j$$

is equal to a predetermined constant.

Optionally, one or more pairwise probabilities $p_{pq}$ in P are outputted to a user interface device, a monitor, a computer readable storage medium, or a local or remote computer system when P is not converted to M. Optionally, one or more pairwise probabilities $p_{pq}$ in P are displayed when P is not converted to M. Optionally, one or more $p_j$ in M and/or one or more pairwise probabilities $p_{pq}$ in P are outputted a user interface device, a monitor, a computer readable storage medium, or a local or remote computer system when P is converted to M. Optionally one or more $p_j$ in M and/or one or more pairwise probabilities $p_{pq}$ in P are displayed when P is converted to M.

In some embodiments, for each respective phenotypic characterization in the set $\{T_1, \ldots, T_k\}$ of phenotypic characterizations, the training population comprises at least two, at least three, at least four, at least five, at least six, at least six, at least seven, at least eight, at least nine, at least ten, at least fifteen, or at least twenty samples that have the respective phenotypic characterization. In some embodiments, the set $\{T_1, \ldots, T_k\}$ of phenotypic characterizations is between 2 and 100 phenotypic characterizations, between 10 and 50 phenotypic characterizations, fifteen phenotypic characterizations, between 5 and 20 phenotypic characterizations, two phenotypic characterizations, more than two phenotypic characterizations, or more than fifteen phenotypic characterizations.

In some embodiments $$g_{pq}(Z, W_{pq}) = \sum_{R_i \in p} w'_i s(Z, R_i) - \sum_{R_j \in q} w''_j s(Z, R_j) + b$$

where, $R_i = \{r_{i1}, \ldots, r_{in}\}$ is the set of n cellular constituent abundance values for the plurality of cellular constituents measured from a sample i, from the training population, wherein sample i has phenotypic characterization $T_p$;

$R_j = \{r_{j1}, \ldots, r_{jn}\}$ is the set of n cellular constituent abundance values for the plurality of cellular constituents measured from a sample j, from the training population, wherein sample j has phenotypic characterization $T_q$;

$s(Z, R_i)$ is a score of a kernel function whose input is $(Z, R_i)$ where, for each respective cellular constituent abundance value $z_i$ in Z, the respective cellular constituent abundance value $z_i$ is matched to the corresponding cellular constituent abundance value $r_i$ in $R_i$;

$s(Z, R_j)$ is a score of a kernel function whose input is $(Z, R_j)$ where, for each respective cellular constituent abundance value $z_j$ in Z, the respective cellular constituent abundance value $z_j$ is matched to the corresponding cellular constituent abundance value $r_j$ in $R_j$;

b is a bias term;
$w'_i$ is a weight associated with $R_i$; and
$w''_j$ is a weight associated with $R_j$.

In some embodiments $s(Z, R_i)$ is equal to the value of the kernel function $e^{(-\gamma[(z_1-r_{i1})^2+(z_2-r_{i2})^2+\ldots(z_n-r_{in})^2])}$, where $z_1, \ldots, z_n$ are cellular constituent abundance values in Z that respectively correspond to cellular constituent abundance values $r_{i1}, \ldots, r_{in}$ in $R_i$ and where $s(Z, R_j)$ is equal to the value of the kernel function $e^{(-\gamma[(z_1-r_{j1})^2+(z_2-r_{j2})^2+\ldots(z_n-r_{jn})^2])}$, where $z_1, \ldots, z_n$ are cellular constituent abundance values in Z that respectively correspond to cellular constituent abundance values $r_{j1}, \ldots, r_{jn}$ in $R_j$. In some embodiments, the method further comprises determining values, for the given pair of phenotypic characterization $(T_p, T_q)$, for the set of weights $w'_i$s, $w''_j$, and b used in $g_{pq}(Z, W_{pq})$ before computing P by subjecting each set of cellular constituent abundance values in the training population that were measured from samples that have phenotypic characterization $T_p$ or $T_q$ to a support vector machine.

In some embodiments $$g_{pq}(Z, W_{pq}) = \frac{1}{1 + e^{Af(Z, W_{pq})+B}}$$

Where A and B are parameters derived from logistic regression of $s(Z, R_i)$ and the plurality of phenotypic characterizations.

In some embodiments, a phenotypic characterization in the plurality of phenotypic characterizations is an organ type, an abnormal state in an organ, a tissue type, an abnormal state in a tissue, a cell type, an abnormal cell type, a cell morphology, an abnormal cell morphology, a disease state, a disease prognosis, or a therapeutic response. In some embodiments, the set of cellular constituent abundance values Z for the plurality of cellular constituents measured from the test biological specimen or the set of cellular constituent abundance values $Y_i$ for the plurality of cellular constituents measured from the sample i from the training population are measured from a microarray comprising probes arranged with a density of 100 different probes per 1 $cm^2$ or higher, a density of at least 2,500 different probes per 1 $cm^2$, or a density of at least 5000 different probes per 1 $cm^2$.

In some embodiments, the set of cellular constituent abundance values Z for the plurality of cellular constituents measured from the test biological specimen or the set of cellular constituent abundance values $Y_i$ for the plurality of cellular constituents measured from the sample i from the training population are measured from a microarray comprising probes arranged with a density of at least 2,500 different probes per 1 $cm^2$. In some embodiments, the set of cellular constituent abundance values Z for the plurality of cellular constituents measured from the test biological specimen or the set of cellular constituent abundance values $Y_i$ for the plurality of cellular constituents measured from the sample i from the training population are measured from a microarray comprising at least 1,000 different probes, at least 5,000 different probes, at least 10,000 different probes, or at least 20,000 different probes.

In some embodiments, the set of cellular constituent abundance values Z for the plurality of cellular constituents measured from the test biological specimen or the set of cellular constituent abundance values $Y_i$ for the plurality of cellular constituents measured from the sample i from the training population are measured from an expression microarray, a comparative genomic hybridization microarray, an exon microarray, or a microRNA microarray. In some embodiments, the set of cellular constituent abundance values Z for the plurality of cellular constituents measured from the test biological specimen or the set of cellular constituent abundance values $Y_i$ for the plurality of cellular constituents measured from the sample i from the training population are measured from a microarray comprising between 10 and $5 \times 10^6$ oligonucleotides, between 50 and $9 \times 10^6$ oligonucleotides, or between 500 and 10,000 oligonucleotides. In some embodiments, the plurality of cellular constituents is between 5 mRNA and 50,000 mRNA, between 5 mRNA and 10,000 mRNA, between 100 mRNA and 20,000 mRNA, more than 10 mRNA, more than 40 mRNA, more than 50 mRNA, more than 200 mRNA, more than 1,000 mRNA, or between 1000 and 3000 mRNA. In some embodiments, the plurality of cellular constituents is between 50 proteins and 200,000 proteins, more than 100 proteins, or more than 200 proteins.

In some embodiments, for each respective phenotypic characterization in the plurality of phenotypic characterizations, the training population comprises at least three samples that have the respective phenotypic characterization. In some embodiments, each phenotypic characterization in the plurality of phenotypic characterizations is a cancer tissue of origin and wherein the plurality of phenotypic characterizations comprises bladder cancer, breast cancer, colorectal cancer, gastric cancer, germ cell cancer, kidney cancer, hepatocellular cancer, non-small cell lung cancer, non-Hodgkin's lymphoma, melanoma, ovarian cancer, pancreatic cancer, prostate cancer, soft tissue sarcoma, and thyroid cancer.

In some embodiments, the plurality of phenotypic characterizations is between 2 phenotypic characterizations and 100 phenotypic characterizations. In some embodiments, the set of cellular constituent abundance values Z are received from a remote source over a computer network and wherein the one or more pairwise probabilities $p_{pq}$ in P or the one or more $p_j$ in M are communicated to the remote source over said network. In some embodiments, the remote source is a remote computer or a remote computer system.

In some embodiments, the converting step comprises deeming the set of probabilities $\{p_1, p_2, \ldots, p_k\}$ that minimize the criterion $f(p_1, p_2, \ldots, p_k)$ over $p_i$, where $f(\ )$ is defined as $$f(p_1, p_2, \ldots, p_k) = \sum_{i=1}^{k} \sum_{j=1, j \neq i}^{k} \left( p_i P_{T_i, T_j}(Z, W_{ij}) - p_j P_{T_j, T_i}(Z, W_{ji}) \right)^2$$

subject to the constraints that $\Sigma^k_{i=1} p_i$=a predetermined constant and $p_i \geqq 0$.

In some embodiments, the pairwise probability function $g_{pq}(X, W_{pq})$ is learned using a pattern classification algorithm and/or statistical algorithm such as a decision tree, predictive analysis of microarrays, a multiple additive regression tree, a neural network, a clustering algorithm, principal component analysis, a nearest neighbor analysis, a linear discriminant analysis, a quadratic discriminant analysis, a support vector machine, an evolutionary method, a projection pursuit, a radial basis function, weighted voting, etc.

The present application is further directed to an apparatus that performs any of the above-identified methods or any of the methods disclosed herein. The application is further directed to a computer-readable medium storing a computer program executable by a computer to determine a phenotypic characterization of a test biological specimen from among a set of $\{T_1, \ldots, T_k\}$ phenotypic characterizations using a training population, the computer program comprising instructions for performing any of the above-identified methods or any of the methods disclosed herein.

In some embodiments, the samples in the training population are from multiple different labs so that they represent different measurement conditions. For instance, in some embodiments, there are samples in the training population that were measured in a first lab and other samples that were measured in a second lab. In some embodiments, there are samples in the training population from five or more labs, ten or more labs, twenty or more labs, or thirty or more labs.

In some embodiments, a phenotypic characterization in the plurality of phenotypic characterizations is a tissue type, an organ type, a cell type, a cell morphology, a disease state, an abnormal state in a tissue or organ, an abnormal cell type, or an abnormal cell morphology. In some embodiments, a phenotypic characterization is a disease prognosis such as (i) expected survival or (ii) expected time to recurrence. In some embodiments, a phenotypic characterization is a therapeutic response. As used herein, the terms "therapeutic response", "response to therapy", "response to treatment", and "clinical outcome" are used interchangeably.

In some embodiments, the plurality of cellular constituent abundance values Z measured from the test biological specimen are received from a remote source (e.g., a computer that is not the same computer where the above-identified computations are performed) over a computer network and one or more pairwise probability value in P or one or more probabilities $p_j$ in the set M of k probabilities are communicated to the remote source over the computer network. In some embodiments, the remote source is a remote computer connected to an Internet or other form of network.

Another aspect of the present invention provides an apparatus for determining, for each respective phenotypic characterization in a set of $\{T_1, \ldots, T_k\}$ phenotypic characterizations, a probability that a test biological specimen has the respective phenotypic characterization, the apparatus comprising a processor and a memory, coupled to the processor. The memory stores a module comprising:

(A) instructions for learning a pairwise probability function $g_{pq}(X, W_{pq})$ using a training population, for a pair of phenotypic characterizations $(T_p, T_q)$ in the set of $\{T_1, \ldots, T_k\}$ phenotypic characterizations, wherein:

(i) there are at least five training samples in the training population for each phenotypic characterization in the set of $\{T_1, \ldots, T_k\}$ phenotypic characterizations;

(ii) Y is the set of all training samples in the training population that exhibits either phenotypic characterization $T_p$ or phenotypic characterization $T_q$, and each $Y_i$ in Y is the set of $\{y_{i1}, \ldots, y_{in}\}$ cellular constituent abundance values for a plurality of cellular constituents measured from a sample i, from the training population, which exhibits either phenotypic characterization $T_p$ or phenotypic characterization $T_q$;

(iii) $W_{pq}$ is a set of parameters derived from Y by the instructions for learning (A) for a pair of phenotypic characterizations $(T_p, T_q)$ by substituting each $Y_i$ into $g_{pq}(X, W_{pq})$, as X, during said learning step (A);

(iv) k is 3 or greater;

(v) n is at least 1;

(vi) p is not equal to q, and (B) instructions for repeating the instructions for learning (A) for a different pair of phenotypic characterizations $(T_p, T_q)$, using the training population, for all unique pairs of phenotypic characterizations in the set of $\{T_1, \ldots, T_k\}$ phenotypic characterizations, thereby deriving a plurality of pairwise probability functions $G=\{g_{1,2}(X, W_{1,2}), \ldots, g_{k-1, k}(X, W_{k-1, k})\}$;

(C) instructions for computing a plurality of pairwise probability values $P=\{p_{1,2}, \ldots, p_{k-1, k}\}$, wherein each pairwise probability value $p_{pq}$ in P is equal to $g_{pq}(Z, W_{pq})$, the probability that the test biological specimen has phenotypic characterization $T_p$ and does not have phenotypic characterization $T_q$, wherein Z the set of $\{z_1, \ldots, z_n\}$ cellular constituent abundance values measured from the test biological specimen for the plurality of cellular constituents;

(D) optionally, instructions for converting P to a set M of k probabilities, wherein M={$p_1, p_2, \ldots, p_k$}, wherein each probability $p_j$ in M is a probability for a phenotypic characterization in the set of {$T_1, \ldots, T_k$} phenotypic characterizations that the biological specimen has the phenotypic characterization such that $$\sum_{j=1}^{k} p_j$$

is equal to a predetermined constant; and (E) optionally, instructions for outputting one or more pairwise probabilities $p_{pq}$ in P to a user interface device, a monitor, a computer readable storage medium, or a local or remote computer system when step (D) is not performed; or instructions for displaying one or more pairwise probabilities $p_{pq}$ in P when step (D) is not performed, or optionally, instructions for outputting one or more $p_j$ in M and/or one or more pairwise probabilities $p_{pq}$ in P to a user interface device, a monitor, a computer readable storage medium, or a local or remote computer system when step (D) is performed; or instructions for displaying one or more $p_j$ in M and/or one or more pairwise probabilities $p_{pq}$ in P when step (D) is performed.

Still another aspect of the present invention provides a computer-readable medium storing a computer program executable by a computer to determine a phenotypic characterization of a test biological specimen using any of the disclosed methods.

4 BRIEF DESCRIPTION OF THE DRAWINGS

FIG. 3 illustrates the probabilities for each of the 15 possible phenotypic characterizations for sample J06_0317P2A in accordance with an embodiment of the present invention, where the test shows that there is a 91.3 percent chance that the tissue of origin for the tumor is thyroid.

Like reference numerals refer to corresponding parts throughout the several views of the drawings.

5 DETAILED DESCRIPTION OF THE INVENTION

Systems and methods for determining a characterization of a specimen from among a set of {$T_1, \ldots, T_k$} phenotypic characterizations are provided. For each respective pair of characterizations ($T_p, T_q$) formed from the set of {$T_1, \ldots, T_k$} phenotypic characterizations, a score of a pairwise probability function is learned. Advantageously, for each respective pair of characterizations ($T_p, T_q$), the pairwise probability $p_{pq}$ that the specimen originated from characterization $T_p$ (or, conversely, $T_q$) is computed using the learned pairwise probability function. Optionally, the pairwise probabilities are converted to a set M of k probabilities $p_i$, where M={$p_1$, $p_2, \ldots, p_k$}, and where each $p_i$ is in M is a probability for a corresponding phenotypic characterization in the set of {$T_1, \ldots, T_k$} phenotypic characterizations and the $p_i$ in M sum to a normalized value such as, for example, unity.

Figure 1:
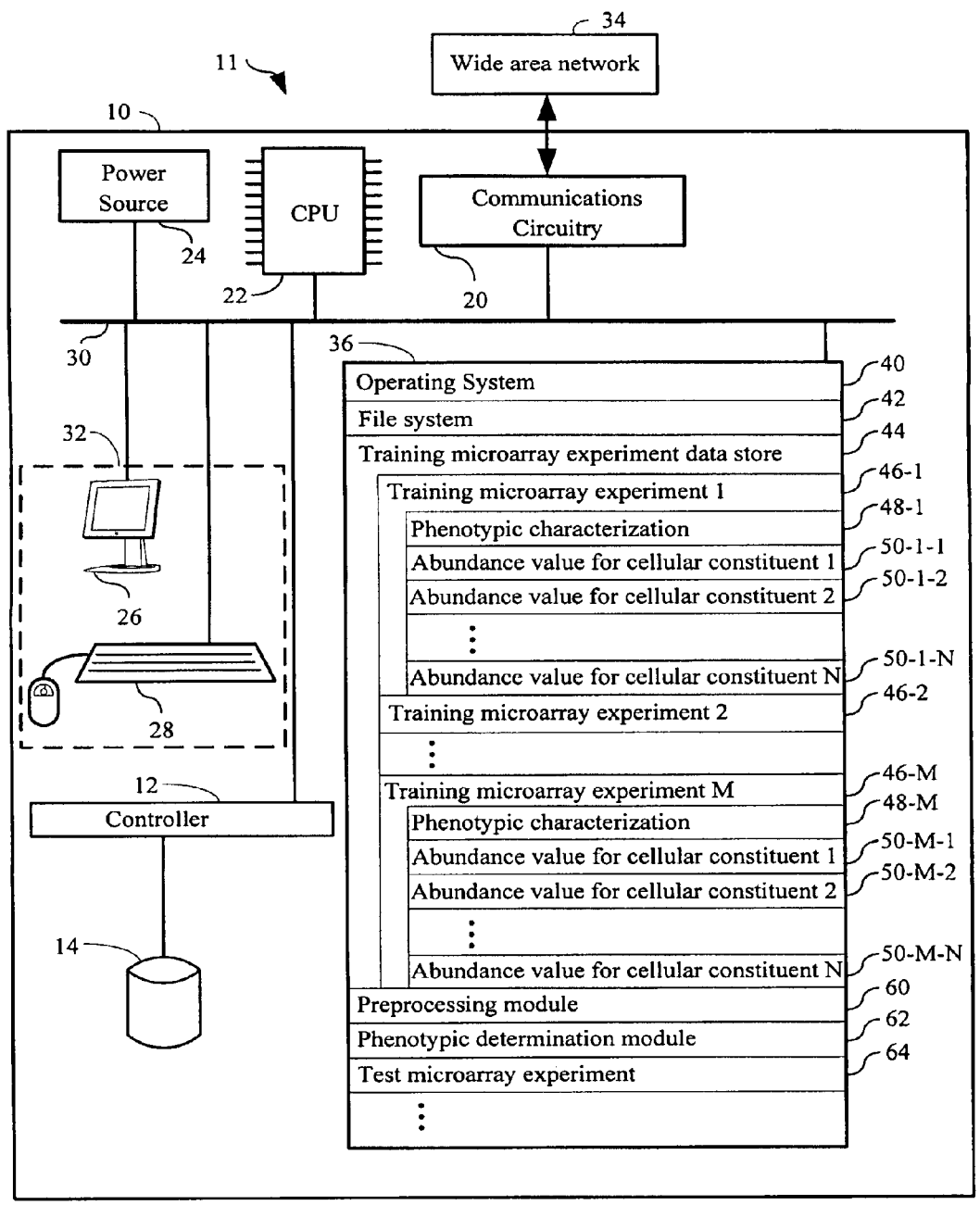
FIG. 1 shows an exemplary computer system for determining a phenotypic characterization of a specimen from among a plurality of phenotypic characterizations in accordance with an embodiment of the present invention.

FIG. 1 details an exemplary system 11 for use in for determining a phenotypic characterization of a specimen from among a plurality of phenotypic characterizations in accordance with the methods of the present invention. The system preferably comprises a computer system 10 having:

a central processing unit 22;

a main non-volatile storage unit 14, for example a hard disk drive, for storing software and data, the storage unit 14 controlled by storage controller 12;

a system memory 36, preferably high speed random-access memory (RAM), for storing system control programs, data, and application programs, comprising programs and data loaded from non-volatile storage unit 14; system memory 36 may also include read-only memory (ROM);

a user interface 32, comprising one or more input devices (e.g., keyboard 28, a mouse) and a display 26 or other output device;

a network interface card 20 (communications circuitry) for connecting to any wired or wireless communication network 34 (e.g., a wide area network such as the Internet);

a power source 24 to power the aforementioned elements; and an internal bus 30 for interconnecting the aforementioned elements of the system.

Operation of computer 10 is controlled primarily by operating system 40, which is executed by central processing unit 22. Operating system 40 can be stored in system memory 36. In a typical implementation, system memory 36 also includes:

a file system 42 for controlling access to the various files and data structures used by the present invention;

training microarray experiment data store 44 that comprises training microarray experiments 46 that are used in determining a phenotypic characterization of a specimen from among a plurality of phenotypic characterizations;

an optional preprocessing module 60 that is optionally used to preprocess training microarray experiments 46; and a phenotypic determination module 62 that is used to determine a phenotypic characterization of a specimen from among a plurality of phenotypic characterizations.

As illustrated in FIG. 1, computer 10 comprises a training microarray experiment data store 44. Training microarray experiment data store 44 can be any form of data storage system including, but not limited to, a flat file, a relational database (SQL), or an on-line analytical processing (OLAP) database (MDX and/or variants thereof). In some specific embodiments, training microarray experiment data store 44 is a hierarchical OLAP cube. In some specific embodiments, training microarray experiment data store 44 comprises a star schema that is not stored as a cube but has dimension tables that define hierarchy. Still further, in some embodiments, training microarray experiment data store 44 has hierarchy that is not explicitly broken out in the underlying database or database schema (e.g., dimension tables that are not hierarchically arranged). In some embodiments, training microarray experiment data store 44 is a single database that includes training microarray experiments 46. In other embodiments, training microarray experiment data store 44 in fact comprises a plurality of databases that may or may not all be hosted by the same computer 10. In such embodiments, some components of training microarray experiment data store 44 are stored on computer systems that are not illustrated by FIG. 1 but that are addressable by wide area network 34.

In some embodiments, training microarray experiment data store 44 has training microarray experiments 46 for at least two phenotypic characterizations, at least three phenotypic characterizations, at least four phenotypic characterizations, at least five different phenotypic characterizations, at least fifteen phenotypic characterizations, at least fifty phenotypic characterizations. In some embodiments, training microarray experiment data store 44 has at least 2, at least 5, at least 8, at least 10, at least twenty-five, at least fifty, at least one hundred, or at least two hundred different training microarray experiments 46 for each such phenotypic characterization.

In some embodiments, training microarray experiment data store 44 and related software modules illustrated in FIG. 1 (e.g. modules 60 and 62) are on a single computer (e.g., computer 10) and in other embodiments training microarray experiment data store 44 and related software modules illustrated in FIG. 1 are hosted by several computers (not shown). In fact, all possible arrangements of training microarray experiment data store 44 and the modules illustrated in FIG. 1 on one or more computers are within the scope of the present invention so long as these components are addressable with respect to each other across computer network 34 or by other electronic means. Thus, the present invention fully encompasses a broad array of computer systems.

As discussed above, system 11 is used to determine a phenotypic characterization of a specimen from among a plurality of phenotypic characterizations in accordance with the methods of the present invention. In some embodiments, prior to determining the phenotypic characterization of the specimen, cellular constituent abundance data for the specimen is standardized using the systems or methods disclosed in U.S. patent application Ser. No. 11/982,064, entitled "Systems and Methods for Standardization of Microarray Data for Diagnostic Use," filed on Oct. 31, 2007.

As depicted in FIG. 1, in typical embodiments, each training microarray experiment 46 comprises a phenotypic characterization 48 of the sample that was used to construct the training microarray experiment 46. Phenotypic characterization 48 is the clinical truth of the training microarray experiment 46. Each training microarray experiment further comprises abundance values 50 for a plurality of cellular constituents. As used herein, the term "cellular constituent" comprises a gene, a protein (e.g., a polypeptide, a peptide), a proteoglycan, a glycoprotein, a lipoprotein, a carbohydrate, a lipid, a nucleic acid, an mRNA, a cDNA, an oligonucleotide, a microRNA, a tRNA, or a protein with a particular modification. Thus, the term cellular constituent comprises a protein encoded by a gene, an mRNA transcribed from a gene, any and all splice variants encoded by a gene, cRNA of mRNA transcribed from a gene, any nucleic acid that contains the nucleic acid sequence of a gene, or any nucleic acid that is hybridizable to a nucleic acid that contains the nucleic acid sequence of a gene or mRNA translated from a gene under standard microarray hybridization conditions. Furthermore, an "abundance value" for a cellular constituent (cellular constituent abundance value) is a quantification of an amount of any of the foregoing, an amount of activity of any of the foregoing, or a degree of modification (e.g., phosphorylation) of any of the foregoing. As used herein, a gene is a transcription unit in the genome, including both protein coding and noncoding mRNAs, cDNAs, or cRNAs for mRNA transcribed from the gene, or nucleic acid derived from any of the foregoing. As such, a transcription unit that is optionally expressed as a protein, but need not be, is a gene. The abundance values used in the claim methods are all of the same class of abundance values. For example, they are all amounts of mRNA, all amounts of cDNA, all amounts of protein, all amounts of metabolites, all activity levels of proteins, or all degrees of chosen modification (e.g., phosphorylation of proteins, etc.).

In some embodiments, the abundance value for a cellular constituent is determined by a degree of modification of a cellular constituent that is encoded by or is a product of a gene (e.g., is a protein or RNA transcript). In some embodiments, a cellular constituent is virtually any detectable compound, such as a protein, a peptide, a proteoglycan, a glycoprotein, a lipoprotein, a carbohydrate, a lipid, a nucleic acid (e.g., DNA, such as cDNA or amplified DNA, or RNA, such as mRNA), an organic or inorganic chemical, a natural or synthetic polymer, a small molecule (e.g., a metabolite) and/or any other variable cellular component or protein activity, degree of protein modification (e.g., phosphorylation), or a discriminating molecule or discriminating fragment of any of the foregoing, that is present in or derived from a biological sample that is modified by, regulated by, or encoded by a gene.

A cellular constituent can, for example, be isolated from a biological sample from a member of the first population, directly measured in the biological sample from the member of the first population, or detected in or determined to be in the biological sample from the member of the first population. A cellular constituent can, for example, be functional, partially functional, or non-functional. In addition, if the cellular constituent is a protein or fragment thereof, it can be sequenced and its encoding gene can be cloned using well-established techniques.

A cellular constituent can be an RNA encoding a gene that, in turn, encodes a protein or a portion of a protein. However, a cellular constituent can also be an RNA that does not necessarily encode for a protein or a portion of a protein. As such, in the present invention, a "gene" is any region of the genome that is transcriptionally expressed. Thus, examples of genes are regions of the genome that encode microRNAs, tRNAs, and other forms of RNA that are encoded in the genome as well as those genes that encode for proteins (e.g. messenger RNA).

In some embodiments, the cellular constituent abundance data for a gene is a degree of modification of the cellular constituent. Such a degree of modification can be, for example, an amount of phosphorylation of the cellular constituent. Such measurements are a form of cellular constituent abundance data. In one embodiment, the abundance of the at least one cellular constituent that is measured and stored as abundance value 50 for a cellular constituent comprises abundances of at least one RNA species present in one or more cells. Such abundances can be measured by a method comprising contacting a gene transcript array with RNA from one or more cells of the organism, or with cDNA derived therefrom. A gene transcript array comprises a surface with attached nucleic acids or nucleic acid mimics. The nucleic acids or nucleic acid mimics are capable of hybridizing with the RNA species or with cDNA derived from the RNA species.

As further depicted in FIG. 1, a test microarray experiment 64 is found within memory 36. The test microarray experiment 64 comprises the set of cellular constituent abundance values for a plurality of cellular constituents measured from the test biological specimen for which phenotypic characterization is sought. As used herein, the term "set of cellular constituent abundance values" refers to a set of 1 or more elements where each element is a cellular constituent abundance value. In some embodiments the set contains between 1 and 10 cellular constituent abundance values, between 1 and 50 cellular constituent values, or between 1 and 2000 cellular constituent values. Therefore, unlike the training microarray experiments 46, there is no phenotypic truth associated with test microarray experiment 64 when the test microarray experiment 64 is received by phenotypic determination module 62.

In some embodiments, a training microarray experiment 46 and/or a test microarray experiment 64 comprises the cellular constituent abundance values from a microarray that is designed to quantify an amount of nucleic acid in a biological sample. Such microarrays are referred to herein as expression microarrays. Examples of such microarrays include, but are not limited to, the Affymetrix GENECHIP Human Genome U133A 2.0 Array (Santa Clara, Calif.) which is a single array representing 14,500 human genes. In the case of training microarray experiments 46, such values are referred to as abundance values 50 as depicted in FIG. 1. In some embodiments, each training microarray experiment 46 and/or test microarray experiment 64 comprises the cellular constituent abundance values from any Affymetrix expression (quantitation) analysis array including, but not limited to, the ENCODE 2.0R array, the HuGeneFL Genome Array, the Human Cancer G110 Array, the Human Exon 1.0 ST Array, the Human Genome Focus Array, the Human Genome U133 Array Plate Set, the Human Genome U133 Plus 2.0 Array, the Human Genome U133 Set, the Human Genome U133A 2.0 Array, the Human Genome U95 Set, the Human Promoter 1.0R array, the Human Tiling 1.0R Array Set, the Human Tiling 2.0R Array Set, and the Human X3P Array.

In some embodiments, a training microarray experiment 46 and/or a test microarray experiment 64 comprises the cellular constituent abundance values from microarrays that are designed for comparative genomic hybridization (CGH). CGH encompasses methods that are used to analyze copy number changes (gains /losses) in the DNA content of biological specimens, and/or discover or validate microdeletions or microinsertions in genomic DNA. Such microarrays are referred to herein as comparative genomic hybridization microarrays. Examples of comparative genomic hybridization microarrays include, but are not limited to, the sub-megabase resolution tiling arrays (SMRT version 1 & 2) which are tiling path resolution microarrays comprising 32,433 and 26,526 synthetic bacterial artificial chromosomes respectively. SMRT array version 1 is spotted in triplicate and SMRT array version 2 is spotted in duplicate on one slide. Both arrays are for use in comparative genomic hybridization experiments. The SMRT arrays are available from the Wan Lam Laboratory at the British Columbia Cancer Research Centre, (Vancouver, British Columbia, Canada). For a description of the use of SMRT arrays in one CGH analysis, see Shah et al., 2006, Bioinformatics 22, e431-e439, which is hereby incorporated by reference herein in its entirety. In some instances CGH arrays are constructed from BAC, PAC, or cosmid clones. Additional CGH microarrays include, but are not limited to, the Affymetrix Mapping 100K set, Mapping 10K 2.0 set, and Mapping 500K set. Additional CGH microarrays include, but are not limited to, the Agilent Human Genome CGH Microarray Kit 244K, the Agilent Human Genome CGH Microarray Kit 105K, and the Agilent Human Genome CGH Microarray Kit 44K.

In some embodiments, a training microarray experiment 46 and/or a test microarray experiment 64 comprises the cellular constituent abundance values from an exon microarray. Exon microarrays provide at least one probe per exon in genes traced by the microarray to allow for analysis of gene expression and alternative splicing. Examples of exon microarrays include, but are not limited to, the Affymetrix GENECHIP® Human Exon 1.0 ST array. The GENECHIP® Human Exon 1.0 ST array supports most exonic regions for both well-annotated human genes and abundant novel transcripts. A total of over one million exonic regions are registered in this microarray system. The probe sequences are designed based on two kinds of genomic sources, i.e. cDNA-based content which includes the human RefSeq mRNAs, GenBank and ESTs from dbEST, and the gene structure sequences which are predicted by GENSCAN, TWINSCAN, and Ensemble. The majority of the probe sets are each composed of four perfect match (PM) probes of length 25 bp, whereas the number of probes for about 10 percent of the exon probe sets is limited to less than four due to the length of probe selection region and sequence constraints. With this microarray platform, no mismatch (MM) probes are available to perform data normalization, for example, background correction of the monitored probe intensities. Instead of the MM probes, the existing systematic biases are removed based on the observed intensities of the background probe probes (BGP) which are designed by Affymetrix. The BGPs are composed of the genomic and antigenomic probes. The genomic BGPs were selected from a research prototype human exon array design based on NCBI build 31. The antigenomic background probe sequences are derived based on reference sequences that are not found in the human (NCBI build 34), mouse (NCBI build 32), or rat (HGSC build 3.1) genomes. Multiple probes per exon enable "exon-level" analysis provide a basis for distinguishing between different isoforms of a gene. This exon-level analysis on a whole-genome scale opens the door to detecting specific alterations in exon usage that may play a central role in disease mechanism and etiology.

In some embodiments, each training microarray experiment 46 and/or each test microarray experiment 64 comprises the cellular constituent abundance values from a microRNA microarray. MicroRNAs (miRNAs) are a class of non-coding RNA genes whose final product is, for example, a 22 nucleotide functional RNA molecule. MicroRNAs play roles in the regulation of target genes by binding to complementary regions of messenger transcripts to repress their translation or regulate degradation. MicroRNAs have been implicated in cellular roles as diverse as developmental timing in worms, cell death and fat metabolism in flies, haematopoiesis in mammals, and leaf development and floral patterning in plants. MicroRNAs may play roles in human cancers. Examples of exon microarrays include, but are not limited to, the Agilent Human miRNA Microarray kit which contains probes for 470 human and 64 human viral microRNAs from the Sanger database v9.1.

In some embodiments, a training microarray experiment 46 and/or a test microarray experiment 64 comprises protein abundance or protein modification measurements that are made using a protein chip assay (e.g., The PROTEINCHIP® Biomarker System, Ciphergen, Fremont, Calif.). See also, for example, Lin, 2004, Modern Pathology, 1-9; Li, 2004, Journal of Urology 171, 1782-1787; Wadsworth, 2004, Clinical Cancer Research 10, 1625-1632; Prieto, 2003, Journal of Liquid Chromatography & Related Technologies 26, 2315-2328; Coombes, 2003, Clinical Chemistry 49, 1615-1623; Mian, 2003, Proteomics 3, 1725-1737; Lehre et al., 2003, BJU International 92, 223-225; and Diamond, 2003, Journal of the American Society for Mass Spectrometry 14, 760-765, each of which is hereby incorporated by reference herein in its entirety. Protein chip assays (protein microarrays) are commercially available. For example, Ciphergen (Fremont, Calif.) markets the PROTEINCHIP® System Series 4000 for quantifying proteins in a sample. Furthermore, Sigma-Aldrich (Saint Lewis, Mo.) sells a number of protein microarrays including the PANORAMA™ Human Cancer v1 Protein Array, the PANORAMA™ Human Kinase v1 Protein Array, the PANORAMA™ Signal Transduction Functional Protein Array, the PANORAMA™ AB Microarray—Cell Signaling Kit, the PANORAMA™ AB Microarray—MAPK and PKC Pathways kit, the PANORAMA™ AB Microarray—Gene Regulation I Kit, and the PANORAMA™ AB Microarray—p53 pathways kit. Further, TeleChem International, Inc. (Sunnyvale, Calif.) markets a Colorimetric Protein Microarray Platform that can perform a variety of micro multiplexed protein microarray assays including microarray based multiplex ELISA assays. See also, MacBeath and Schreiber, 2000, "Printing Proteins as Microarrays for High-Throughput Function Determination," Science 289, 1760-1763, which is hereby incorporated by reference herein in its entirety.

In some embodiments, a training microarray experiment 46 and/or a test microarray experiment 64 comprises the cellular constituent abundance values measured using any of the techniques or microarrays disclosed in Section 5.5, below.

In some embodiments, a training microarray experiment 46 and/or a test microarray experiment 64 comprises a plurality of cellular constituent abundance measurements and wherein the plurality of cellular constituent abundance measurements consists of cellular constituent abundance measurements for between 10 oligonucleotides and $5 \times 10^6$ oligonucleotides. In some embodiments, a training microarray experiment 46 and/or test microarray experiment 64 comprises a plurality of cellular constituent abundance measurements and wherein the plurality of cellular constituent abundance measurements consists of cellular constituent abundance measurements for between 100 oligonucleotides and $1 \times 10^8$ oligonucleotides, between 500 oligonucleotides and $1 \times 10^7$ oligonucleotides, between 1000 oligonucleotides and $1 \times 10^6$ oligonucleotides, or between 2000 oligonucleotides and $1 \times 10^5$ oligonucleotides. In some embodiments, a training microarray experiment 46 and/or a test microarray experiment 64 comprises a plurality of cellular constituent abundance measurements and wherein the plurality of cellular constituent abundance measurements consists of cellular constituent abundance measurements for more than 100, more than 1000, more than 5000, more than 10,000, more than 15,000, more than 20,000, more than 25,000, or more than 30,000 oligonucleotides. In some embodiments, each training microarray experiment 46 and/or each test microarray experiment 64 comprises a plurality of cellular constituent abundance measurements and wherein the plurality of cellular constituent abundance measurements consists of cellular constituent abundance measurements for less than $1 \times 10^7$, less than $1 \times 10^6$, less than $1 \times 10^5$, or less than $1 \times 10^4$ oligonucleotides.

In some embodiments, a training microarray experiment 46 and/or a test microarray experiment 64 comprises a plurality of cellular constituent abundance measurements and wherein the plurality of cellular constituent abundance measurements consists of cellular constituent abundance measurements for between 5 mRNA and 50,000 mRNA. In some embodiments, a training microarray experiment 46 and/or a test microarray experiment 64 comprises a plurality of cellular constituent abundance measurements and wherein the plurality of cellular constituent abundance measurements consists of cellular constituent abundance measurements for between 500 mRNA and 100,000 mRNA, between 2000 mRNA and 80,000 mRNA, or between 5000 mRNA and 40,000 mRNA. In some embodiments, each training microarray experiment 46 and/or each test microarray experiment 64 comprises a plurality of cellular constituent abundance measurements and wherein the plurality of cellular constituent abundance measurements consists of cellular constituent abundance measurements for more than 100 mRNA, more than 500 mRNA, more than 1000 mRNA, more than 2000 mRNA, more than 5000 mRNA, more than 10,000 mRNA, or more than 20,000 mRNA. In some embodiments, each training microarray experiment 46 and/or each test microarray experiment 64 comprises a plurality of cellular constituent abundance measurements and wherein the plurality of cellular constituent abundance measurements consists of cellular constituent abundance measurements for less than 100,000 mRNA, less than 50,000 mRNA, less than 25,000 mRNA, less than 10,000 mRNA, less than 5000 mRNA, or less than 1,000 mRNA.

In some embodiments, each training microarray experiment 46 and/or each test microarray experiment 64 comprises a plurality of cellular constituent abundance measurements and wherein the plurality of cellular constituent abundance measurements consists of cellular constituent abundance measurements for between 50 proteins and 200,000 proteins. In some embodiments, each training microarray experiment 46 and/or each test microarray experiment 64 comprises a plurality of cellular constituent abundance measurements and wherein the plurality of cellular constituent abundance measurements consists of cellular constituent abundance measurements for between 25 proteins and 500,000 proteins, between 50 proteins and 400,000 proteins, or between 1000 proteins and 100,000 proteins. In some embodiments, each training microarray experiment 46 and/or each test microarray experiment 64 comprises a plurality of cellular constituent abundance measurements and wherein the plurality of cellular constituent abundance measurements consists of cellular constituent abundance measurements for more than 100 proteins, more than 500 proteins, more than 1000 proteins, more than 2000 proteins, more than 5000 proteins, more than 10,000 proteins, or more than 20,000 proteins. In some embodiments, each training microarray experiment 46 and/or each test microarray experiment 64 comprises a plurality of cellular constituent abundance measurements and wherein the plurality of cellular constituent abundance measurements consists of cellular constituent abundance measurements for less than 500,000 proteins, less than 250,000 proteins, less than 50,000 proteins, less than 10,000 proteins, less than 5000 proteins, or less than 1,000 proteins.

In some embodiments, the training microarray experiment data store 44 comprises data from a plurality of training microarray experiments, wherein the plurality of training microarray experiments consists of between 50 training microarray experiments and 100,000 training microarray experiments. In some embodiments, training microarray experiment data store 44 comprises data from a plurality of training microarray experiments, wherein the plurality of training microarray experiments consists of between 500 and 50,000 training microarray experiments. In some embodiments, training microarray experiment data store 44 comprises data from a plurality of training microarray experiments, wherein the plurality of training microarray experiments consists of between 100 training microarray experiments and 35,000 training microarray experiments. In some embodiments, training microarray experiment data store 44 comprises data from a plurality of training microarray experiments, wherein the plurality of training microarray experiments consists of between 50 training microarray experiments and 20,000 training microarray experiments.

In some embodiments, the test microarray experiment 64 and/or each training microarray experiment 46 is measured from a microarray comprising probes arranged with a density of 100 different probes per 1 cm² or higher. In some embodiments, the test microarray experiment 64 and/or each training microarray experiment 46 is measured from a microarray comprising probes arranged with a density of at least 2,500 different probes per 1 cm², at least 5,000 different probes per 1 cm², or at least 10,000 different probes per 1 cm². In some embodiments, the test microarray experiment 64 and/or each training microarray experiment 46 is measured from a microarray comprising at least 10,000 different probes, at least 20,000 different probes, at least 30,000 different probes, at least 40,000 different probes, at least 100,000 different probes, at least 200,000 different probes, at least 300,000 different probes, at least 400,000 different probes, or at least 500,000 different probes.

As used herein, a microarray is an array of positionally-addressable binding (e.g., hybridization) sites on a support. In a preferred embodiment, the sites are for binding to many of the nucleotide sequences encoded by the genome of a cell or organism, preferably most or almost all of the transcripts of genes or to transcripts of more than half of the genes having an open reading frame in the genome. In a preferred embodiment, each of such binding sites consists of polynucleotide probes bound to the predetermined region on the support. Microarrays can be made in a number of ways, of which several are described herein below. However produced, preferably microarrays share certain characteristics. The arrays are reproducible, allowing multiple copies of a given array to be produced and easily compared with each other. Preferably, the microarrays are made from materials that are stable under binding (e.g., nucleic acid hybridization) conditions. Microarrays are preferably small, e.g., between 1 cm² and 25 cm², preferably 1 to 3 cm². However, both larger and smaller arrays (e.g., nanoarrays) are also contemplated and may be preferable, e.g., for simultaneously evaluating a very large number or very small number of different probes.

In some embodiments, a phenotypic characterization in the plurality of phenotypic characterizations is a tissue type, an organ type, a cell type, a cell morphology, a disease state, an abnormal state in a tissue or organ, an abnormal cell type, or an abnormal cell morphology. In some embodiments, a phenotypic characterization is a disease prognosis such as (i) expected survival or (ii) expected time to recurrence. In some embodiments, a phenotypic characterization is a therapeutic response. As used herein, the terms "therapeutic response", "response to therapy", "response to treatment", and "clinical outcome" are used interchangeably.

5.1 Exemplary Method

Figure 2:
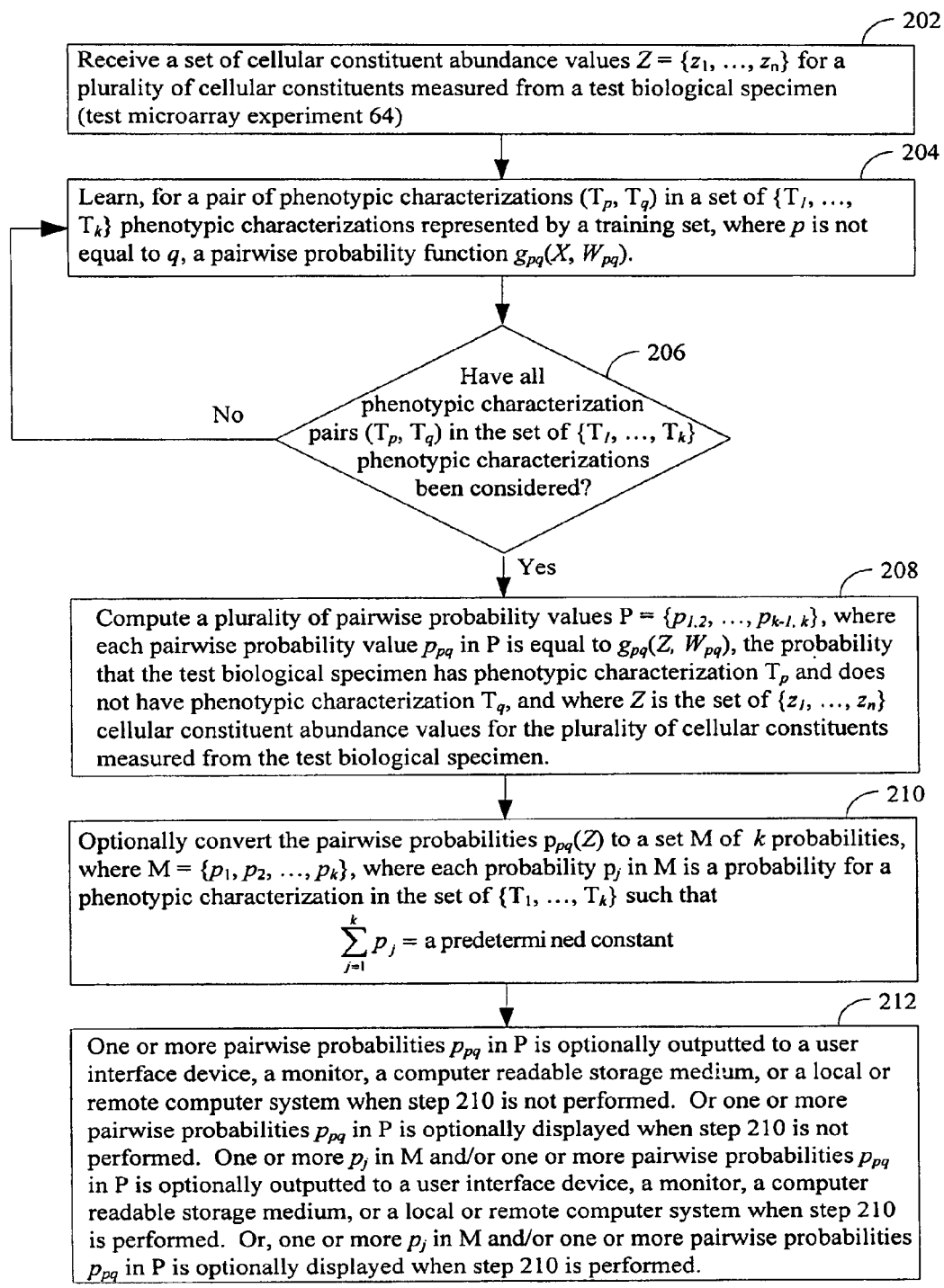
FIG. 2 illustrates an exemplary method for determining a phenotypic characterization of a specimen from among a plurality of phenotypic characterizations in accordance with an embodiment of the present invention.

Referring to FIG. 2, a method for determining a phenotypic characterization of a test biological specimen from among a set of $\{T_1, \ldots, T_k\}$ phenotypic characterizations using a training population is disclosed.

Step 202. In step 202, a test micoarray experiment 64 is received. The test micoarray experiment 64 comprises a set of cellular constituent abundance values $Z=\{z_1, \ldots, z_n\}$ for a plurality of cellular constituents measured from a test biological specimen. In some embodiments, the test micoarray experiment 64 is received in the form of an electronic file or signal by computer 10 from a remote location over wide area network 34, where the wide area network is an example of computer network. The remote location may be in the same building as computer 10, in another building as computer 10, in the same city as computer 10, in a different city as computer 10. The remote location may be in the same or different state, country or continent as computer 10. In some embodiments the test microarray experiment 64 is encrypted. In some embodiments, Z comprises between 10 and 10×10⁶ cellular constituent measurements from the test biological specimen. In some embodiments, Z comprises between 100 and 50,000 cellular constituent abundance measurements from the test biological specimen.

Step 204. In step 204, which may occur before step 202, after step 202, concurrently with step 202, or overlap in time with step 202, a learning phase is performed. Specifically, for a pair of phenotypic characterizations ($T_p$, $T_q$) in the set of $\{T_1, \ldots, T_k\}$ phenotypic characterizations, where p is not equal to q, a pairwise probability function $g_{pq}(X, W_{pq})$ is learned. In other words, for a pair of phenotypic characterizations ($T_p$, $T_q$), the weights $W_{pq}$ for a decision function (pairwise probability function) are determined. In some embodiments, there are at least five training samples in the training population for each phenotypic characterization in the set of $\{T_1, \ldots, T_k\}$ phenotypic characterizations. In some embodiments, there are at least two, at least three, at least four, at least ten, at least twenty, at least fifty, or at least 100 training samples in the training population for each phenotypic characterization in the set of $\{T_1, \ldots, T_k\}$ phenotypic characterizations. In some embodiments, k is at least 3, at least 4, at least 5, at least 6, at least 7, at least 8, at least 9, at least 10, at least 20, at least 30, or between 3 and 50.

To compute the pairwise probability function $g_{pq}(X, W_{pq})$, Y is used. Y is the set of all training samples in the training population that exhibits either phenotypic characterization $T_p$ or phenotypic characterization $T_q$, and each $Y_i$ in Y is the set of $\{y_{i1}, \ldots, y_{in}\}$ cellular constituent abundance values for a plurality of cellular constituents measured from a sample i, from the training population, which exhibits either phenotypic characterization $T_p$ or phenotypic characterization $T_q$, and where n is at least 1, at least 10, at least 15, at least 20, at least 25, at least 50, at least 100, or at least 200. $W_{pq}$ is a set of parameters derived from Y in the learning step (A) for a pair of phenotypic characterizations ($T_p$, $T_q$) by substituting each $Y_i$ into $g_{pq}(X, W_{pq})$, as X, during the learning process. For instance, if $g_{pq}(X, W_{pq})$ is a neural network, each $Y_i$ is used to train the weights of the neural net, collectively, $W_{pq}$, using training methods disclosed below and that are known in the art. Similarly, if $g_{pq}(X, W_{pq})$ is a support vector machine, each $Y_i$ is used to train the weights of the disclosed below, collectively, $W_{pq}$, using training methods known in the art and training methods disclosed below.

Note that, in preferred embodiments $Y_i=\{y_{i1}, \ldots, y_{in}\}$ is the set of n cellular constituent abundance values for a plurality of cellular constituents measured from a single sample i from a training population. Training microarray experiment data store 44 may contain other training microarray experiment 46 that were measured from biological samples that also have phenotypic characterization $T_p$. Here, the index i is used to individually reference each of these training microarray experiment 46.

Unless otherwise indicated herein, any biological sample from an organ, tissue, or biological fluid, e.g., liver tissue sample, pancreatic tissue sample, soft tissue, muscle tissue, bone tissue, bladder tissue, lung tissue, epithelial tissue, endothelial tissue, blood sample, urine, mucosal swab, stool, etc., obtained from any subject may serve as a biological sample from which cellular constituent values $\{y_{i1}, \ldots, y_{in}\}$ are measured for a training microarray experiment 46 provided that the phenotypic characterization of the biological sample is known. Furthermore, unless otherwise indicated herein, any biological sample from an organ, tissue, or biological fluid, e.g., liver tissue sample, pancreatic tissue sample, soft tissue, muscle tissue, bone tissue, bladder tissue, lung tissue, epithelial tissue, endothelial tissue, blood sample, urine, mucosal swab, stool, etc., obtained from any subject may serve as a test biological sample from which cellular constituent values $Z=\{z_1, \ldots, z_n\}$ are measured for the test microarray experiment 64 regardless of whether the phenotypic characterization of the biological sample is suspected or known.

Below are non-limiting examples of the form that pairwise probability function $g_{pq}(X, W_{pq})$ may take. Given the disclosure herein, one of skill in the art will appreciate that other pattern classification or regression techniques and algorithms may be used for the pairwise probability function $g_{pq}(X, W_{pq})$ and the present invention encompasses all such techniques. Furthermore, it will be appreciated that an additional step may be needed to convert the output of some of the classifiers described below (e.g., clustering, decision trees, and linear discriminant analysis), to a format that can be used to compute probabilities in accordance with the present invention. This additional step can be perfomed using methods known in the art such as Monte Carlo techniques.

Decision tree. In one embodiment the learned pairwise probability function $g_{pq}(X, W_{pq})$ is a decision tree. Decision trees are described generally in Duda, 2001, *Pattern Classification*, John Wiley & Sons, Inc., New York, pp. 395-396, which is hereby incorporated herein by reference. One specific algorithm that can be used to learn the pairwise probability function $g_{pq}(X, W_{pq})$ is a classification and regression tree (CART). Other specific algorithms for learning the pairwise probability function include, but are not limited to, ID3, C4.5, MART, and Random Forests. CART, ID3, and C4.5, each described in Duda, 2001, *Pattern Classification*, John Wiley & Sons, Inc., New York, pp. 396-408 and pp. 411-412, which is hereby incorporated by reference herein in its entirety. CART, MART, and C4.5 are also described in Hastie et al., 2001, *The Elements of Statistical Learning*, Springer-Verlag, New York, Chapter 9, which is hereby incorporated by reference herein in its entirety. The Random Forests technique is described in Breiman, 1999, "Random Forests—Random Features," Technical Report 567, Statistics Department, University of California at Berkeley, September 1999, which is hereby incorporated by reference herein in its entirety.

In addition to univariate decision trees in which each split is based on a cellular constituent abundance values for a corresponding cellular constituent in Y, or the relative cellular constituent abundance value of two such biomarkers, a learned pairwise probability function $g_{pq}(X, W_{pq})$ can be a multivariate decision tree. In such a multivariate decision tree, some or all of the decisions actually comprise a linear combination of cellular constituent abundance values for a plurality of cellular constituents in Y. Such a linear combination can be trained to derive the learned pairwise probability function $g_{pq}(X, W_{pq})$ using known techniques such as gradient descent on a classification or by the use of a sum-squared-error criterion. To illustrate such a decision tree, consider the expression:

$$0.04x_1 + 0.16x_2 < 500$$

Here, $x_1$ and $x_2$ refer to two different cellular constituent abundance values for two different cellular constituents from among the cellular constituents in Y. To poll the learned pairwise probability function, the values of cellular constituents $x_1$ and $x_2$ are taken from the measurements of the test biological specimen received in step 202. These values are then inserted into the equation. If a value of less than 500 is computed, then a first branch in the decision tree is taken. Otherwise, a second branch in the decision tree is taken. Multivariate decision trees are described in Duda, 2001, *Pattern Classification*, John Wiley & Sons, Inc., New York, pp. 408-409, which is hereby incorporated by reference herein in its entirety.

Multivariate adaptive regression splines. Another approach that can be used to learn a pairwise probability function $g_{pq}(X, W_{pq})$ uses multivariate adaptive regression splines (MARS). MARS is an adaptive procedure for regression, and is well suited for the high-dimensional problems addressed by the present invention. MARS can be viewed as a generalization of stepwise linear regression or a modification of the CART method to improve the performance of CART in the regression setting. MARS is described in Hastie et al., 2001, *The Elements of Statistical Learning*, Springer-Verlag, New York, pp. 283-295, which is hereby incorporated by reference herein in its entirety.

Centroid classifier techniques. In one embodiment the pairwise probability function $g_{pq}(X, W_{pq})$ is learned using a nearest centroid classifier technique. Such a technique computes, for phenotypic characterizations $T_p$ and $T_q$, a centroid given by the average cellular constituent abundance levels of the biomarkers from biological specimens in the training population in the phenotypic characterization class ($T_p$ or $T_q$), and then assigns new samples (the test biological specimen) to the class whose centroid is nearest. This approach is similar to k-means clustering except clusters are replaced by known classes. This algorithm can be sensitive to noise when a large number of cellular constituents are used. One enhancement to the technique uses shrinkage: for each cellular constituent in Y used, differences between phenotypic characterization class ($T_p$ or $T_q$) centroids are set to zero if they are deemed likely to be due to chance. This approach is implemented in the Prediction Analysis of Microarray, or PAM. See, for example, Tibshirani et al., 2002, *Proceedings of the National Academy of Science USA* 99; 6567-6572, which is hereby incorporated by reference herein in its entirety. Shrinkage is controlled by a threshold below which differences are considered noise. Cellular constituents that show no difference above the noise level are removed. A threshold can be chosen by cross-validation. As the threshold is decreased, more cellular constituents from Y are included and estimated classification errors decrease, until they reach a bottom and start climbing again as a result of noise biomarkers—a phenomenon known as overfitting.

Bagging, boosting, the random subspace method and additive trees. In some embodiments, a learned pairwise probability function $g_{pq}(X, W_{pq})$ can be refined and improved using bagging, boosting, the random subspace method, and additive trees. These techniques are designed for, and usually applied to, decision trees, such as the decision trees described above. In addition, such techniques can also be useful in decision rules developed using other types of data analysis algorithms such as linear discriminant analysis.

In bagging, one samples the training set Y, generating random independent bootstrap replicates, constructs the pairwise probability function $g_{pq}(X, W_{pq})$ on each of these, and aggregates them by a simple majority vote in the final learned pairwise probability function $g_{pq}(X, W_{pq})$. See, for example, Breiman, 1996, Machine Learning 24, 123-140; and Efron & Tibshirani, *An Introduction to Boostrap*, Chapman & Hall, New York, 1993, which is hereby incorporated by reference herein in its entirety.

In boosting, Y is divided into a training set and a test set and the pairwise probability function $g_{pq}(X, W_{pq})$ is learned using the training set, which is dependent on previous classification results. Initially, all $Y_i$ in the training set have equal weights, and the first learned pairwise probability function $g_{pq}(X, W_{pq})$ is constructed on this data set. Then, weights are changed according to the performance of the pairwise probability function $g_{pq}(X, W_{pq})$ (e.g., the performance of the pairwise probability function $g_{pq}(X, W_{pq})$ against the test set). Erroneously classified subjects in the training set get larger weights, and the next decision rule is boosted on the reweighted training set. In this way, a sequence of training sets and trained pairwise probability functions $g_{pq}(X, W_{pq})$ is obtained, which is then combined by simple majority voting or by weighted majority voting in the final trained pairwise probability function $g_{pq}(X, W_{pq})$. See, for example, Freund & Schapire, "Experiments with a new boosting algorithm," Proceedings 13th International Conference on Machine Learning, 1996, 148-156, which is hereby incorporated by reference herein in its entirety.

In some embodiments, modifications of the boosting methods proposed by Freund and Schapire, 1997, Journal of Computer and System Sciences 55, pp. 119-139, are used. See, for example, Hasti et al., *The Elements of Statistical Learning*, 2001, Springer, New York, Chapter 10, which is hereby incorporated by reference herein in its entirety. For example, in some embodiments, cellular constituent preselection from Y is performed using a technique such as the nonparametric scoring methods of Park et al., 2002, Pac. Symp. Biocomput. 6, 52-63, which is hereby incorporated by reference herein in its entirety. Cellular constituent preselection is a form of dimensionality reduction in which the cellular constituents in Y that discriminate between phenotypic characterizations Tp and Tq the best are selected for use in the classifier. Then, the LogitBoost procedure introduced by Friedman et al., 2000, Ann Stat 28, 337-407, is used rather than the boosting procedure of Freund and Schapire. In some embodiments, the boosting and other classification methods of Ben-Dor et al., 2000, Journal of Computational Biology 7, 559-583, hereby incorporated by reference herein in its entirety, are used in the present invention. In some embodiments, the boosting and other classification methods of Freund and Schapire, 1997, Journal of Computer and System Sciences 55, 119-139, hereby incorporated by reference herein in its entirety, are used.

In some embodiments, the random subspace method is used in which candidate pairwise probability functions $g_{pq}(X, W_{pq})$ are constructed in random subspaces of the data feature space. These pairwise probability functions $g_{pq}(X, W_{pq})$ are usually combined by simple majority voting in the final decision rule. See, for example, Ho, "The Random subspace method for constructing decision forests," IEEE Trans Pattern Analysis and Machine Intelligence, 1998; 20(8): 832-844, which is hereby incorporated by reference herein in its entirety.

In one embodiment the pairwise probability function $g_{pq}(X, W_{pq})$ is learned using a multiple additive regression tree (MART). See, for example, Hastie et al., 2001, *The Elements of Statistical Learning*, Springer-Verlag, New York, Chapter 10, which is hereby incorporated by reference herein in its entirety.

Regression. In some embodiments, the pairwise probability function $g_{pq}(X, W_{pq})$ is learned using regression. In such embodiments, the pairwise probability function $g_{pq}(X, W_{pq})$ can be characterized as a regression classifier, such as a logistic regression classifier. Such a regression classifier includes a coefficient for each of the cellular constituents in Y used to construct the classifier. In such embodiments, the coefficients for the regression classifier ($W_{pq}$) are computed using, for example, a maximum likelihood approach. In such a computation, the cellular constituent abundance values for the cellular constituents from Y are used.

Neural networks. In some embodiments, the pairwise probability function $g_{pq}(X, W_{pq})$ is learned using a neural network. A neural network is a two-stage regression or classification decision rule. A neural network has a layered structure that includes a layer of input units (and the bias) connected by a layer of weights to a layer of output units. For regression, the layer of output units typically includes just one output unit. However, neural networks can handle multiple quantitative responses in a seamless fashion.

In multilayer neural networks, there are input units (input layer), hidden units (hidden layer), and output units (output layer). There is, furthermore, a single bias unit that is connected to each unit other than the input units. Neural networks are described in Duda et al., 2001, *Pattern Classification*, Second Edition, John Wiley & Sons, Inc., New York; and Hastie et al., 2001, *The Elements of Statistical Learning*, Springer-Verlag, New York, each of which is hereby incorporated by reference herein in its entirety. Neural networks are also described in Draghici, 2003, *Data Analysis Tools for DNA Microarrays*, Chapman & Hall/CRC; and Mount, 2001, *Bioinformatics: sequence and genome analysis*, Cold Spring Harbor Laboratory Press, Cold Spring Harbor, N.Y., each of which is hereby incorporated by reference herein in its entirety. What are disclosed below are some exemplary forms of neural networks.

The basic approach to the use of neural networks is to start with an untrained network, present a training pattern to the input layer, and to pass signals through the net and determine the output at the output layer. These outputs are then compared to the target values; any difference corresponds to an error. This error or criterion function is some scalar function of the weights $W_{pq}$ and is minimized when the network outputs match the desired outputs. Thus, the weights $W_{pq}$ are adjusted to reduce this measure of error. For regression, this error can be sum-of-squared errors. For classification, this error can be either squared error or cross-entropy (deviation). See, e.g., Hastie et al., 2001, *The Elements of Statistical Learning*, Springer-Verlag, New York, which is hereby incorporated by reference herein in its entirety.

Three commonly used training protocols are stochastic, batch, and on-line. In stochastic training, patterns are chosen randomly from the training set and the network weights $W_{pq}$ are updated for each pattern presentation. Multilayer nonlinear networks trained by gradient descent methods such as stochastic back-propagation perform a maximum-likelihood estimation of the weight values $W_{pq}$ in the classifier defined by the network topology. In batch training, all patterns are presented to the network before learning takes place. Typically, in batch training, several passes are made through the training data. In online training, each pattern is presented once and only once to the net.

In some embodiments, consideration is given to starting values for weights $W_{pq}$. If the weights $W_{pq}$ are near zero, then the operative part of the sigmoid commonly used in the hidden layer of a neural network (see, e.g., Hastie et al., 2001, *The Elements of Statistical Learning*, Springer-Verlag, New York, hereby incorporated by reference herein) is roughly linear, and hence the neural network collapses into an approximately linear classifier. In some embodiments, starting values for weights $W_{pq}$ are chosen to be random values near zero. Hence the classifier starts out nearly linear, and becomes nonlinear as the weights increase. Individual units localize to directions and introduce nonlinearities where needed. Use of exact zero weights $W_{pq}$ leads to zero derivatives and perfect symmetry, and the algorithm never moves. Alternatively, starting with large weights $W_{pq}$ often leads to poor solutions.

Since the scaling of inputs determines the effective scaling of weights $W_{pq}$ in the bottom layer, it can have a large effect on the quality of the final solution. Thus, in some embodiments, at the outset, all expression values are standardized to have mean zero and a standard deviation of one. This ensures all inputs are treated equally in the regularization process, and allows one to choose a meaningful range for the random starting weights.

A recurrent problem in the use of three-layer networks is the optimal number of hidden units to use in the network. The number of inputs and outputs of a three-layer network are determined by the problem to be solved. In the present invention, the number of inputs for a given neural network will equal the number of biomarkers selected from Y. The number of output for the neural network will typically be just one. If too many hidden units are used in a neural network, the network will have too many degrees of freedom and if trained too long, there is a danger that the network will overfit the data. If there are too few hidden units, the training set cannot be learned. Generally speaking, however, it is better to have too many hidden units than too few. With too few hidden units, the classifier might not have enough flexibility to capture the nonlinearities in the date; with too many hidden units, the extra weight can be shrunk towards zero if appropriate regularization or pruning, as described below, is used. In typical embodiments, the number of hidden units is somewhere in the range of 5 to 100, with the number increasing with the number of inputs and number of training cases.

Clustering. In some embodiments, the pairwise probability function $g_{pq}(X, W_{pq})$ is learned using clustering. In some embodiments, cellular constituent abundance values for select cellular constituents in Y are used to cluster individual biological samples in the training population represented by Y. For example, consider the case in which ten cellular constituent abundance values for ten corresponding cellular constituents in Y is used. Each member m of the training population will have cellular constituent abundance values for each of the ten cellular constituents. Such values from a member m in the training population define the vector:

| $X_{1m}$ | $X_{2m}$ | $X_{3m}$ | $X_{4m}$ | $X_{5m}$ | $X_{6m}$ | $X_{7m}$ | $X_{8m}$ | $X_{9m}$ | $X_{10m}$ | where $X_{im}$ is the cellular constituent abundance level of the i$^{th}$ cellular constituent in organism m. If there are m organisms in the training set, selection of i cellular constituents will define m vectors. In some embodiments, prior to clustering, the cellular constituent abundance values are normalized to have a mean value of zero and unit variance.

Those members of the training population that exhibit similar expression patterns across the training population will tend to cluster together. A particular combination of cellular constituents in Y is considered to be a good classifier in this aspect of the invention when the vectors cluster into the phenotypic characterizations $T_p$ and $T_q$. Clustering is described on pages 211-256 of Duda and Hart, *Pattern Classification and Scene Analysis*, 1973, John Wiley & Sons, Inc., New York, (hereinafter "Duda 1973") which is hereby incorporated by reference in its entirety. As described in Section 6.7 of Duda 1973, the clustering problem is described as one of finding natural groupings in a dataset. To identify natural groupings, two issues are addressed. First, a way to measure similarity (or dissimilarity) between two samples is determined. This metric (similarity measure) is used to ensure that the samples in one cluster are more like one another than they are to samples in other clusters. Second, a mechanism for partitioning the data into clusters using the similarity measure is determined.

Similarity measures are discussed in Section 6.7 of Duda 1973, where it is stated that one way to begin a clustering investigation is to define a distance function and to compute the matrix of distances between all pairs of samples in a dataset. If distance is a good measure of similarity, then the distance between samples in the same cluster will be significantly less than the distance between samples in different clusters. However, as stated on page 215 of Duda 1973, clustering does not require the use of a distance metric. For example, a nonmetric similarity function s(x, x') can be used to compare two vectors x and x'. Conventionally, s(x, x') is a symmetric function whose value is large when x and x' are somehow "similar". An example of a nonmetric similarity function s(x, x') is provided on page 216 of Duda 1973.

Once a method for measuring "similarity" or "dissimilarity" between points in a dataset has been selected, clustering requires a criterion function that measures the clustering quality of any partition of the data. Partitions of the data set that extremize the criterion function are used to cluster the data. See page 217 of Duda 1973. Criterion functions are discussed in Section 6.8 of Duda 1973. More recently, Duda et al., Pattern Classification, 2$^{nd}$ edition, John Wiley & Sons, Inc. New York, has been published. Pages 537-563 describe clustering in detail. More information on clustering techniques can be found in Kaufman and Rousseeuw, 1990, *Finding Groups in Data: An Introduction to Cluster Analysis*, Wiley, New York, N.Y.; Everitt, 1993, *Cluster analysis* (3d ed.), Wiley, New York, N.Y.; and Backer, 1995, *Computer-Assisted Reasoning in Cluster Analysis*, Prentice Hall, Upper Saddle River, N.J. Particular exemplary clustering techniques that can be used in the present invention include, but are not limited to, hierarchical clustering (agglomerative clustering using nearest-neighbor algorithm, farthest-neighbor algorithm, the average linkage algorithm, the centroid algorithm, or the sum-of-squares algorithm), k-means clustering, fuzzy k-means clustering algorithm, and Jarvis-Patrick clustering.

Principal component analysis. In some embodiments, the pairwise probability function $g_{pq}(X, W_{pq})$ is learned using principal component analysis. Principal component analysis is a classical technique to reduce the dimensionality of a data set by transforming the data to a new set of variable (principal components) that summarize the features of the data. See, for example, Jolliffe, 1986, *Principal Component* Analysis, Springer, New York, which is hereby incorporated by reference herein in its entirety. Principal component analysis is also described in Draghici, 2003, *Data Analysis Tools for DNA Microarrays*, Chapman & Hall/CRC, which is hereby incorporated by reference herein in its entirety. What follows is non-limiting examples of principal components analysis.

Principal components (PCs) are uncorrelated and are ordered such that the k$^{th}$ PC has the k$^{th}$ largest variance among PCs. The k$^{th}$ PC can be interpreted as the direction that maximizes the variation of the projections of the data points such that it is orthogonal to the first k-1 PCs. The first few PCs capture most of the variation in the data set. In contrast, the last few PCs are often assumed to capture only the residual 'noise' in the data.

In one approach to using PCA to learn a pairwise probability function $g_{pq}(X, W_{pq})$, vectors for the select cellular constituents in Y can be constructed in the same manner described for clustering above. In fact, the set of vectors, where each vector represents the cellular constituent abundance values for the select cellular constituents from a particular member of the training population, can be viewed as a matrix. In some embodiments, this matrix is represented in a Free-Wilson method of qualitative binary description of monomers (Kubinyi, 1990, *3D QSAR in drug design theory methods and applications*, Pergamon Press, Oxford, pp 589-638, hereby incorporated by reference herein), and distributed in a maximally compressed space using PCA so that the first principal component (PC) captures the largest amount of variance information possible, the second principal component (PC) captures the second largest amount of all variance information, and so forth until all variance information in the matrix has been considered.

Then, each of the vectors, where each vector represents a member of the training population, is plotted. Many different types of plots are possible. In some embodiments, a one-dimensional plot is made. In this one-dimensional plot, the value for the first principal component from each of the members of the training population is plotted. In this form of plot, the expectation is that members of phenotypic characterization $T_p$ will cluster in one range of first principal component values and members of phenotypic characterization $T_q$ will cluster in a second range of first principal component values.

In some embodiments, the members of the training population are plotted against more than one principal component. For example, in some embodiments, the members of the training population are plotted on a two-dimensional plot in which the first dimension is the first principal component and the second dimension is the second principal component. In such a two-dimensional plot, the expectation is that members of phenotypic characterization $T_p$ and $T_q$ will cluster into two discrete groups.

Nearest neighbor analysis. In some embodiments, the pairwise probability function $g_{pq}(X, W_{pq})$ is learned using nearest neighbor analysis. Nearest neighbor classifiers are memory-based and require no classifier to be fit. Given a query point $x_0$, the k training points $x_{(r)}$, r, . . . , k closest in distance to $x_0$ are identified and then the point $x_0$ is classified using the k nearest neighbors. Ties can be broken at random. In some embodiments, Euclidean distance in feature space is used to determine distance as:

$$d_{(i)} = \|x_{(i)} - x_0\|.$$

Typically, when the nearest neighbor algorithm is used, the cellular constituent abundance data from Y used to compute the linear discriminant is standardized to have mean zero and variance 1. In the present invention, the members of the training population are randomly divided into a training set and a test set. For example, in one embodiment, two thirds of the members of the training population are placed in the training set and one third of the members of the training population are placed in the test set. A select combination of cellular constituents in Y represents the feature space into which members of the test set are plotted. Next, the ability of the training set to correctly characterize the members of the test set is computed. In some embodiments, nearest neighbor computation is performed several times for a given combination of cellular constituents in Y. In each iteration of the computation, the members of the training population are randomly assigned to the training set and the test set. Then, the quality of the combination of biomarkers is taken as the average of each such iteration of the nearest neighbor computation.

The nearest neighbor rule can be refined to deal with issues of unequal class priors, differential misclassification costs, and feature selection. Many of these refinements involve some form of weighted voting for the neighbors. For more information on nearest neighbor analysis, see Duda, *Pattern Classification*, Second Edition, 2001, John Wiley & Sons, Inc; and Hastie, 2001, *The Elements of Statistical Learning*, Springer, New York, each of which is hereby incorporated by reference herein in its entirety.

Linear discriminant analysis. In some embodiments, the pairwise probability function $g_{pq}(X, W_{pq})$ is learned using linear discrimnant analysis. Linear discriminant analysis (LDA) attempts to classify a subject into one of two categories based on certain object properties. In other words, LDA tests whether object attributes measured in an experiment predict categorization of the objects. LDA typically requires continuous independent variables and a dichotomous categorical dependent variable. In the present invention, the cellular constituent abundance values for the select combinations of cellular constituents across a subset of the training population serve as the requisite continuous independent variables. The trait subgroup classification (phenotypic characterization $T_p$ or $T_q$) of each of the members of the training population serves as the dichotomous categorical dependent variable.

LDA seeks the linear combination of variables that maximizes the ratio of between-group variance and within-group variance by using the grouping information. Implicitly, the linear weights ($W_{pq}$) used by LDA depend on how the cellular constituent abundances of a cellular constituent across the training set separates in the two groups (phenotypic characterization $T_p$ or $T_q$) and how these feature values correlate with the feature values of other biomarkers. In some embodiments, LDA is applied to the data matrix of the N members in the training sample by K cellular constituents in a combination of cellular constituents in Y. Then, the linear discriminant of each member of the training population is plotted. Ideally, those members of the training population representing phenotypic characterization $T_p$ will cluster into one range of linear discriminant values (e.g., negative) and those members of the training population representing phenotypic characterization $T_q$ will cluster into a second range of linear discriminant values (e.g., positive). The LDA is considered more successful when the separation between the clusters of discriminant values is larger. For more information on linear discriminant analysis, see Duda, *Pattern Classification*, Second Edition, 2001, John Wiley & Sons, Inc; and Hastie, 2001, *The Elements of Statistical Learning*, Springer, New York; and Venables & Ripley, 1997, *Modern Applied Statistics with s-plus*, Springer, New York, each of which is hereby incorporated by reference herein in its entirety.

Quadratic discriminant analysis. In some embodiments, the pairwise probability function $g_{pq}(X, W_{pq})$ is learned using linear discrimnant analysis. Quadratic discriminant analysis (QDA) takes the same input parameters and returns the same results as LDA. QDA uses quadratic equations, rather than linear equations, to produce results. LDA and QDA are interchangeable, and which to use is a matter of preference and/or availability of software to support the analysis. Logistic regression takes the same input parameters and returns the same results as LDA and QDA.

Support vector machine. In some embodiments, the pairwise probability function $g_{pq}(X, W_{pq})$ is learned using a support vector machine. SVMs are described, for example, in Cristianini and Shawe-Taylor, 2000, *An Introduction to Support Vector Machines*, Cambridge University Press, Cambridge; Boser et al., 1992, "A training algorithm for optimal margin classifiers," in *Proceedings of the 5th Annual ACM Workshop on Computational Learning Theory*, ACM Press, Pittsburgh, Pa., pp. 142-152; Vapnik, 1998, *Statistical Learning Theory*, Wiley, N.Y.; Mount, 2001, *Bioinformatics: sequence and genome analysis*, Cold Spring Harbor Laboratory Press, Cold Spring Harbor, N.Y., Duda, *Pattern Classification*, Second Edition, 2001, John Wiley & Sons, Inc.; and Hastie, 2001, *The Elements of Statistical Learning*, Springer, New York; and Furey et al., 2000, Bioinformatics 16, 906-914, each of which is hereby incorporated by reference herein in its entirety. When used for classification, SVMs separate a given set of binary labeled data training data with a hyperplane that is maximally distant from them. For cases in which no linear separation is possible, SVMs can work in combination with the technique of 'kernels', which automatically realizes a non-linear mapping to a feature space. The hyperplane found by the SVM in feature space corresponds to a non-linear decision boundary in the input space.

In one example, in order to derive the set of weights $W_{pq}$, the cellular constituent abundance data in training microarray experiments 46 for training microarray experiments 46 that have phenotypic characterization 48 that is $T_p$ or $T_q$ are used in a support vector machine. For example, consider the case in which there are 14 training microarray experiments 46 that have phenotypic characterization 48 that is $T_p$ and 27 training microarray experiments 46 that have phenotypic characterization 48 that is $T_p$. The cellular constituent abundance values 50 for cellular constituents from the 14 training microarray experiments 46 that have phenotypic characterization 48 that is $T_q$ and the 27 training microarray experiments 46 that have phenotypic characterization 48 that is $T_q$ are used in a support vector machine in order to derive the weights $W_{pq}$ for the pairwise probability function $g_{pq}(X, W_{pq})$ for phenotypic characterizations $(T_p, T_q)$. For more information on support vector machines see, for example, Furey et al., 2000, Bioinformatics 16, page 906-914, which is hereby incorporated by reference herein.

In the case of support vector machines, for each pair of phenotypic characterizations $(T_p, T_q)$, there are a set of weights $\{w'_i s, w''_j, b\}$ that need to be derived in order to learn the pairwise probability function $g_{pq}(X, W_{pq})$. In other words, $W_{pq} = \{w'_i s, w''_j, b\}$ when $g_{pq}(X, W_{pq})$ is learned using a support vector machine. In one example, in order to derive the set of weights $\{w'_i s, w''_j, b\}$, the cellular constituent abundance data in training microarray experiments 46 for training microarray experiments 46 that have phenotypic characterization 48 that is $T_p$ or $T_q$ are used in a support vector machine. For example, consider the case in which there are 14 training microarray experiments 46 that have phenotypic characterization 48 that is $T_p$ and 27 training microarray experiments 46 that have phenotypic characterization 48 that is $T_q$. The abundance values 50 for cellular constituents from the 14 training microarray experiments 46 that have phenotypic characterization 48 that is $T_p$ and the 27 training microarray experiments 46 that have phenotypic characterization 48 that is $T_q$ are used in a support vector machine in order to derive the weights $w'_i s$, $w''_j$, and b. For more information on support vector machines see, for example, Furey et al., 2000, Bioinformatics 16, page 906-914, which is hereby incorporated by reference herein.

Evolutionary methods. In some embodiments, the pairwise probability function $g_{pq}(X, W_{pq})$ is learned using evolutionary methods. In broad overview, such methods create several pairwise probability functions—a population—from a combination of cellular constituents in Y. Each pairwise probability function varies somewhat from the other. Next, the pairwise probability functions are scored on cellular constituent abundance data across the training population. In keeping with the analogy with biological evolution, the resulting (scalar) score is sometimes called the fitness. The pairwise probability functions are ranked according to their score and the pairwise probability functions are retained (some portion of the total population of pairwise probability function). Again, in keeping with biological terminology, this is called survival of the fittest. The pairwise probability functions are stochastically altered in the next generation—the children or offspring. Some offspring pairwise probability functions will have higher scores than their parents in the previous generation, some will have lower scores. The overall process is then repeated for the subsequent generation: the pairwise probability functions are scored and the best ones are retained, randomly altered to give yet another generation, and so on. In part, because of the ranking, each generation has, on average, a slightly higher score than the previous one. The process is halted when the single best pairwise probability function in a generation has a score that exceeds a desired criterion value. More information on evolutionary methods is found in, for example, Duda, *Pattern Classification*, Second Edition, 2001, John Wiley & Sons, Inc., which is hereby incorporated by reference herein in its entirety.

Projection pursuit, weighted voting. The data analysis algorithms described above are merely examples of the types of methods that can be used to learn the pairwise probability function $g_{pq}(X, W_{pq})$. Moreover, combinations of the techniques described above can be used. Some combinations, such as the use of the combination of decision trees and boosting, have been described. However, many other combinations are possible. In addition, in other techniques in the art such as Projection Pursuit or Weighted Voting can be used to learn the pairwise probability function $g_{pq}(X, W_{pq})$.

Other methods. In some embodiments, the pairwise probability function $g_{pq}(X, W_{pq})$ is learned using k-nearest neighbors (k-NN), an artificial neural network (ANN), a parametric linear equation, a parametric quadratic equation, a naive Bayes analysis, linear discriminant analysis, a decision tree, or a radial basis function.

Step 206. In step 206, a determination is made as to whether all phenotypic characterization pairs $(T_p, T_q)$ in the set of $\{T_1, \ldots, T_k\}$ phenotypic characterizations have been considered by an instance of step 204. In this manner, the learning step of 204 is repeated for a different pair of phenotypic characterizations $(T_p, T_q)$ for all unique pairs of phenotypic characterizations in the set of $\{T_1, \ldots, T_k\}$ phenotypic characterizations, thereby deriving a plurality of pairwise probability functions $G=\{g_{1,2}(X, W_{1,2}), \ldots, g_{k-1, k}(X, W_{k-1, k})\}$. In preferred embodiments, the same type of classifier (e.g., support vector machine, neural network) is used for each pairwise probability function in G.

Step 208. In step 208, a plurality of pairwise probability values $P=\{p_{1,2}, \ldots, p_{k-1, k}\}$ are computed, where each pairwise probability value $p_{pq}$ in P is equal to $g_{pq}(Z, W_{pq})$ in G, the probability that the test biological specimen has phenotypic characterization $T_p$ and does not have phenotypic characterization $T_q$, and where Z is a set of $\{z_1, \ldots, z_n\}$ cellular constituent abundance values measured from the test biological specimen for the plurality of cellular constituents. Thus, a pairwise probability value $p_{pq}$ is determined for each unique pair of phenotypic characterizations p and q in the $\{T_1, \ldots, T_k\}$ phenotypic characterizations in the training population.

In some embodiments, where the pairwise probability function was learned using a support vector machine, $g_{pq}(Z, W_{pq})$ has the form:

$$g_{pq}(Z, W_{pq}) = \sum_{R_i \in p} w'_i s(Z, R_i) - \sum_{R_j \in q} w''_j s(Z, R_j) + b$$

where $R_i = \{r_{i1}, \ldots, r_{in}\}$ is the set of n cellular constituent abundance values for the plurality of cellular constituents measured from a sample i, from the training population, where sample i has phenotypic characterization $T_p$;

$R_j = \{r_{j1}, \ldots, r_{jn}\}$ is the set of n cellular constituent abundance values for the plurality of cellular constituents measured from a sample j, from the training population, where sample j has phenotypic characterization $T_q$;

$s(Z, R_i)$ is a score of a kernel function whose input is $(Z, R_i)$ where, for each respective cellular constituent abundance value $z_i$ in Z, the respective cellular constituent abundance value $z_i$ is matched to the corresponding cellular constituent abundance value $r_{ik}$ in $R_i$;

$s(Z, R_j)$ is a score of a kernel function whose input is $(Z, R_j)$ where, for each respective cellular constituent abundance value $z_j$ in Z, the respective cellular constituent abundance value $z_j$ is matched to the corresponding cellular constituent abundance value $r_{jk}$ in $R_j$;

b is a bias term;

$w'_i$ is a weight associated with $R_i$; and $w''_j$ is a weight associated with $R_{jj}$; and wherein $W_{pq} = \{w'_i, w''_j, b\}$ The index i is used to individually reference each of the training microarray experiment 46 that have phenotypic characterization $T_p$. So, for example, consider the case in which there are five training microarray experiments 46 and that each respective microarray experiment 46 in the set of five microarray experiments 46 contains abundance values for cellular constituents measured from a different biological specimen that has phenotypic characterization $T_p$. Then, a separate score $s(Z, R_i)$ is computed for each of the five microarray experiments 46 and the index "i" serves to reference each of the five microarray experiments 46 as follows:

$$\sum_{R_i \in T_p} w'_i s(Z, R_i) = \sum_{R_i \in 5} w'_{pi} s(Z, R_i) =$$

$$w'_{p1} s(Z, R_1) + w'_{p2} s(Z, R_2) + w'_{p3} s(Z, R_3) + w'_{p4} s(Z, R_4) + w'_{p5} s(Z, R_5).$$

In some embodiments, the larger the score $s(Z, R_i)$, the more similar the input sample Z is to the training sample $Y_i$. In some embodiments, a positive score $s(Z, R_i)$ indicates molecular similarity between Z and $T_p$ and a negative score $s(Z, R_i)$ indicates similarity between Z and $T_q$.

Furthermore, here, $R_j = \{r_{j1}, \ldots, r_{jn}\}$ is the set of n cellular constituent abundance values for a plurality of cellular constituents measured from a sample j from a training population. In other words, $R_j = \{r_{j1}, \ldots, r_{jn}\}$ are the cellular constituent abundance values 50 for a particular training microarray experiment 46 that has a phenotypic characterization 48 that is $T_q$. This means that the cellular constituent abundance values 50 for the particular training microarray experiment 46 where measured from a sample j that has phenotypic characterization $T_q$ or is from a member of a species that has phenotypic characterization $T_q$. Note that, in preferred embodiments, $R_j = \{r_{j1}, \ldots, r_{jn}\}$ is the set of n cellular constituent abundance values for a plurality of cellular constituents measured from a single sample j from a training population. Training microarray experiment data store 44 may contain other training micorarray experiments 46 that were measured from biological samples that also have phenotypic characterization $T_p$. The index j is used to individually reference each of these training microarray experiments 46. So, for example, consider the case in which there are five training micorarray experiments 46 and that each respective microarray experiment 46 in the set of five microarray experiments 46 contains abundance values for cellular constituents measured from a different biological specimen that has phenotypic characterization $T_q$. Then, a separate score $s(Z, R_i)$ is computed for each of the five microarray experiments 46 and the index "j" serves to reference each of the five microarray experiments 46 as follows:

$$\sum_{R_j \in T_q} w'_i s(Z, R_j) = \sum_{R_j \in 5} w'_i s(Z, R_j) =$$

$$w'_{q1} s(Z, R_1) + w'_{q2} s(Z, R_2) + w'_{q3} s(Z, R_3) + w'_{q4} s(Z, R_4) + w'_{q5} s(Z, R_5).$$

In some embodiments, $s(Z, R_i)$ is equal to the value of the kernel function $e^{(-\gamma[(z_1-r_{i1})^2+(z_2-r_{i2})^2+\ldots (z_n-r_{in})^2])}$, where $z_1, \ldots, z_n$ are cellular constituent abundance values in Z that respectively correspond to cellular constituent abundance values $r_{i1}, \ldots, r_{in}$ in $R_i$; and where $s(Z, R_j)$ is equal to the value of the kernel function $e^{(-\gamma[(z_1-r_{j1})^2+(z_2-r_{j2})^2+\ldots (z_n-r_{jn})^2])}$, where $z_1, \ldots, z_n$ are cellular constituent abundance values in Z that respectively correspond to cellular constituent abundance values $r_{j1}, \ldots, r_{jn}$ in $R_j$. In some embodiments, $$g_{pq}(Z, W_{pq}) = \frac{1}{1 + e^{Af(Z, W_{pq})+B}}$$

and where A and B are parameters derived from logistic regression of $s(Z, R_i)$ and the plurality of phenotypic characterizations.

In one embodiment, for a given pair of phenotypic characterizations $T_p$, $T_q$ in the set of $\{T_1, \ldots, T_k\}$ phenotypic characterizations, the following computations are performed. For each given training microarray experiment 46 in the training population data store 44 that has phenotypic characterization $T_p$, a score $s(Z, R_i)$ is computed that equals the value of a kernel function $K(Z, R_i)$, where Z is the cellular constituent abundance values $\{z_1, \ldots, z_n\}$ of the test microarray experiment 64 and $R_i$ is the cellular constituent abundance values $\{r_{i1}, \ldots, r_{in}\}$ of the training microarray experiment 46 from a biological specimen that exhibit phenotypic characterization $T_p$. The kernel function is a function that returns the dot product between the images of two arguments:

$K(X, Y) = \langle \phi(Z), \phi(R) \rangle$ where $\langle Z, R \rangle$ is notation for the dot product. An image $\phi(Z)$ is a projection of a vector of cellular constituent abundance values Z (or R) into a high-dimensional feature space. Advantageously, the dot product in the high-dimensional feature space can be computed without explicitly constructing the images $\phi(Z)$ and $\phi(R)$. In some embodiments, the high-dimensional feature space may have a dimensionality that is infinite. In some embodiments, the kernel function K is the radial basis function:

$K(Z, R) = e^{(-\gamma[(z_1-r_1)^2+(z_2-r_2)^2+\ldots (z_n-r_n)^2])}$.

Thus, in some embodiments, $s(Z, R_i)$ is equal to the value of $e^{(-\gamma[(z_1-r_1)^2+(z_2-r_2)^2+\ldots (z_n-r_n)^2])}$. In some embodiments, rather than using the radial basis function, a linear or polynomial function may be used as the kernel function K. Thus, in such embodiments $s(Z, R_i)$ is equal to the value of the linear or polynomial function.

In some embodiments, an individual similarity score between an input sample and a training sample, for example $s(Z,R_i)$, is based on the ordinary Euclidean distance between the corresponding standardized expression values:

$$s(Z,R_i) = \exp(-y[(z_1-r_1)^2 + (z_2-r_2)^2 + \ldots + (z_n-r_n)^2])$$

where $z_i$ and $r_i$ are respective cellular constituent abundance values (e.g., standardized expression values) in $Z=\{z_1, \ldots, z_n\}$ of the test microarray experiment 64 and the training microarray experiment $R_i=\{r_{i1}, \ldots, r_{in}\}$. The equation for $s(Z, R_i)$ is one example of a kernel function between Z and $R_i$. However, $s(Z, R_i)$ is not limited to the particular kernel function given in the equation. In fact, any $s(Z, R_i)$ that is a kernel function between Z and $R_i$ can be used to compute similarity between Z and $R_i$. In some embodiments, $s(Z, R_i)$ is a linear kernel function. In some embodiments, $s(Z, R_i)$ is polynomial kernel function.

In some embodiments, $p_{pq}(Z)$ for a given pairwise probability function $g_{pq}(Z, W_{pq})$ is computed as:

$$p_{pq}(Z) = \frac{1}{1 + e^{Af(Z, W_{pq}) + B}}$$

where A and B are parameters derived from logistic regression of $g_{pq}(Z, W_{pq})$ and the plurality of phenotypic characterizations. Here, $p_{pq}(Z)$ is the probability that the given score $g_{pq}(Z, W_{pq})$ for the pair of phenotypic characterizations $(T_p, T_q)$ is produced by $T_p$. Conversely, $1 - p_{pq}(Z)$ is the probability that the given score $g_{pq}(Z, W_{pq})$ computed for the pair of phenotypic characterizations $(T_p, T_q)$ is produced by $T_q$.

In optional step 210, the pairwise probability $p_{pq}(Z)$ are converted to a set M of k probabilities, where $M=\{p_1, p_2, \ldots, p_k\}$, wherein each probability $p_j$ in M is a probability for a phenotypic characterization in the set of $\{T_1, \ldots, T_k\}$ phenotypic characterizations that the biological specimen has the phenotypic characterization such that $$\sum_{j=1}^{k} p_j$$

is equal to a predetermined constant; and

In some embodiments, the predetermined constant is the value 1, the value 100, or some other value. In preferred embodiments, the predetermined constant is 1 and values $p_j$ are therefore true probabilities. However, the predetermined constant can be some number other than 1 and values $p_j$ will still convey meaningful information on the likelihood that that the test biological sample has phenotypic characterization i. For example, when the predetermined constant is set to unity, probability $p_1$ measures the likelihood that phenotypic characterization 1 produces cellular constituent abundance values $\{m_1, \ldots, m_n\}$ that are similar to the cellular constituent abundance values $\{z_1, \ldots, z_n\}$ of Z. The higher the probability value $p_j$, the more likely it is that the test biological specimen indeed has phenotypic characterization i. So, in the example, the higher the probability value $p_1$, the more likely it is that the test biological specimen indeed has phenotypic characterization 1.

In some embodiments, the conversion of pairwise probabilities $p_{pq}(Z)$ to probabilities $p_j$ for a phenotypic characterization $T_p$ is based on counting how many times the phenotype $T_p$ wins the pairwise comparisons that involve $T_p$ versus how many times the phenotype $T_p$ loses the pairwise comparisons that involve $T_p$. Consider the following example in which the plurality of phenotypic characterizations supported by the training microarray experiment data store 44 is fifteen cancers of unknown origin one of which is bladder cancer (BL). The fifteen cancers of unknown origin are each examples of phenotypic characterizations. Since there are a total of fifteen different phenotypic characterizations supported by the training microarray experiment data store 44 in this example, there will be a total of fourteen pairwise probabilities $p_{pq}(Z)$ that involve the phenotypic characterization BL. For each pairwise probabilities $p_{pq}(Z)$ involving BL where the probability $p_{pq}(Z)$ is higher than 50 percent for BL, a value of "1" is added to the running count. The process is illustrated in table 1 below.

TABLE 1

Exemplary computation of probability $p_i$ for a phenotypic characterization $T_i$ from pairwise probabilities $p_{pq}(Z)$ that involve $T_p$.

| Tissue of Unknown Origin[†] | Winner | Count | Running Count |
|---|---|---|---|
| BR | BR | 0 | 0 |
| CO | BL | 1 | 1 |
| GA | GA | 0 | 1 |
| GC | BL | 1 | 2 |
| KI | BL | 1 | 3 |
| LI | BL | 1 | 4 |
| LU | LU | 0 | 4 |
| LY | BL | 1 | 5 |
| ME | BL | 1 | 6 |
| OV | OV | 0 | 6 |
| PA | PA | 0 | 6 |
| PR | BL | 1 | 7 |
| SC | SC | 1 | 8 |
| TH | BL | 1 | 9 |

[†] bladder cancer (BL), breast cancer (BR), colorectal cancer (CO), gastric cancer (GA), germ cell cancer (GC), kidney cancer (KI), hepatocellular cancer (LI), non-small cell lung cancer (LU), non-Hodgkin's lymphoma (LY), melanoma (ME), ovarian cancer (OV), pancreatic cancer (PA), prostate cancer (PR), soft tissue sarcoma (SC), thyroid cancer (TH)

In some embodiments, $p_j$ are obtained by minimizing the criterion $f(p_1, p_2, \ldots, p_k)$ over $p_j$, where $f(\ )$ is defined as $$f(p_1, p_2, \ldots, p_k) = \sum_{j=1}^{k} \sum_{v=1, v \neq i}^{k} (p_i P_{T_i, T_v}(Z) - p_j P_{T_v, T_i}(Z))^2$$

subject to the constraints that $\Sigma_{j=1}^{k} p_i = $ a predetermined constant and $p_j \geq 0$. In some embodiments, the predetermined constant is 1.

In step 212, one or more pairwise probabilities $p_{pq}$ in P is optionally outputted to a user interface device, a monitor, a computer readable storage medium, or a local or remote computer system when step 210 is not performed. Or, one or more pairwise probabilities $p_{pq}$ in P is optionally displayed when step 210 is not performed. One or more $p_j$ in M and/or one or more pairwise probabilities $p_{pq}$ in P is optionally outputted to a user interface device, a monitor, a computer readable storage medium, or a local or remote computer system when step 210 is performed. Or, one or more $p_j$ in M and/or one or more pairwise probabilities $p_{pq}$ in P is optionally displayed when step 210 is performed.

In some embodiments, a remote computer is any computer other than the computer than runs one or more steps of any of the inventive methods disclosed herein. In some embodiments, a local computer is a computer that runs one or more steps of any of the inventive methods disclosed herein. A remote computer is in electronic communication with a local computer by any wired or wireless means known in the art including, but not limited to, 802.11 compliant wireless signals, the Internet, Ethernet, wide area network, and the like. In some embodiments, a remote source is a remote computer. In some embodiments, a remote source is remote electronic storage media that is electronically accessible by a computer network or other electronic means.

5.2 Exemplary Cell Types

In some embodiments, a phenotypic characterization is a cell type. Exemplary cell types include, but are not limited to, keratinizing epithelial cells such as epidermal keratinocytes (differentiating epidermal cells), epidermal basal cells (stem cells), keratinocytes of fingernails and toenails, nail bed basal cells (stem cells), medullary hair shaft cells, cortical hair shaft cells, cuticular hair shaft cells, cuticular hair root sheath cells, hair root sheath cells of Huxley's layer, hair root sheath cell of Henle's layer, external hair root sheath cells, hair matrix cells (stem cells).

Exemplary cell types further include, but are not limited to, wet stratified barrier epithelial cells such as surface epithelial cells of stratified squamous epithelium of cornea, tongue, oral cavity, esophagus, anal canal, distal urethra and vagina, basal cells (stem cell) of epithelia of cornea, tongue, oral cavity, esophagus, anal canal, distal urethra and vagina, and urinary epithelium cells (lining urinary bladder and urinary ducts).

Exemplary cell types further include, but are not limited to, exocrine secretory epithelial cells such as salivary gland mucous cells (polysaccharide-rich secretion), salivary gland serous cells (glycoprotein enzyme-rich secretion), Von Ebner's gland cells in tongue (washes taste buds), mammary gland cells (milk secretion), lacrimal gland cells (tear secretion), Ceruminous gland cells in ear (wax secretion), Eccrine sweat gland dark cells (glycoprotein secretion), Eccrine sweat gland clear cells (small molecule secretion), Apocrine sweat gland cells (odoriferous secretion, sex-hormone sensitive), Gland of Moll cells in eyelid (specialized sweat gland), Sebaceous gland cells (lipid-rich sebum secretion) Bowman's gland cells in nose (washes olfactory epithelium), Brunner's gland cells in duodenum (enzymes and alkaline mucus), seminal vesicle cells (secretes seminal fluid components, including fructose for swimming sperm), prostate gland cells (secretes seminal fluid components), Bulbourethral gland cells (mucus secretion), Bartholin's gland cells (vaginal lubricant secretion), gland of Littre cells (mucus secretion), Uterus endometrium cells (carbohydrate secretion), isolated goblet cells of respiratory and digestive tracts (mucus secretion), stomach lining mucous cells (mucus secretion), gastric gland zymogenic cells (pepsinogen secretion), gastric gland oxyntic cells (hydrochloric acid secretion), pancreatic acinar cells (bicarbonate and digestive enzyme secretion), Paneth cells of small intestine (lysozyme secretion), type II pneumocytes of lung (surfactant secretion), and Clara cells of lung.

Exemplary cell types further include, but are not limited to, hormone secreting cells such as anterior pituitary cells (somatotropes, lactotropes, thyrotropes, gonadotropes, corticotropes), intermediate pituitary cells (secreting melanocyte-stimulating hormone), magnocellular neurosecretory cells (secreting oxytocin, secreting vasopressin), gut and respiratory tract cells secreting serotonin (secreting endorphin, secreting somatostatin, secreting gastrin, secreting secretin, secreting cholecystokinin, secreting insulin, secreting glucagons, secreting bombesin), thyroid gland cells (thyroid epithelial cells, parafollicular cells), parathyroid gland cells (parathyroid chief cells, oxyphil cells), adrenal gland cells (chromaffin cells, secreting steroid hormones), Leydig cells of testes secreting testosterone, Theca interna cells of ovarian follicle secreting estrogen, Corpus luteum cells of ruptured ovarian follicle secreting progesterone, kidney juxtaglomerular apparatus cells (renin secretion), macula densa cells of kidney, peripolar cells of kidney, and mesangial cells of kidney.

Exemplary cell types further include, but are not limited to, gut, exocrine glands and urogenital tract cells such as intestinal brush border cells (with microvilli), exocrine gland striated duct cells, gall bladder epithelial cells, kidney proximal tubule brush border cells, kidney distal tubule cells, ductulus efferens nonciliated cells, epididymal principal cells, and epididymal basal cells.

Exemplary cell types further include, but are not limited to, metabolism and storage cells such as hepatocytes (liver cells), white fat cells, brown fat cells, and liver lipocytes. Exemplary cell types further include, but are not limited to, barrier function cells (lung, gut, exocrine glands and urogenital tract) such as type I pneumocytes (lining air space of lung), pancreatic duct cells (centroacinar cell), nonstriated duct cells (of sweat gland, salivary gland, mammary gland, etc.), kidney glomerulus parietal cells, kidney glomerulus podocytes, loop of Henle thin segment cells (in kidney), kidney collecting duct cells, and duct cells (of seminal vesicle, prostate gland, etc.).

Exemplary cell types further include, but are not limited to, epithelial cells lining closed internal body cavities such as blood vessel and lymphatic vascular endothelial fenestrated cells, blood vessel and lymphatic vascular endothelial continuous cells, blood vessel and lymphatic vascular endothelial splenic cells, synovial cells (lining joint cavities, hyaluronic acid secretion), serosal cells (lining peritoneal, pleural, and pericardial cavities), squamous cells (lining perilymphatic space of ear), squamous cells (lining endolymphatic space of ear), columnar cells of endolymphatic sac with microvilli (lining endolymphatic space of ear), columnar cells of endolymphatic sac without microvilli (lining endolymphatic space of ear), dark cells (lining endolymphatic space of ear), vestibular membrane cells (lining endolymphatic space of ear), stria vascularis basal cells (lining endolymphatic space of ear), stria vascularis marginal cells (lining endolymphatic space of ear), cells of Claudius (lining endolymphatic space of ear), cells of Boettcher (lining endolymphatic space of ear), Choroid plexus cells (cerebrospinal fluid secretion), pia-arachnoid squamous cells, pigmented ciliary epithelium cells of eye, nonpigmented ciliary epithelium cells of eye, and corneal endothelial cells Exemplary cell types further include, but are not limited to, ciliated cells with propulsive function such as respiratory tract ciliated cells, oviduct ciliated cells (in female), uterine endometrial ciliated cells (in female), rete testis cilated cells (in male), ductulus efferens ciliated cells (in male), and ciliated ependymal cells of central nervous system (lining brain cavities).

Exemplary cell types further include, but are not limited to, extracellular matrix secretion cells such as ameloblast epithelial cells (tooth enamel secretion), planum semilunatum epithelial cells of vestibular apparatus of ear (proteoglycan secretion), organ of Corti interdental epithelial cells (secreting tectorial membrane covering hair cells) loose connective tissue fibroblasts, corneal fibroblasts, tendon fibroblasts, bone marrow reticular tissue fibroblasts, pericytes, nucleus pulposus cells of intervertebral disc, cementoblast/cementocytes (tooth root bonelike cementum secretion), odontoblast/odontocyte (tooth dentin secretion), hyaline cartilage chondrocytes fibrocartilage chondrocytes, elastic cartilage chondrocytes, osteoblasts/osteocytes, osteoprogenitor cells (stem cell of osteoblasts), hyalocyte of vitreous body of eye, and stellate cells of perilymphatic space of ear.

Exemplary cell types further include, but are not limited to, contractile cells such as red skeletal muscle cells (slow), white skeletal muscle cells (fast), intermediate skeletal muscle cells, nuclear bag cells of Muscle spindle, nuclear chain cells of Muscle spindle, satellite cells (stem cell), ordinary heart muscle cells, nodal heart muscle cells, purkinje fiber cells, smooth muscle cells (various types), myoepithelial cells of iris, myoepithelial cells of exocrine glands, and red blood cells.

Exemplary cell types further include, but are not limited to, blood and immune system cells such as erythrocytes (red blood cell), megakaryocytes (platelet precursor), monocytes, connective tissue macrophages (various types), epidermal Langerhans cells, osteoclasts (in bone), dendritic cells (in lymphoid tissues), microglial cells (in central nervous system), neutrophil granulocytes, eosinophil granulocytes, basophil granulocytes, mast cells, helper T cells, suppressor T cells, cytotoxic T cells, B cells, natural killer cells, and reticulocytes.

Exemplary cell types further include, but are not limited to, sensory transducer cells such as auditory inner hair cells of organ of Corti, auditory outer hair cells of organ of Corti, basal cells of olfactory epithelium (stem cell for olfactory neurons), cold-sensitive primary sensory neurons, heat-sensitive primary sensory neurons, merkel cell of epidermis (touch sensor), olfactory receptor neurons, photoreceptor rod cell of eyes, photoreceptor blue-sensitive cone cells of eye, photoreceptor green-sensitive cone cells of eye, photoreceptor red-sensitive cone cells of eye, type I carotid body cells (blood pH sensor), Type II carotid body cells (blood pH sensor), type I hair cells of vestibular apparatus of ear (acceleration and gravity), type II hair cells of vestibular apparatus of ear (acceleration and gravity), and type I taste bud cells.

Exemplary cell types further include, but are not limited to, autonomic neuron cells such as cholinergic neural cells, adrenergic neural cells, and peptidergic neural cells. Exemplary cell types further include, but are not limited to, sense organ and peripheral neuron supporting cells such as inner pillar cells of organ of Corti, outer pillar cells of organ of Corti, inner phalangeal cells of organ of Corti, outer phalangeal cells of organ of Corti, border cells of organ of Corti, Hensen cells of organ of Corti, vestibular apparatus supporting cells, type I taste bud supporting cells, olfactory epithelium supporting cells, Schwann cells, satellite cells (encapsulating peripheral nerve cell bodies), and enteric glial cells.

Exemplary cell types further include, but are not limited to, central nervous system neurons and glial cells such as astrocytes, neuron cells, oligodendrocytes, and spindle neurons. Exemplary cell types further include, but are not limited to, lens cells such as anterior lens epithelial cells, crystallin-containing lens fiber cells, and karan cells. Exemplary cell types further include, but are not limited to, pigment cells such as melanocytes and retinal pigmented epithelial cells. Exemplary cell types further include, but are not limited to, germ cells such as oogoniums/oocytes, spermatids, spermatocytes, spermatogonium cells, (stem cell for spermatocyte), and spermatozoon. Exemplary cell types further include, but are not limited to, nurse cells such as ovarian follicle cells, sertoli cells (in testis), and thymus epithelial cells. For more reference on cell types see Freitas Jr., 1999, *Nanomedicine*, Volume I: Basic Capabilities, Landes Bioscience, Georgetown, Tex.

5.3 Exemplary Disease States

Some embodiments of the present invention contain training and/or test microarray experiments for one or more phenotypic characterizations, where the phenotypic characterization is disease state. As used herein, the term "disease state" refers to the absence, presence, or stage of disease in a biological specimen and or a subject from which the biological specimen was obtained. Exemplary diseases include, but are not limited to, asthma, ataxia telangiectasia (Jaspers and Bootsma, 1982, *Proc. Natl. Acad. Sci. U.S.A.* 79: 2641), bipolar disorder, a cancer, common late-onset Alzheimer's disease, diabetes, heart disease, hereditary early-onset Alzheimer's disease (George-Hyslop et al., 1990, *Nature* 347: 194), hereditary nonpolyposis colon cancer, hypertension, infection, maturity-onset diabetes of the young (Barbosa et al., 1976, *Diabete Metab.* 2: 160), mellitus, migraine, nonalcoholic fatty liver (NAFL) (Younossi, et al., 2002, Hepatology 35, 746-752), nonalcoholic steatohepatitis (NASH) (James & Day, 1998, *J. Hepatol.* 29: 495-501), non-insulin-dependent diabetes mellitus, obesity, polycystic kidney disease (Reeders et al., 1987, *Human Genetics* 76: 348), psoriases, schizophrenia, steatohepatitis and xeroderma pigmentosum (De Weerd-Kastelein, *Nat. New Biol.* 238: 80). Genetic heterogeneity hampers genetic mapping, because a chromosomal region may cosegregate with a disease in some families but not in others.

Auto-immune and immune disease states include, but are not limited to, Addison's disease, ankylosing spondylitis, antiphospholipid syndrome, Barth syndrome, Graves' Disease, hemolytic anemia, IgA nephropathy, lupus erythematosus, microscopic polyangiitis, multiple sclerosis, myasthenia gravis, myositis, osteoporosis, pemphigus, psoriasis, rheumatoid arthritis, sarcoidosis, scleroderma, and Sjogren's syndrome. Cardiology disease states include, but are not limited to, arrhythmia, cardiomyopathy, coronary artery disease, angina pectoris, and pericarditis.

Cancers addressed by the systems and the methods of the present invention include, but are not limited to, sarcoma or carcinoma. Examples of such cancers include, but are not limited to, fibrosarcoma, myxosarcoma, liposarcoma, chondrosarcoma, osteogenic sarcoma, chordoma, angiosarcoma, endotheliosarcoma, lymphangiosarcoma, lymphangioendotheliosarcoma, synovioma, mesothelioma, Ewing's tumor, leiomyosarcoma, rhabdomyosarcoma, colon carcinoma, pancreatic cancer, breast cancer, ovarian cancer, prostate cancer, squamous cell carcinoma, basal cell carcinoma, adenocarcinoma, sweat gland carcinoma, sebaceous gland carcinoma, papillary carcinoma, papillary adenocarcinomas, cystadenocarcinoma, medullary carcinoma, bronchogenic carcinoma, renal cell carcinoma, hepatoma, bile duct carcinoma, choriocarcinoma, seminoma, embryonal carcinoma, Wilms' tumor, cervical cancer, testicular tumor, lung carcinoma, small cell lung carcinoma, bladder carcinoma, epithelial carcinoma, glioma, astrocytoma, medulloblastoma, craniopharyngioma, ependymoma, pinealoma, hemangioblastoma, acoustic neuroma, oligodendroglioma, meningioma, melanoma, neuroblastoma, retinoblastoma, leukemia, lymphoma, multiple myeloma, Waldenstrom's macroglobulinemia, and heavy chain disease.

5.4 Exemplary Preprocessing Routines

Optionally, a number of different preprocessing routines can be performed by preprocessing module 60 to prepare training microarray experiments 46 and/or test microarray experiment 64 for use in the methods disclosed above in conjunction with FIG. 2. Some such preprocessing protocols are described in this section. Typically, the preprocessing comprises normalizing the cellular constituent abundance measurement of each cellular constituent in a plurality of cellular constituents that is measured in a biological sample. Many of the preprocessing protocols described in this section are used to normalize microarray data and are called normalization protocols. It will be appreciated that there are many other suitable normalization protocols that may be used in accordance with the present invention. All such protocols are within the scope of the present invention. Many of the normalization protocols found in this section are found in publicly available software, such as Microarray Explorer (Image Processing Section, Laboratory of Experimental and Computational Biology, National Cancer Institute, Frederick, Md. 21702, USA).

One normalization protocol is Z-score of intensity. In this protocol, cellular constituent abundance values are normalized by the (mean intensity)/(standard deviation) of raw intensities for all spots in a sample. For microarray data, the Z-score of intensity method normalizes each hybridized sample by the mean and standard deviation of the raw intensities for all of the spots in that sample. The mean intensity $mnI_i$ and the standard deviation $sdI_i$ are computed for the raw intensity of control genes. It is useful for standardizing the mean (to 0.0) and the range of data between hybridized samples to about −3.0 to +3.0. When using the Z-score, the Z differences ($Z_{diff}$) are computed rather than ratios. The Z-score intensity (Z-score$_{ij}$) for intensity $I_{ij}$ for probe i (hybridization probe, protein, or other binding entity) and spot j is computed as:

$$\text{Z-score}_{ij}=(I_{ij}-mnI_i)/sdI_i,$$

and $$Zdiff_j(x,y)=\text{Z-score}_{xj}-\text{Z-score}_{yj}$$

where x represents the x channel and y represents the y channel.

Another normalization protocol is the median intensity normalization protocol in which the raw intensities for all spots in each sample are normalized by the median of the raw intensities. For microarray data, the median intensity normalization method normalizes each hybridized sample by the median of the raw intensities of control genes (medianI$_i$) for all of the spots in that sample. Thus, upon normalization by the median intensity normalization method, the raw intensity $I_{ij}$ for probe i and spot j, has the value Im$_{ij}$ where, $$Im_{ij}=(I_{ij}/\text{median}I_i).$$

Another normalization protocol is the log median intensity protocol. In this protocol, raw expression intensities are normalized by the log of the median scaled raw intensities of representative spots for all spots in the sample. For microarray data, the log median intensity method normalizes each hybridized sample by the log of median scaled raw intensities of control genes (medianI$_i$) for all of the spots in that sample. As used herein, control genes are a set of genes that have reproducible accurately measured expression values. The value 1.0 is added to the intensity value to avoid taking the log (0.0) when intensity has zero value. Upon normalization by the median intensity normalization method, the raw intensity $I_{ij}$ for probe i and spot j, has the value Im$_{ij}$ where, $$Im_{ij}=\log(1.0+(I_{ij}/\text{median}I_i)).$$

Yet another normalization protocol is the Z-score standard deviation log of intensity protocol. In this protocol, raw expression intensities are normalized by the mean log intensity (mnLI$_i$) and standard deviation log intensity (sdLI$_i$). For microarray data, the mean log intensity and the standard deviation log intensity is computed for the log of raw intensity of control genes. Then, the Z-score intensity ZlogS$_{ij}$ for probe i and spot j is:

$$ZlogS_{ij}=(\log(I_{ij})-mnLI_i)/sdLI_i.$$

Still another normalization protocol is the Z-score mean absolute deviation of log intensity protocol. In this protocol, raw intensities are normalized by the Z-score of the log intensity using the equation (log(intensity)−mean logarithm)/standard deviation logarithm. For microarray data, the Z-score mean absolute deviation of log intensity protocol normalizes each bound sample by the mean and mean absolute deviation of the logs of the raw intensities for all of the spots in the sample. The mean log intensity mnLI$_i$ and the mean absolute deviation log intensity madLI$_i$ are computed for the log of raw intensity of control genes. Then, the Z-score intensity ZlogA$_{ij}$ for probe i and spot j is:

$$ZlogA_{ij}=(\log(I_{ij})-mnLI_i)-mnLI_i)/madLI_i.$$

Another normalization protocol is the user normalization gene set protocol. In this protocol, raw expression intensities are normalized by the sum of the genes in a user defined gene set in each sample. This method is useful if a subset of genes has been determined to have relatively constant expression across a set of samples. Yet another normalization protocol is the calibration DNA gene set protocol in which each sample is normalized by the sum of calibration DNA genes. As used herein, calibration DNA genes are genes that produce reproducible expression values that are accurately measured. Such genes tend to have the same expression values on each of several different microarrays. The algorithm is the same as user normalization gene set protocol described above, but the set is predefined as the genes flagged as calibration DNA.

Yet another normalization protocol is the ratio median intensity correction protocol. This protocol is useful in embodiments in which a two-color fluorescence labeling and detection scheme is used. In the case where the two fluors in a two-color fluorescence labeling and detection scheme are Cy3 and Cy5, measurements are normalized by multiplying the ratio (Cy3/Cy5) by medianCy5/medianCy3 intensities. If background correction is enabled, measurements are normalized by multiplying the ratio (Cy3/Cy5) by (medianCy5−medianBkgdCy5)/(medianCy3−medianBkgdCy3) where medianBkgd means median background levels.

In some embodiments, intensity background correction is used to normalize measurements. The background intensity data from a spot quantification programs may be used to correct spot intensity. Background may be specified as either a global value or on a per-spot basis. If the array images have low background, then intensity background correction may not be necessary.

An intensity dependent normalization can be implemented in R, a language and environment for statistical computing and graphics. In a specific embodiment, the normalization method uses a lowess( ) scatter plot smoother that can be applied to all or a subgroup of probes on the array. For a description of lowess( ), see, e.g., Becker et al., "The New S Language," Wadsworth and Brooks/Cole (S version), 1988; Ripley, 1996, Pattern Recognition and Neural Networks, Cambridge University Press; and Cleveland, 1979, J. Amer. Statist. Assoc. 74, 829:836, each of which is hereby incorporated by reference in its entirety.

5.5 Transcriptional State Measurements

This section provides some exemplary methods for measuring the expression level of gene products, which are one type of cellular constituent. One of skill in the art will appreciate that this invention is not limited to the following specific measurement methods.

5.5.1 Transcript Assay Using Microarrays

The techniques described in this section are particularly useful for the determination of the expression state or the transcriptional state of a cell or cell type or any other biological sample. These techniques include the provision of polynucleotide probe arrays that can be used to provide simultaneous determination of the expression levels of a plurality of genes. These techniques further provide methods for designing and making such polynucleotide probe arrays.

The expression level of a nucleotide sequence of a gene can be measured by any high throughput technique. However measured, the result is either the absolute or relative amounts of transcripts or response data including, but not limited to, values representing abundances or abundance ratios. Preferably, measurement of the expression profile is made by hybridization to transcript arrays, which are described in this subsection. In one embodiment, "transcript arrays" or "profiling arrays" are used. Transcript arrays can be employed for analyzing the expression profile in a cell sample and especially for measuring the expression profile of a cell sample of a particular tissue type or developmental state or exposed to a drug of interest.

In one embodiment, a molecular profile is an expression profile that is obtained by hybridizing detectably labeled polynucleotides representing the nucleotide sequences in mRNA transcripts present in a cell (e.g., fluorescently labeled cDNA synthesized from total cell mRNA) to a microarray. In some embodiments, a microarray is an array of positionally-addressable binding (e.g., hybridization) sites on a support for representing many of the nucleotide sequences in the genome of a cell or organism, preferably most or almost all of the genes. Each of such binding sites consists of polynucleotide probes bound to the predetermined region on the support. Microarrays can be made in a number of ways, of which several are described herein below. However produced, microarrays share certain characteristics. The arrays are reproducible, allowing multiple copies of a given array to be produced and easily compared with each other.

Preferably, a given binding site or unique set of binding sites in the microarray will specifically bind (e.g., hybridize) to a nucleotide sequence in a single gene from a cell or organism (e.g., to exon of a specific mRNA or a specific cDNA derived therefrom). The microarrays used can include one or more test probes, each of which has a polynucleotide sequence that is complementary to a subsequence of RNA or DNA to be detected. Each probe typically has a different nucleic acid sequence, and the position of each probe on the solid surface of the array is usually known. Indeed, the microarrays are preferably addressable arrays, more preferably positionally addressable arrays. Each probe of the array is preferably located at a known, predetermined position on the solid support so that the identity (e.g., the sequence) of each probe can be determined from its position on the array (e.g., on the support or surface). In some embodiments, the arrays are ordered arrays.

Preferably, the density of probes on a microarray or a set of microarrays is 100 different (e.g., non-identical) probes per 1 $cm^2$ or higher. In some embodiments, a microarray can have at least 550 probes per 1 $cm^2$, at least 1,000 probes per 1 $cm^2$, at least 1,500 probes per 1 $cm^2$ or at least 2,000 probes per 1 $cm^2$. In some embodiments, the microarray is a high density array, preferably having a density of at least 2,500 different probes per 1 $cm^2$. A microarray can contain at least 2,500, at least 5,000, at least 10,000, at least 15,000, at least 20,000, at least 25,000, at least 50,000 or at least 55,000 different (e.g., non-identical) probes.

In one embodiment, the microarray is an array (e.g., a matrix) in which each position represents a discrete binding site for a nucleotide sequence of a transcript encoded by a gene (e.g., for an exon of an mRNA or a cDNA derived therefrom). In such and embodiment, the collection of binding sites on a microarray contains sets of binding sites for a plurality of genes. For example, in various embodiments, a microarray can comprise binding sites for products encoded by fewer than 50% of the genes in the genome of an organism. Alternatively, a microarray can have binding sites for the products encoded by at least 50%, at least 75%, at least 85%, at least 90%, at least 95%, at least 99% or 100% of the genes in the genome of an organism (e.g., human, mammal, rat, mouse, pig, dog, cat, etc.). In other embodiments, a microarray can having binding sites for products encoded by fewer than 50%, by at least 50%, by at least 75%, by at least 85%, by at least 90%, by at least 95%, by at least 99% or by 100% of the genes expressed by a cell of an organism. The binding site can be a DNA or DNA analog to which a particular RNA can specifically hybridize. The DNA or DNA analog can be, e.g., a synthetic oligomer or a gene fragment, e.g. corresponding to an exon.

In some embodiments, a gene or an exon in a gene is represented in the profiling arrays by a set of binding sites comprising probes with different polynucleotides that are complementary to different sequence segments of the gene or the exon. Such polynucleotides are preferably of the length of 15 to 200 bases, more preferably of the length of 20 to 100 bases, most preferably 40-60 bases. In some embodiments, the profiling arrays comprise one probe specific to each target gene or exon. However, if desired, the profiling arrays can contain at least 2, 5, 10, 100, or 1000 or more probes specific to some target genes or exons.

5.5.1.1 Preparing Probes for Microarrays

As noted above, the "probe" to which a particular polynucleotide molecule, such as an exon, specifically hybridizes is a complementary polynucleotide sequence. Preferably one or more probes are selected for each target exon. For example, when a minimum number of probes are to be used for the detection of an exon, the probes normally comprise nucleotide sequences greater than 40 bases in length. Alternatively, when a large set of redundant probes is to be used for an exon, the probes normally comprise nucleotide sequences of 40-60 bases. The probes can also comprise sequences complementary to full length exons. The lengths of exons can range from less than 50 bases to more than 200 bases. Therefore, when a probe length longer than exon is to be used, it is preferable to augment the exon sequence with adjacent constitutively spliced exon sequences such that the probe sequence is complementary to the continuous mRNA fragment that contains the target exon. This will allow comparable hybridization stringency among the probes of an exon profiling array. It will be understood that each probe sequence may also comprise linker sequences in addition to the sequence that is complementary to its target sequence.

In some embodiments, the probes may comprise DNA or DNA "mimics" (e.g., derivatives and analogues) corresponding to a portion of each exon of each gene in an organism's genome. In one embodiment, the probes of the microarray are complementary RNA or RNA mimics. DNA mimics are polymers composed of subunits capable of specific, Watson-Crick-like hybridization with DNA, or of specific hybridization with RNA. The nucleic acids can be modified at the base moiety, at the sugar moiety, or at the phosphate backbone. Exemplary DNA mimics include, e.g., phosphorothioates. DNA can be obtained, e.g., by polymerase chain reaction (PCR) amplification of exon segments from genomic DNA, cDNA (e.g., by RT-PCR), or cloned sequences. PCR primers are preferably chosen based on known sequence of the exons or cDNA that result in amplification of unique fragments (e.g., fragments that do not share more than 10 bases of contiguous identical sequence with any other fragment on the microarray). Computer programs that are well known in the art are useful in the design of primers with the required specificity and optimal amplification properties, such as Oligo version 5.0 (National Biosciences). Typically each probe on the microarray will be between 20 bases and 600 bases, and usually between 30 and 200 bases in length. PCR methods are well known in the art, and are described, for example, in Innis et al., eds., 1990, *PCR Protocols: A Guide to Methods and Applications*, Academic Press Inc., San Diego, Calif. It will be apparent to one skilled in the art that controlled robotic systems are useful for isolating and amplifying nucleic acids.

An alternative means for generating the polynucleotide probes of the microarray is by synthesis of synthetic polynucleotides or oligonucleotides, e.g., using N-phosphonate or phosphoramidite chemistries (Froehler et al., 1986, *Nucleic Acid Res.* 14:5399-5407; McBride et al., 1983, *Tetrahedron Lett.* 24:246-248). Synthetic sequences are typically between 10 and 600 bases in length, more typically between 20 and 100 bases in length. In some embodiments, synthetic nucleic acids include non-natural bases, such as, but by no means limited to, inosine. As noted above, nucleic acid analogues may be used as binding sites for hybridization. An example of a suitable nucleic acid analogue is peptide nucleic acid (see, e.g., Egholm et al., 1993, *Nature* 363:566-568; and U.S. Pat. No. 5,539,083).

In alternative embodiments, the hybridization sites (e.g., the probes) are made from plasmid or phage clones of genes, cDNAs (e.g., expressed sequence tags), or inserts therefrom (Nguyen et al., 1995, *Genomics* 29:207-209).

5.5.1.2 Attaching Nucleic Acids to the Solid Surface

Preformed polynucleotide probes can be deposited on a support to form the array. Alternatively, polynucleotide probes can be synthesized directly on the support to form the array. The probes are attached to a solid support or surface, which may be made, e.g., from glass, plastic (e.g., polypropylene, nylon), polyacrylamide, nitrocellulose, gel, or other porous or nonporous material.

One method for attaching the nucleic acids to a surface is by printing on glass plates, as is described generally by Schena et al, 1995, *Science* 270:467-470. This method is especially useful for preparing microarrays of cDNA (See also, DeRisi et al, 1996, *Nature Genetics* 14:457-460; Shalon et al., 1996, *Genome Res.* 6:639-645; and Schena et al., 1995, *Proc. Natl. Acad. Sci. U.S.A.* 93:10539-11286).

A second method for making microarrays is by making high-density polynucleotide arrays. Techniques are known for producing arrays containing thousands of oligonucleotides complementary to defined sequences, at defined locations on a surface using photolithographic techniques for synthesis in situ (see, Fodor et al., 1991, *Science* 251:767-773; Pease et al., 1994, *Proc. Natl. Acad. Sci. U.S.A.* 91:5022-5026; Lockhart et al., 1996, *Nature Biotechnology* 14:1675; U.S. Pat. Nos. 5,578,832; 5,556,752; and 5,510,270) or other methods for rapid synthesis and deposition of defined oligonucleotides (Blanchard et al., *Biosensors & Bioelectronics* 11:687-690). When these methods are used, oligonucleotides (e.g., 60-mers) of known sequence are synthesized directly on a surface such as a derivatized glass slide. The array produced can be redundant, with several polynucleotide molecules per exon.

Other methods for making microarrays, e.g., by masking (Maskos and Southern, 1992, *Nucl. Acids. Res.* 20:1679-1684), may also be used. In principle, and as noted supra, any type of array, for example, dot blots on a nylon hybridization membrane (see Sambrook et al., supra) could be used.

In one embodiment, microarrays are manufactured by means of an ink jet printing device for oligonucleotide synthesis, e.g., using the methods and systems described by Blanchard in International Patent Publication No. WO 98/41531, published Sep. 24, 1998; Blanchard et al., 1996, *Biosensors and Bioelectronics* 11:687-690; Blanchard, 1998, in *Synthetic DNA Arrays in Genetic Engineering*, Vol. 20, J. K. Setlow, Ed., Plenum Press, New York at pages 111-123; and U.S. Pat. No. 6,028,189 to Blanchard. Specifically, the polynucleotide probes in such microarrays can be synthesized in arrays, e.g., on a glass slide, by serially depositing individual nucleotide bases in "microdroplets" of a high surface tension solvent such as propylene carbonate. The microdroplets have small volumes (e.g., 100 pL or less, more preferably 50 pL or less) and are separated from each other on the microarray (e.g., by hydrophobic domains) to form circular surface tension wells which define the locations of the array elements (i.e., the different probes). Polynucleotide probes are normally attached to the surface covalently at the 3N end of the polynucleotide. Alternatively, polynucleotide probes can be attached to the surface covalently at the 5N end of the polynucleotide (see for example, Blanchard, 1998, in *Synthetic DNA Arrays in Genetic Engineering*, Vol. 20, J. K. Setlow, Ed., Plenum Press, New York at pages 111-123).

5.5.1.3 Target Polynucleotide Molecules

Target polynucleotides that can be analyzed include RNA molecules such as, but by no means limited to, messenger RNA (mRNA) molecules, ribosomal RNA (rRNA) molecules, cRNA molecules (i.e., RNA molecules prepared from cDNA molecules that are transcribed in vivo) and fragments thereof. Target polynucleotides that can also be analyzed by the methods of the present invention include, but are not limited to DNA molecules such as genomic DNA molecules, cDNA molecules, and fragments thereof including oligonucleotides, ESTs, STSs, etc.

The target polynucleotides can be from any source. For example, the target polynucleotide molecules can be naturally occurring nucleic acid molecules such as genomic or extragenomic DNA molecules isolated from a patient, or RNA molecules, such as mRNA molecules, isolated from a patient. Alternatively, the polynucleotide molecules can be synthesized, including, e.g., nucleic acid molecules synthesized enzymatically in vivo or in vitro, such as cDNA molecules, or polynucleotide molecules synthesized by PCR, RNA molecules synthesized by in vitro transcription, etc. The sample of target polynucleotides can comprise, e.g., molecules of DNA, RNA, or copolymers of DNA and RNA. In some embodiments, the target polynucleotides will correspond to particular genes or to particular gene transcripts (e.g., to particular mRNA sequences expressed in cells or to particular cDNA sequences derived from such mRNA sequences). However, in many embodiments, the target polynucleotides can correspond to particular fragments of a gene transcript. For example, the target polynucleotides may correspond to different exons of the same gene, e.g., so that different splice variants of the gene can be detected and/or analyzed.

In some embodiments, the target polynucleotides to be analyzed are prepared in vitro from nucleic acids extracted from cells. For example, in one embodiment, RNA is extracted from cells (e.g., total cellular RNA, poly(A)$^+$ messenger RNA, fraction thereof) and messenger RNA is purified from the total extracted RNA. Methods for preparing total and poly(A)$^+$ RNA are well known in the art, and are described generally, e.g., in Sambrook et al., supra. In one embodiment, RNA is extracted from cells of the various types of interest using guanidinium thiocyanate lysis followed by CsCl centrifugation and an oligo dT purification (Chirgwin et al., 1979, Biochemistry 18:5294-5299). In another embodiment, RNA is extracted from cells using guanidinium thiocyanate lysis followed by purification on RNeasy columns (Qiagen). cDNA is then synthesized from the purified mRNA using, e.g., oligo-dT or random primers. In some embodiments, the target polynucleotides are cRNA prepared from purified messenger RNA extracted from cells. As used herein, cRNA is defined here as RNA complementary to the source RNA. The extracted RNAs are amplified using a process in which doubled-stranded cDNAs are synthesized from the RNAs using a primer linked to an RNA polymerase promoter in a direction capable of directing transcription of anti-sense RNA. Anti-sense RNAs or cRNAs are then transcribed from the second strand of the double-stranded cDNAs using an RNA polymerase (see, e.g., U.S. Pat. Nos. 5,891,636, 5,716, 785; 5,545,522 and 6,132,997; see also, U.S. Pat. Nos. 6,271, 002, and 7,229,765. Both oligo-dT primers (U.S. Pat. Nos. 5,545,522 and 6,132,997) or random primers (U.S. Pat. No. 7,229,765) that contain an RNA polymerase promoter or complement thereof can be used. The target polynucleotides can be short and/or fragmented polynucleotide molecules that are representative of the original nucleic acid population of the cell.

The target polynucleotides to be analyzed are typically detectably labeled. For example, cDNA can be labeled directly, e.g., with nucleotide analogs, or indirectly, e.g., by making a second, labeled cDNA strand using the first strand as a template. Alternatively, the double-stranded cDNA can be transcribed into cRNA and labeled.

In some instances, the detectable label is a fluorescent label, e.g., by incorporation of nucleotide analogs. Other labels suitable for use include, but are not limited to, biotin, imminobiotin, antigens, cofactors, dinitrophenol, lipoic acid, olefinic compounds, detectable polypeptides, electron rich molecules, enzymes capable of generating a detectable signal by action upon a substrate, and radioactive isotopes. Some radioactive isotopes include, but are not limited to, $^{32}P$, $^{35}S$, $^{14}C$, $^{15}N$ and $^{125}I$. Fluorescent molecules include, but are not limited to, fluorescein and its derivatives, rhodamine and its derivatives, texas red, 5Ncarboxy-fluorescein ("FMA"), 2N,7N-dimethoxy-4N,5N-dichloro-6-carboxy-fluorescein ("JOE"), N,N,NN,NN-tetramethyl-6-carboxy-rhodamine ("TAMRA"), 6Ncarboxy-X-rhodamine ("ROX"), HEX, TET, IRD40, and IRD41. Fluorescent molecules further include: cyamine dyes, including by not limited to Cy3, Cy3.5 and Cy5; BODIPY dyes including but not limited to BODIPY-FL, BODIPY-TR, BODIPY-TMR, BODIPY-630/650, and BODIPY-650/670; and ALEXA dyes, including but not limited to ALEXA-488, ALEXA-532, ALEXA-546, ALEXA-568, and ALEXA-594; as well as other fluorescent dyes which will be known to those who are skilled in the art. Electron rich indicator molecules suitable, but are not limited to, ferritin, hemocyanin, and colloidal gold. Alternatively, in some embodiments the target polynucleotides may be labeled by specifically complexing a first group to the polynucleotide. A second group, covalently linked to an indicator molecules and which has an affinity for the first group, can be used to indirectly detect the target polynucleotide. In such an embodiment, compounds suitable for use as a first group include, but are not limited to, biotin and iminobiotin. Compounds suitable for use as a second group include, but are not limited to, avidin and streptavidin.

5.5.1.4 Hybridization to Microarrays

As described supra, nucleic acid hybridization and wash conditions are chosen so that the polynucleotide molecules to be analyzed (referred to herein as the "target polynucleotide molecules) specifically bind or specifically hybridize to the complementary polynucleotide sequences of the array, preferably to a specific array site, where its complementary DNA is located.

Arrays containing double-stranded probe DNA situated thereon are preferably subjected to denaturing conditions to render the DNA single-stranded prior to contacting with the target polynucleotide molecules. Arrays containing single-stranded probe DNA (e.g., synthetic oligodeoxyribonucleic acids) may need to be denatured prior to contacting with the target polynucleotide molecules, e.g., to remove hairpins or dimers which form due to self complementary sequences.

Optimal hybridization conditions will depend on the length (e.g., oligomer versus polynucleotide greater than 200 bases) and type (e.g., RNA, or DNA) of probe and target nucleic acids. General parameters for specific (e.g., stringent) hybridization conditions for nucleic acids are described in Sambrook et al., (supra), and in Ausubel et al., 1987, Current Protocols in Molecular Biology, Greene Publishing and Wiley-Interscience, New York. When the cDNA microarrays of Schena et al. are used, typical hybridization conditions are hybridization in 5×SSC plus 0.2% SDS at 65° C. for four hours, followed by washes at 25° C. in low stringency wash buffer (1×SSC plus 0.2% SDS), followed by 10 minutes at 25° C. in higher stringency wash buffer (0.1×SSC plus 0.2% SDS) (Shena et al., 1996, Proc. Natl. Acad. Sci. U.S.A. 93:10614). Useful hybridization conditions are also provided in, e.g., Tijessen, 1993, Hybridization with Nucleic Acid Probes, Elsevier Science Publishers B. V. and Kricka, 1992, Nonisotopic DNA Probe Techniques, Academic Press, San Diego, Calif.

Exemplary hybridization conditions for use with the screening and/or signaling chips include hybridization at a temperature at or near the mean melting temperature of the probes (e.g., within 5° C., more preferably within 2° C.) in 1 M NaCl, 50 mM MES buffer (pH 6.5), 0.5% sodium Sarcosine and 30% formamide.

5.5.1.5 Signal Detection and Data Analysis

It will be appreciated that when target sequences, e.g., cDNA or cRNA, complementary to the RNA of a cell is made and hybridized to a microarray under suitable hybridization conditions, the level of hybridization to the site in the array corresponding to an exon of any particular gene will reflect the prevalence in the cell of mRNA or mRNAs containing the exon transcribed from that gene. For example, when detectably labeled (e.g., with a fluorophore) cDNA complementary to the total cellular mRNA is hybridized to a microarray, the site on the array corresponding to an exon of a gene (e.g., capable of specifically binding the product or products of the gene expressing) that is not transcribed or is removed during RNA splicing in the cell will have little or no signal (e.g., fluorescent signal), and an exon of a gene for which the encoded mRNA expressing the exon is prevalent will have a relatively strong signal.

When fluorescently labeled probes are used, the fluorescence emissions at each site of a transcript array can be, preferably, detected by scanning confocal laser microscopy. In one embodiment, a separate scan, using the appropriate excitation line, is carried out for each of two fluorophores used in such embodiments. Alternatively, a laser can be used that allows simultaneous specimen illumination at wavelengths specific to the two fluorophores and emissions from the two fluorophores can be analyzed simultaneously (see Shalon et al., 1996, *Genome Res.* 6:639-645). In some embodiments, the arrays are scanned with a laser fluorescence scanner with a computer controlled X-Y stage and a microscope objective. Sequential excitation of the two fluorophores is achieved with a multi-line, mixed gas laser, and the emitted light is split by wavelength and detected with two photomultiplier tubes. Such fluorescence laser scanning devices are described, e.g., in Schena et al., 1996, *Genome Res.* 6:639-645. Alternatively, the fiber-optic bundle described by Ferguson et al., 1996, *Nature Biotech.* 14:1681-1684, can be used to monitor mRNA abundance levels at a large number of sites simultaneously.

Signals are recorded and, in a preferred embodiment, analyzed by computer. In one embodiment, the scanned image is despeckled using a graphics program (e.g., Hijaak Graphics Suite) and then analyzed using an image gridding program that creates a spreadsheet of the average hybridization at each wavelength at each site. If necessary, an experimentally determined correction for "cross talk" (or overlap) between the channels for the two fluors can be made. For any particular hybridization site on the transcript array, a ratio of the emission of the two fluorophores can be calculated. The ratio is independent of the absolute expression level of the cognate gene, but is useful for genes whose expression is significantly modulated by drug administration, gene deletion, or any other tested event.

5.6 Apparatus, Computer and Computer Program Product Implementations

The present invention can be implemented as a computer program product that comprises a computer program mechanism embedded in a computer-readable storage medium. Further, any of the methods of the present invention can be implemented in one or more computers or other forms of apparatus. Examples of apparatus include but are not limited to, a computer, and a spectroscopic measuring device (e.g., a microarray reader or microarray scanner). Further still, any of the methods of the present invention can be implemented in one or more computer program products. Some embodiments of the present invention provide a computer program product that encodes any or all of the methods disclosed herein. Such methods can be stored on a CD-ROM, DVD, magnetic disk storage product, or any other computer-readable data or program storage product. Such methods can also be embedded in permanent storage, such as ROM, one or more programmable chips, or one or more application specific integrated circuits (ASICs). Such permanent storage can be localized in a server, 802.11 access point, 802.11 wireless bridge/station, repeater, router, mobile phone, or other electronic devices. Such methods encoded in the computer program product can also be distributed electronically, via the Internet or otherwise, by transmission of a computer data signal (in which the software modules are embedded) either digitally or on a carrier wave.

Some embodiments of the present invention provide a computer program product that contains any or all of the program modules shown in FIG. 1. These program modules can be stored on a CD-ROM, DVD, magnetic disk storage product, or any other computer-readable data or program storage product. The program modules can also be embedded in permanent storage, such as ROM, one or more programmable chips, or one or more application specific integrated circuits (ASICs). Such permanent storage can be localized in a server, 802.11 access point, 802.11 wireless bridge/station, repeater, router, mobile phone, or other electronic devices. The software modules in the computer program product can also be distributed electronically, via the Internet or otherwise, by transmission of a computer data signal (in which the software modules are embedded) either digitally or on a carrier wave.

5.7 Exemplary Embodiments

Provided hereinbelow are nonlimiting examples in accordance with various aspect of the present invention.

Embodiment 1

A method of determining, for each respective phenotypic characterization in a plurality k of phenotypic characterizations, a probability that a test biological specimen has the respective phenotypic characterization, the method comprising:

(A) computing, for each respective pair of phenotypic characterizations (T1, T2) in phenotypic characterization pairs formed from phenotypic characterizations in the plurality of phenotypic characterizations, a decision function having a score f(X), wherein $$f(X) = \sum_{Y_i \in T1} w'_i s(X, Y_i) - \sum_{Y_j \in T2} w''_j s(X, Y_j) + b$$

and wherein
- $Y_i = \{y_{i1}, \ldots, y_{in}\}$ is the set of n cellular constituent abundance values for a first plurality of cellular constituents measured from a sample i, from a training population, wherein sample i has phenotypic characterization T1 in the plurality of phenotypic characterizations;
- $Y_j = \{y_{j1}, \ldots, y_{jn}\}$ is the set of n cellular constituent abundance values for a second plurality of cellular constituents measured from a sample j, from the training population, wherein sample j has phenotypic characterization T2 in the plurality of phenotypic characterizations;
- $X = \{x_1, \ldots, x_n\}$ is the set of n cellular constituent abundance values for a third plurality of cellular constituents measured from the test biological specimen;
- wherein n is at least 1 (e.g., at least 5, at least 10, at least 15, at least 20, at least 25, at least 50, at least 100, or at least 200);
- $s(X, Y_i)$ is a score of a kernel function whose input is $(X, Y_i)$ where, for each respective cellular constituent abundance value $x_i$ in X, the respective cellular constituent abundance value $x_i$ is matched to the corresponding cellular constituent abundance value $y_{ik}$ in $Y_i$;
- $s(X, Y_j)$ is a score of a kernel function whose input is $(X, Y_j)$ where, for each respective cellular constituent abundance value $x_j$ in X, the respective cellular constituent abundance value $x_j$ is matched to the corresponding cellular constituent abundance value $y_{jk}$ in $Y_j$;
- b is a bias term;
- $w'_i$ is a weight associated with $Y_i$; and
- $w''_j$ is a weight associated with $Y_j$;

(B) computing from the score f(X) for each respective pair of phenotypic characterizations (T1, T2) in phenotypic characterization pairs formed from phenotypic characterizations in the plurality of phenotypic characterizations, a respective pairwise probability $p_{ij}(X)$ that the test biological specimen originated from phenotypic characterization T1, thereby forming a plurality of pairwise probabilities $p_{ij}(X)$;

(C) optionally converting the plurality of pairwise probabilities $p_{ij}(X)$ to a set of $\{1, \ldots, k\}$ probabilities, wherein k is 3 or greater, wherein each probability $p_i$ in the set of $\{1, \ldots, k\}$ is a probability for a phenotypic characterization in the plurality of phenotypic characterizations such that $$\sum_{i=1}^{k} p_i \text{ is equal to a predetermined constant;}$$

and (D) optionally outputting one or more pairwise probabilities $p_{ij}(X)$ in the plurality of pairwise probabilities $p_{ij}(X)$ to a user interface device, a monitor, a computer readable storage medium, or a local or remote computer system when step (C) is not performed; or displaying one or more pairwise probabilities $p_{ij}(X)$ in the plurality of pairwise probabilities $p_{ij}(X)$ when step (C) is not performed, or optionally outputting one or more $p_i$ in the set $\{1, \ldots, k\}$ and/or one or more pairwise probabilities $p_{ij}(X)$ in the plurality of pairwise probabilities $p_{ij}(X)$ to a user interface device, a monitor, a computer readable storage medium, or a local or remote computer system when step (C) is performed; or displaying one or more $p_i$ in the set $\{1, \ldots, k\}$ or one or more pairwise probabilities $p_{ij}(X)$ in the plurality of pairwise probabilities $p_{ij}(X)$ when step (C) is performed.

Embodiment 2

The method of embodiment 1, wherein $s(X, Y_i)$ is equal to the value of the kernel function $e^{(-\gamma[(x_1-y_{i1})^2+(x_2-y_{i2})^2+\ldots (x_n-y_{in})^2])}$, wherein $x_1, \ldots, x_n$ are cellular constituent abundance values in X that respectively correspond to cellular constituent abundance values $y_{i1}, \ldots, y_{in}$ in $Y_i$; and wherein $s(X, Y_j)$ is equal to the value of the kernel function $e^{(-\gamma[(x_1-y_{j1})^2+(x_2-y_{j2})^2+\ldots (x_n-y_{jn})^2])}$, wherein $x_1, \ldots, x_n$ are cellular constituent abundance values in X that respectively correspond to cellular constituent abundance values $y_{j1}, \ldots, y_{jn}$ in $Y_j$.

Embodiment 3

The method of embodiment 1 or 2, the method further comprising determining values, for a given pair of phenotypic computations (T1, T2), for the set of weights $w'_i$s, $w''_j$, and b used in the decision function with score f(X) before the computing step (A) by subjecting each set of cellular constituent abundance values in the training population that were measured from samples that have phenotypic characterization T1 or T2 to a support vector machine.

Embodiment 4

The method of any one of embodiments 1-3, wherein $$p_{ij}(X) = \frac{1}{1 + e^{Af(X)+B}}$$

and wherein A and B are parameters derived from logistic regression of s(X) and the plurality of phenotypic characterizations.

Embodiment 5

The method of any one of embodiments 1-4, wherein a phenotypic characterization in the plurality of phenotypic characterizations is an organ type, an abnormal state in an organ, an tissue type, an abnormal state in a tissue, a cell type, an abnormal cell type, a cell morphology, an abnormal cell morphology, a disease state, a disease prognosis, or a therapeutic response.

Embodiment 6

The method of any one of embodiments 1-5, wherein the set of cellular constituent abundance values X for the third plurality of cellular constituents measured from the test biological specimen or the set of cellular constituent abundance values $Y_i$ for the first plurality of cellular constituents measured from the sample i are measured from a microarray comprising probes arranged with a density of 100 different probes per 1 $cm^2$ or higher.

Embodiment 7

The method of any one of embodiments 1-5, wherein the set of cellular constituent abundance values X for the third plurality of cellular constituents measured from the test biological specimen or the set of cellular constituent abundance values $Y_i$ for the first plurality of cellular constituents measured from the sample i or the set of cellular constituent abundance values $Y_j$ for the second plurality of cellular constituents measured from the sample j are measured from a microarray comprising probes arranged with a density of at least 2,500 different probes per 1 $cm^2$.

Embodiment 8

The method of any one of embodiments 1-7, wherein the set of cellular constituent abundance values X for the third plurality of cellular constituents measured from the test biological specimen or the set of cellular constituent abundance values $Y_i$ for the first plurality of cellular constituents measured from the sample i or the set of cellular constituent abundance values $Y_j$ for the second plurality of cellular constituents measured from the sample j are measured from a microarray comprising at least 10,000 different probes.

Embodiment 9

The method of any one of embodiments 1-8, wherein the set of cellular constituent abundance values X for the third plurality of cellular constituents measured from the test biological specimen or the set of cellular constituent abundance values $Y_i$ for the first plurality of cellular constituents measured from the sample i or the set of cellular constituent abundance values $Y_j$ for the second plurality of cellular constituents measured from the sample j are measured from an expression microarray, a comparative genomic hybridization microarray, an exon microarray, or a microRNA microarray.

Embodiment 10

The method of any one of embodiments 1-9, wherein the first plurality of cellular constituents, the second plurality of cellular constituents, or the third plurality of cellular constituents is measured from a microarray comprising between 10 oligonucleotides and $5 \times 10^6$ oligonucleotides.

Embodiment 11

The method of any one of embodiments 1-10, wherein the first plurality of cellular constituents, the second plurality of cellular constituents or the third plurality of cellular constituents is between 5 mRNA and 50,000 mRNA.

Embodiment 12

The method of any one of embodiments 1-10, wherein the first plurality of cellular constituents, the second plurality of cellular constituents or the third plurality of cellular constituents is between 50 proteins and 200,000 proteins.

Embodiment 13

The method of any one of embodiments 1-12, wherein, for each respective phenotypic characterization in the plurality of phenotypic characterizations, the training population comprises at least three samples that have the respective phenotypic characterization.

Embodiment 14

The method of any one of embodiments 1-13, wherein, for each respective phenotypic characterization in the plurality of phenotypic characterizations, the training population comprises at least ten samples that have the respective phenotypic characterization.

Embodiment 15

The method of any one of embodiments 1-14, wherein the plurality of phenotypic characterizations is cancer tissue of origin and wherein the plurality of phenotypic characterizations comprises bladder cancer, breast cancer, colorectal cancer, gastric cancer, germ cell cancer, kidney cancer, hepatocellular cancer, non-small cell lung cancer, non-Hodgkin's lymphoma, melanoma, ovarian cancer, pancreatic cancer, prostate cancer, soft tissue sarcoma, and thyroid cancer.

Embodiment 16

The method of any one of embodiments 1-15, wherein the plurality k of phenotypic characterizations is between 2 phenotypic characterizations and 100 phenotypic characterizations.

Embodiment 17

The method of any one of embodiments 1-16, wherein the plurality k of phenotypic characterizations is between 10 phenotypic characterizations and 50 phenotypic characterizations.

Embodiment 18

The method of any one of embodiments 1-17, wherein the set of cellular constituent abundance values X are received from a remote source over a computer network and wherein the one or more pairwise probabilities $p_{ij}(X)$ or the one or more $p_i$ are communicated to the remote source over the network.

Embodiment 19

The method of embodiment 18, wherein the remote source is a remote computer.

Embodiment 20

The method of any one of embodiments 1-19, wherein the converting step (C) comprises, for each respective phenotypic characterization i in the k phenotypic characterizations, counting the number of pairwise probabilities $p_{ij}(X)$ in the plurality of pairwise probabilities that includes the respective characterization i and that that deem there to be a greater than fifty percent probability that the test biological specimen has the respective characterization i.

Embodiment 21

An apparatus for determining a phenotypic characterization of a test biological specimen from among a plurality k of phenotypic characterizations, the apparatus comprising:
 a processor; and
 a memory, coupled to the processor, the memory storing a module comprising:
 instructions for performing the steps of any one of embodiments 1 through 20.

Embodiment 22

A computer-readable medium storing a computer program executable by a computer to determine, for each respective phenotypic characterization in a plurality k of phenotypic characterizations, a probability that a test biological specimen has the respective phenotypic characterization, the computer program comprising instructions for performing the steps of any one of embodiments 1 through 20.

Embodiment 23

An apparatus for determining, for each respective phenotypic characterization in a plurality k of phenotypic characterizations, a probability that a test biological specimen has the respective phenotypic characterization, the apparatus comprising:
 a processor; and
 a memory, coupled to the processor, the memory storing a module comprising:
 (A) instructions for computing, for each respective pair of phenotypic characterizations (T1, T2) in phenotypic characterization pairs formed from phenotypic characterizations in the plurality of phenotypic characterizations, a decision function having a score f(X), wherein $$f(X) = \sum_{Y_i \in T1} w'_i s(X, Y_i) - \sum_{Y_j \in T2} w''_j s(X, Y_j) + b$$

and wherein
 $Y_i = \{y_{i1}, \ldots, y_{in}\}$ is the set of n cellular constituent abundance values for a first plurality of cellular constituents measured from a sample i, from a training population, wherein sample i has phenotypic characterization T1 in the plurality of phenotypic characterizations, wherein n is at least 5, at least 10, at least 15, at least 20, at least 25, at least 50, at least 100, or at least 200;

$Y_j = \{y_{j1}, \ldots, y_{jn}\}$ is the set of n cellular constituent abundance values for a second plurality of cellular constituents measured from a sample j, from the training population, wherein sample j has phenotypic characterization T2 in the plurality of phenotypic characterizations;

$X = \{x_1, \ldots, x_n\}$ is the set of n cellular constituent abundance values for a third plurality of cellular constituents measured from the test biological specimen;

wherein n is at least 1; and $s(X, Y_i)$ is a kernel function whose input is $(X, Y_i)$, where, for each respective cellular constituent abundance value $x_i$ in X, the respective cellular constituent abundance value $x_i$ is matched to the corresponding cellular constituent abundance value $y_{ik}$ in $Y_i$;

$s(X, Y_j)$ is a kernel function whose input is $(X, Y_j)$, where, for each respective cellular constituent abundance value $x_j$ in X, the respective cellular constituent abundance value $x_j$ is matched to the corresponding cellular constituent abundance value $y_{jk}$ in $Y_j$;

b is a bias term;

$w'_i$ is a weight associated with $Y_i$; and $w''_j$ is a weight associated with $Y_j$;

(B) instructions for computing from the score f(X) for each respective pair of phenotypic characterizations (T1, T2) in phenotypic characterization pairs formed from phenotypic characterizations in the plurality of phenotypic characterizations, a respective pairwise probability $p_{ij}(X)$ that the test biological specimen originated from phenotypic characterization T1, thereby forming a plurality of pairwise probabilities $p_{ij}(X)$;

(C) optionally, instructions for converting the plurality of pairwise probabilities $p_{ij}(X)$ to a set of $\{1, \ldots, k\}$ probabilities, wherein k is 3 or greater, wherein each probability $p_i$ in the set of $\{1, \ldots, k\}$ probabilities is a probability for a phenotypic characterization in the plurality of phenotypic characterizations such that $$\sum_{i=1}^{k} p_i$$

is equal to a predetermined constant; and (D) optionally, instructions for outputting one or more pairwise probabilities $p_{ij}(X)$ in the plurality of pairwise probabilities $p_{ij}(X)$ to a user interface device, a monitor, a computer readable storage medium, or a local or remote computer system when the instructions for converting are not performed; or displaying one or more pairwise probabilities $p_{ij}(X)$ in the plurality of pairwise probabilities $p_{ij}(X)$ when the instructions for converting are not performed, or optionally, instructions for outputting one or more $p_i$ in the set of $\{1, \ldots, k\}$ probabilities and/or one or more pairwise probabilities $p_{ij}(X)$ in the plurality of pairwise probabilities $p_{ij}(X)$ to a user interface device, a monitor, a computer readable storage medium, or a local or remote computer system when the instructions for converting are performed; or displaying one or more $p_i$ in the set $\{1, \ldots, k\}$ and/or one or more pairwise probabilities $p_{ij}(X)$ in the plurality of pairwise probabilities $p_{ij}(X)$ when the instructions for converting are performed.

Embodiment 24

The apparatus of embodiment 23, wherein the set of cellular constituent abundance values X are received by the apparatus from a remote source over a network and wherein the one or more pairwise probabilities $p_{ij}(X)$ or the one or more $p_i$ are communicated to the remote source over said network.

Embodiment 25

The apparatus of embodiment 23 or 24, wherein the memory further comprises:

a set of cellular constituent abundance values for each sample i in the training population; and an indication of the clinical truth of each sample i in the training population.

Embodiment 26

The apparatus of embodiment 25, wherein the network is the Internet.

Embodiment 27

A computer-readable medium storing a computer program executable by a computer to determine, for each respective phenotypic characterization in a plurality k of phenotypic characterizations, a probability that a test biological specimen has the respective phenotypic characterization, the computer program comprising:

(A) instructions for computing, for each respective pair of phenotypic characterizations (T1, T2) in phenotypic characterization pairs formed from phenotypic characterizations in the plurality of phenotypic characterizations, a decision function having a score f(X), wherein $$f(X) = \sum_{Y_i \in T1} w'_i s(X, Y_i) - \sum_{Y_j \in T2} w''_j s(X, Y_j) + b$$

and wherein $Y_i = \{y_{i1}, \ldots, y_{in}\}$ is the set of n cellular constituent abundance values for a first plurality of cellular constituents measured from a sample i, from a training population, wherein sample i has phenotypic characterization T1 in the plurality of phenotypic characterizations, wherein n is at least 5, at least 10, at least 15, at least 20, at least 25, at least 50, at least 100, or at least 200;

$Y_j = \{y_{j1}, \ldots, y_{jn}\}$ is the set of n cellular constituent abundance values for a second plurality of cellular constituents measured from a sample j, from the training population, wherein sample j has phenotypic characterization T2 in the plurality of phenotypic characterizations;

$X = \{x_1, \ldots, x_n\}$ is the set of n cellular constituent abundance values for a third plurality of cellular constituents measured from the test biological specimen;

$s(X, Y_i)$ is a kernel function whose input is $(X, Y_i)$, where, for each respective cellular constituent abundance value $x_i$ in X, the respective cellular constituent abundance value $x_i$ is matched to the corresponding cellular constituent abundance value $y_{ik}$ in $Y_i$;

$s(X, Y_j)$ is a kernel function whose input is $(X, Y_j)$, where, for each respective cellular constituent abundance value $x_j$ in X, the respective cellular constituent abundance value $x_j$ is matched to the corresponding cellular constituent abundance value $y_{jk}$ in $Y_j$;

b is a bias term;

$w'_i$ is a weight associated with $Y_i$; and $w''_j$ is a weight associated with $Y_j$;

(B) instructions for computing from the score f(X) for each respective pair of phenotypic characterizations (T1, T2) in phenotypic characterization pairs formed from phenotypic characterizations in the plurality of phenotypic characterizations, a respective pairwise probability $p_{ij}(X)$ that the test biological specimen originated from phenotypic characterization T1, thereby forming a plurality of pairwise probabilities $p_{ij}(X)$;

(C) optionally, instructions for converting the plurality of pairwise probabilities $p_{ij}(X)$ to a set of $\{1, \ldots, k\}$ probabilities, wherein each probability $p_i$ in the set of $\{1, \ldots, k\}$ probabilities is a probability for a phenotypic characterization in the plurality of phenotypic characterizations such that $$\sum_{i=1}^{k} p_i$$

is equal to a predetermined constant; and (D) optionally, instructions for outputting one or more pairwise probabilities $p_{ij}(X)$ in the plurality of pairwise probabilities $p_{ij}(X)$ to a user interface device, a monitor, a computer readable storage medium, or a local or remote computer system when the instructions for converting are not performed; or displaying one or more pairwise probabilities $p_{ij}(X)$ in the plurality of pairwise probabilities $p_{ij}(X)$ when the instructions for converting are not performed, or optionally instructions for outputting one or more $p_i$ in the set of $\{1, \ldots, k\}$ probabilities and/or one or more pairwise probabilities $p_{ij}(X)$ in the plurality of pairwise probabilities $p_{ij}(X)$ to a user interface device, a monitor, a computer readable storage medium, or a local or remote computer system when the instructions for converting are performed; or displaying one or more $p_i$ in the set $\{1, \ldots, k\}$ and/or one or more pairwise probabilities $p_{ij}(X)$ in the plurality of pairwise probabilities $p_{ij}(X)$ when the instructions for converting are performed.

5.8 Additional Exemplary Embodiments

Provided hereinbelow are additional nonlimiting examples in accordance with various aspect of the present invention.

Embodiment 101

A method of determining, for each respective phenotypic characterization in a set of $\{T_1, \ldots, T_k\}$ phenotypic characterizations, a probability that a test biological specimen has the respective phenotypic characterization, the method comprising:

(A) learning a pairwise probability function $g_{pq}(X, W_{pq})$ using a training population, for a pair of phenotypic characterizations $(T_p, T_q)$ in the set of $\{T_1, \ldots, T_k\}$ phenotypic characterizations (i.e. assigning values to each of the weights in $W_{pq}$), wherein:

(i) there are at least five training samples in the training population for each phenotypic characterization in the set of $\{T_1, \ldots, T_k\}$ phenotypic characterizations;

(ii) Y is the set of all training samples in the training population that exhibits either phenotypic characterization $T_p$ or phenotypic characterization $T_q$, and each $Y_i$ in Y is the set of $\{y_{i1}, \ldots, y_{in}\}$ cellular constituent abundance values for a plurality of cellular constituents measured from a sample i, from the training population, which exhibits either phenotypic characterization $T_p$ or phenotypic characterization $T_q$;

(iii) $W_{pq}$ is a set of parameters derived from Y in the learning step (A) for a pair of phenotypic characterizations $(T_p, T_q)$ by substituting each $Y_i$ into $g_{pq}(X, W_{pq})$, as X, during said learning step (A);

(iv) k is 3 or greater;

(v) n is at least 1; and (vi) p is not equal to q;

(B) repeating the learning step (A) for a different pair of phenotypic characterizations $(T_p, T_q)$, using the training population, for all unique pairs of phenotypic characterizations in the set of $\{T_1, \ldots, T_k\}$ phenotypic characterizations, thereby deriving a plurality of pairwise probability functions $G=\{g_{1,2}(X, W_{1,2}), \ldots, g_{k-1,k}(X, W_{k-1,k})\}$;

(C) computing a plurality of pairwise probability values $P=\{p_{1,2}, \ldots, p_{k-1,k}\}$, wherein each pairwise probability value $p_{pq}$ in P is equal to $g_{pq}(Z, W_{pq})$ in G, the probability that the test biological specimen has phenotypic characterization $T_p$ and does not have phenotypic characterization $T_q$, wherein Z is a set of $\{z_1, \ldots, z_n\}$ cellular constituent abundance values measured from the test biological specimen for the plurality of cellular constituents;

(D) optionally converting P to a set M of k probabilities, where $M=\{p_1, p_2, \ldots, p_k\}$, wherein each probability $p_j$ in M is a probability for a phenotypic characterization in the set of $\{T_1, \ldots, T_k\}$ phenotypic characterizations that the biological specimen has the phenotypic charadcterization such that $$\sum_{j=1}^{k} p_j$$

is equal to a predetermined constant; and (E) optionally outputting one or more pairwise probabilities $p_{pq}$ in P to a user interface device, a monitor, a computer readable storage medium, or a local or remote computer system when step (D) is not performed; or displaying one or more pairwise probabilities $p_{pq}$ in P when step (D) is not performed, or optionally outputting one or more $p_j$ in M and/or one or more pairwise probabilities $p_{pq}$ in P to a user interface device, a monitor, a computer readable storage medium, or a local or remote computer system when step (D) is performed; or displaying one or more $p_j$ in M and/or one or more pairwise probabilities $p_{pq}$ in P when step (D) is performed. In some embodiments, there are at least 10, at least 20, at least 30, at least 40 or at least 50 training samples in the training population for each phenotypic characterization in the set of $\{T_1, \ldots, T_k\}$ phenotypic characterizations. In some embodiments, n is at least 1, n is at least 10, n is at least 100, or n is at least 1000.

Embodiment 102

The method of embodiment 101, wherein $$g_{pq}(Z, W_{pq}) = \sum_{R_i \in p} w'_i s(Z, R_i) - \sum_{R_j \in q} w''_j s(Z, R_j) + b$$

and wherein $R_i = \{r_{i1}, \ldots, r_{in}\}$ is the set of n cellular constituent abundance values for the plurality of cellular constituents measured from a sample i, from the training population, wherein sample i has phenotypic characterization $T_p$;

$R_j = \{r_{j1}, \ldots, r_{jn}\}$ is the set of n cellular constituent abundance values for the plurality of cellular constituents measured from a sample j, from the training population, wherein sample j has phenotypic characterization $T_q$;

$s(Z, R_i)$ is a score of a kernel function whose input is $(Z, R_i)$ where, for each respective cellular constituent abundance value $z_i$ in Z, the respective cellular constituent abundance value $z_i$ is matched to the corresponding cellular constituent abundance value $r_i$ in $R_i$;

$s(Z, R_j)$ is a score of a kernel function whose input is $(Z, R_j)$ where, for each respective cellular constituent abundance value $z_j$ in Z, the respective cellular constituent abundance value $z_j$ is matched to the corresponding cellular constituent abundance value $r_j$ in $R_j$;

b is a bias term;

$w'_i$ is a weight associated with $R_i$; and $w''_j$ is a weight associated with $R_j$.

Embodiment 103

The method of embodiment 102, wherein $s(Z, R_i)$ is equal to the value of the kernel function $e^{(-\gamma[(z_1-r_{i1})^2 + (z_2-r_{i2})^2 + \ldots (z_n-r_{in})^2])}$, wherein $z_1, \ldots, z_n$ are cellular constituent abundance values in Z that respectively correspond to cellular constituent abundance values $r_{i1}, \ldots, r_{in}$ in $R_i$; and wherein $s(Z, R_j)$ is equal to the value of the kernel function $e^{(-\gamma[(z_1-r_{j1})^2 + (z_2-r_{j2})^2 + \ldots (z_n-r_{jn})^2])}$, wherein $z_1, \ldots, z_n$ are cellular constituent abundance values in Z that respectively correspond to cellular constituent abundance values $r_{j1}, \ldots, r_{jn}$ in $R_j$.

Embodiment 104

The method of embodiment 102 or 103, the method further comprising determining values, for the given pair of phenotypic characterization $(T_p, T_q)$, for the set of weights $w'_i$s, $w''_j$, and b used in $g_{pq}(Z, W_{pq})$ before the computing step (C) by subjecting each set of cellular constituent abundance values in the training population that were measured from samples that have phenotypic characterization $T_p$ or $T_q$ to a support vector machine.

Embodiment 105

The method of any one of embodiments 102-104, wherein $$g_{pq}(Z, W_{pq}) = \frac{1}{1 + e^{Af(Z, W_{pq})+B}}$$

and wherein A and B are parameters derived from logistic regression of $s(Z, R_i)$ and the plurality of phenotypic characterizations.

Embodiment 106

The method of any one of embodiments 101-105, wherein a phenotypic characterization in the plurality of phenotypic characterizations is an organ type, an abnormal state in an organ, an tissue type, an abnormal state in a tissue, a cell type, an abnormal cell type, a cell morphology, an abnormal cell morphology, a disease state, a disease prognosis, or a therapeutic response.

Embodiment 107

The method of any one of embodiments 101-106, wherein the set of cellular constituent abundance values Z for the plurality of cellular constituents measured from the test biological specimen or the set of cellular constituent abundance values $Y_i$ for the plurality of cellular constituents measured from the sample i are measured from a microarray comprising probes arranged with a density of 100 different probes per 1 cm² or higher.

Embodiment 108

The method of any one of embodiments 101-107, wherein the set of cellular constituent abundance values Z for the plurality of cellular constituents measured from the test biological specimen or the set of cellular constituent abundance values $Y_i$ for the plurality of cellular constituents measured from the sample i are measured from a microarray comprising probes arranged with a density of at least 2,500 different probes per 1 cm².

Embodiment 109

The method of any one of embodiments 101-108, wherein the set of cellular constituent abundance values Z for the plurality of cellular constituents measured from the test biological specimen or the set of cellular constituent abundance values $Y_i$ for the plurality of cellular constituents measured from the sample i are measured from a microarray comprising at least 10,000 different probes.

Embodiment 110

The method of any one of embodiments 101-109, wherein the set of cellular constituent abundance values Z for the plurality of cellular constituents measured from the test biological specimen or the set of cellular constituent abundance values $Y_i$ for the plurality of cellular constituents measured from the sample i are measured from an expression microarray, a comparative genomic hybridization microarray, an exon microarray, or a microRNA microarray.

Embodiment 111

The method of any one of embodiments 101-110, wherein the set of cellular constituent abundance values Z for the plurality of cellular constituents measured from the test biological specimen or the set of cellular constituent abundance values $Y_i$ for the plurality of cellular constituents measured from the sample i are measured from a microarray comprising between 10 oligonucleotides and $5 \times 10^6$ oligonucleotides.

Embodiment 112

The method of any one of embodiments 101-111, wherein the plurality of cellular constituents is between 5 mRNA and 50,000 mRNA.

Embodiment 113

The method of any one of embodiments 101-112, wherein the plurality of cellular constituents is between 50 proteins and 200,000 proteins.

Embodiment 114

The method of any one of embodiments 101-113, wherein, for each respective phenotypic characterization in the plurality of phenotypic characterizations, the training population comprises at least three samples that have the respective phenotypic characterization.

Embodiment 115

The method of any one of embodiments 101-114, wherein eac phenotypic characterization in the plurality of phenotypic characterizations is a cancer tissue of origin and wherein the plurality of phenotypic characterizations comprises bladder cancer, breast cancer, colorectal cancer, gastric cancer, germ cell cancer, kidney cancer, hepatocellular cancer, non-small cell lung cancer, non-Hodgkin's lymphoma, melanoma, ovarian cancer, pancreatic cancer, prostate cancer, soft tissue sarcoma, and thyroid cancer.

Embodiment 116

The method of any one of embodiments 101-115, wherein the plurality of phenotypic characterizations is between 2 phenotypic characterizations and 100 phenotypic characterizations.

Embodiment 117

The method of any one of embodiments 101-116, wherein the set of cellular constituent abundance values Z are received from a remote source over a computer network and communicating the one or more pairwise probabilities $p_{pq}$ in P or the one or more $p_j$ in M to the remote source over said computer network.

Embodiment 118

The method of embodiment 117, wherein the remote source is a remote computer or a remote computer system.

Embodiment 119

The method of any one of embodiments 101-118, wherein the converting step (C) comprises deeming the set of probabilities $\{p_1, p_2, \ldots, p_k\}$ that minimize the criterion $f(p_1, p_2, \ldots, p_k)$ over $p_i$, where $f(\ )$ is defined as $$f(p_1, p_2, \ldots, p_k) = \sum_{i=1}^{k} \sum_{j=1, j \neq i}^{k} (p_i P_{T_i, T_j}(Z, W_{ij}) - p_j P_{T_j, T_i}(Z, W_{ji}))^2$$

subject to the constraints that $\Sigma_{i=1}^{k} p_i$=a predetermined constant and $p_i \geq 0$.

Embodiment 120

The method of any one of embodiments 101-119, wherein said learning of the pairwise probability function $g_{pq}(X, W_{pq})$ comprises using a decision tree, predictive analysis of microarrays, a multiple additive regression tree, a neural network, a clustering algorithm, principal component analysis, a nearest neighbor analysis, linear discriminant analysis, quadratic discriminant analysis, a support vector machine, an evolutionary method, a radial basis function, a projection pursuit, or weighted voting.

Embodiment 121

An apparatus for determining, for each respective phenotypic characterization in a set of of $\{T_1, \ldots, T_k\}$ phenotypic characterizations, a probability that a test biological specimen has the respective phenotypic characterization, the apparatus comprising:

a processor; and a memory, coupled to the processor, the memory storing a module comprising instructions for carrying out the method of any one of embodiments 101-120.

Embodiment 122

An apparatus for determining, for each respective phenotypic characterization in a set of $\{T_1, \ldots, T_k\}$ phenotypic characterizations, a probability that a test biological specimen has the respective phenotypic characterization, the apparatus comprising:

a processor; and a memory, coupled to the processor, the memory storing a module comprising:

(A) instructions for learning a pairwise probability function $g_{pq}(X, W_{pq})$ using a training population, for a pair of phenotypic characterizations $(T_p, T_q)$ in the set of $\{T_1, \ldots, T_k\}$ phenotypic characterizations, wherein:

(i) there are at least five training samples in the training population for each phenotypic characterization in the set of $\{T_1, \ldots, T_k\}$ phenotypic characterizations;

(ii) Y is the set of all training samples in the training population that exhibits either phenotypic characterization $T_p$ or phenotypic characterization $T_q$, and each $Y_i$ in Y is the set of $\{y_{i1}, \ldots, y_{in}\}$ cellular constituent abundance values for a plurality of cellular constituents measured from a sample i, from the training population, which exhibits either phenotypic characterization $T_p$ or phenotypic characterization $T_q$;

(iii) $W_{pq}$ is a set of parameters derived from Y by the instructions for learning (A) for a pair of phenotypic characterizations $(T_p, T_q)$ by substituting each $Y_i$ into $g_{pq}(X, W_{pq})$, as X, during said learning step (A);

(iv) k is 3 or greater;

(v) n is at least 1; and (vi) p is not equal to q;

(B) instructions for repeating the instructions for learning (A) for a different pair of phenotypic characterizations $(T_p, T_q)$, using the training population, for all unique pairs of phenotypic characterizations in the set of $\{T_1, \ldots, T_k\}$ phenotypic characterizations, thereby deriving a plurality of pairwise probability functions $G=\{g_{1,2}(X, W_{1,2}), \ldots, g_{k-1,k}(X, W_{k-1,k})\}$;

(C) instructions for computing a plurality of pairwise probability values $P=\{p_{1,2}, \ldots, p_{k-1,k}\}$, wherein each pairwise probability value $p_{pq}$ in P is equal to $g_{pq}(Z, W_{pq})$ in G, the probability that the test biological specimen has phenotypic characterization $T_p$ and does not have phenotypic characterization $T_q$, wherein Z is a set of $\{z_1, \ldots, z_n\}$ cellular constituent abundance values measured from the test biological specimen for the plurality of cellular constituents;

(D) optionally, instructions for converting P to a set M of k probabilities, where $M=\{p_1, p_2, \ldots, p_k\}$, wherein each probability $p_j$ in M is a probability for a phenotypic characterization in the set of $\{T_1, \ldots, T_k\}$ phenotypic characterizations that the biological specimen has the phenotypic characterization such that $$\sum_{j=1}^{k} p_j$$

is equal to a predetermined constant; and (E) optionally, instructions for outputting one or more pairwise probabilities $p_{pq}$ in P to a user interface device, a monitor, a computer readable storage medium, or a local or remote computer system when step (D) is not performed; or instructions for displaying one or more pairwise probabilities $p_{pq}$ in P when step (D) is not performed, or optionally, instructions for outputting one or more $p_j$ in M and/or one or more pairwise probabilities $p_{pq}$ in P to a user interface device, a monitor, a computer readable storage medium, or a local or remote computer system when step (D) is performed; or instructions for displaying one or more $p_j$ in M and/or one or more pairwise probabilities $p_{pq}$ in P when step (E) is performed.

Embodiment 123

The apparatus of embodiment 122, wherein the set of cellular constituent abundance values Z are received by the apparatus from a remote source over a network and wherein the one or more pairwise probabilities $p_{pq}$ in P or the one or more $p_j$ in M are communicated to the remote source over said network.

Embodiment 124

The apparatus of embodiment 122 or 123, wherein the memory further comprises Y and an indication of the phenotypic characterization of each sample i in the training population.

Embodiment 125

The apparatus of any one of embodiments 122-124, wherein the network is the Internet.

Embodiment 126

A computer-readable medium storing a computer program executable by a computer to determine, for each respective phenotypic characterization in a set of $\{T_1, \ldots, T_k\}$ phenotypic characterizations, a probability that a test biological specimen has the respective phenotypic characterization, the computer program comprising instructions for carrying out the method of any one of embodiments 101-120.

Embodiment 127

A computer-readable medium storing a computer program executable by a computer to determine, for each respective phenotypic characterization in a set of $\{T_1, \ldots, T_k\}$ phenotypic characterizations, a probability that a test biological specimen has the respective phenotypic characterization, the computer program comprising:

(A) instructions for learning a pairwise probability function $g_{pq}(X, W_{pq})$ using a training population, for a pair of phenotypic characterizations $(T_p, T_q)$ in the set of $\{T_1, \ldots, T_k\}$ phenotypic characterizations, wherein:

(i) there are at least five training samples in the training population for each phenotypic characterization in the set of $\{T_1, \ldots, T_k\}$ phenotypic characterizations;

(ii) Y is the set of all training samples in the training population that exhibits either phenotypic characterization $T_p$ or phenotypic characterization $T_q$, and each $Y_i$ in Y is the set of $\{y_{i1}, \ldots, y_{in}\}$ cellular constituent abundance values for a plurality of cellular constituents measured from a sample i, from the training population, which exhibits either phenotypic characterization $T_p$ or phenotypic characterization $T_q$;

(iii) $W_{pq}$ is a set of parameters derived from Y in the learning step (A) for a pair of phenotypic characterizations $(T_p, T_q)$ by substituting each $Y_i$ into $g_{pq}(X, W_{pq})$, as X, by the instructions for learning (A);

(iv) k is 3 or greater;

(v) n is at least 1; and (vi) p is not equal to q;

(B) instructions for repeating the instructions for learning (A) for a different pair of phenotypic characterizations $(T_p, T_q)$, using the training population, for all unique pairs of phenotypic characterizations in the set of $\{T_1, \ldots, T_k\}$ phenotypic characterizations, thereby deriving a plurality of pairwise probability functions $G=\{g_{1,2}(X, W_{1,2}), \ldots, g_{k-1, k}(X, W_{k-1, k})\}$;

(C) instructions for computing a plurality of pairwise probability values $P=\{p_{1,2}, \ldots, p_{k-1, k}\}$, wherein each pairwise probability value $p_{pq}$ in P is equal to $g_{pq}(Z, W_{pq})$ in G, the probability that the test biological specimen has phenotypic characterization $T_p$ and does not have phenotypic characterization $T_q$, wherein Z is a set of $\{z_1, \ldots, z_n\}$ cellular constituent abundance values measured from the test biological specimen for the plurality of cellular constituents;

(D) optionally, instructions for converting P to a set M of k probabilities, where $M=\{p_1, p_2, \ldots, p_k\}$, wherein each probability $p_j$ in M is a probability for a phenotypic characterization in the set of $\{T_1, \ldots, T_k\}$ phenotypic characterizations that the biological specimen has the phenotypic characterization such that $$\sum_{j=1}^{k} p_j$$

is equal to a predetermined constant; and (E) optionally, instructions for outputting one or more pairwise probabilities $p_{pq}$ in P to a user interface device, a monitor, a computer readable storage medium, or a local or remote computer system when step (D) is not performed; or instructions for displaying one or more pairwise probabilities $p_{pq}$ in P when step (D) is not performed, or optionally, instructions for outputting one or more $p_j$ in M and/or one or more pairwise probabilities $p_{pq}$ in P to a user interface device, a monitor, a computer readable storage medium, or a local or remote computer system when step (D) is performed; or instructions for displaying one or more $p_j$ in M and/or one or more pairwise probabilities $p_{pq}$ in P when step (E) is performed.

6 EXAMPLES

Tissue of unknown origin test. The tissue of origin test was designed for use on poorly differentiated, undifferentiated and metastatic tumor specimens after routine hematoxylin and eosin staining to aid in the diagnosis of the tissue of origin. The tissue of origin test compared the expression of selected genes to expression in tumors known to have one of the following tissues of origin: bladder, breast, colorectal, gastric, germ cell, hepatocellular, kidney, non-small cell lung, non-Hodgkin's lymphoma, melanoma, ovarian, pancreatic, prostate, soft tissue sarcoma, or thyroid. The test was performed using a microarray to obtain constituent abundance measurements of cellular constituents from frozen surgical specimens using microarrays.

Frozen biopsy specimens were processed by clinical laboratories per the recommended clinical laboratory protocol (RCLP). The processed RNA was hybridized to a microarray which was then scanned using an automated scanner. The resulting data file was processed in accordance with the instant invention and results were presented as an electronic report for clinical interpretation.

The report presented fifteen computed similarity scores, one for each tissue on the test panel in a graphical format. Each similarity score was a value between 0 and 100 that represented the probability that the specimen contained cellular material from the tissue indicated. In the present example, all similarity scores reported for a single specimen summed to 100.

The tissue of unknown origin test was developed through three phases: learning, validation and final model building. Each phase involved a corresponding data set: (i) the learning phase used a training dataset, (ii) the testing phase used an independent test dataset, and (iii) the module building used a combined dataset. The first two phases were performed repeatedly in order to choose a suitable test algorithm for the tissue of unknown origin (TOO) test. Once the best algorithm was identified, the model building phase was performed to optimize the parameters of the final model version. This model version was subsequently frozen prior to entering the clinical validation trial.

The tumor tissue specimens for the training, test and model building datasets were selected according to the six criteria set forth below:

1) Restrict specimens to morphologies in the following table set forth below. Carcinoid tumors and neuroendocrine tumors derived from any tissue were excluded.

Tissue of Origin Test: Included and Excluded Morphologies

| Tissue | Morphologies Included | Morphologies Excluded |
|---|---|---|
| Bladder | Adenocarcinoma | |
| | Transitional cell carcinoma | |
| Breast | Infiltrating ductal carcinoma | |
| | Infiltrating lobular carcinoma | |
| | Medullary carcinoma | |
| | Mucinous adenocarcinoma | |
| | Papillary adenocarcinoma | |
| Colorectal | Adenocarcinoma | |
| | Mucinous adenocarcinoma | |
| Gastric | Adenocarcinoma | Squamous cell carcinoma |
| | Signet ring cell carcinoma | |
| Germ Cell | Dysgerminoma | |
| | Embryonal carcinoma | |
| | Mixed germ cell tumor | |
| | Seminoma | |
| | Teratoma | |
| Kidney | Chromophobe carcinoma | Wilms' tumor |
| | Clear cell adenocarcinoma | Sarcomatoid renal cell carcinoma |
| | Papillary renal cell carcinoma | Urothelial (transitional cell) carcinoma |
| | Renal cell carcinoma | |

-continued

Tissue of Origin Test: Included and Excluded Morphologies

| Tissue | Morphologies Included | Morphologies Excluded |
|---|---|---|
| Hepatocellular | Hepatocellular carcinoma | Cholangiocarcinoma |
| | Hepatoblastoma | |
| Non-small cell Lung | Adenocarcinoma | Adenoid cystic carcinoma |
| | Adenosquamous carcinoma | Bronchioloalveolar carcinoma |
| | Papillary adenocarcinoma | Cylindroma |
| | Squamous cell carcinoma | Malignant mesothelioma |
| | Large cell carcinoma | Mucoepidermoid carcinoma |
| Non-Hodgkin's Lymphoma | Diffuse large B-cell lymphoma | |
| | Extranodal marginal zone B-cell lymphoma | |
| | Follicular lymphoma | |
| | Malignant lymphoma | |
| | Mantle cell lymphoma | |
| | Peripheral T-cell lymphoma | |
| Melanoma | Malignant melanoma | |
| Ovarian | Adenocarcinoma | Brenner tumor, malignant |
| | Carcinosarcoma/malignant mixed mullerian | Sex cord - stromal |
| | Clear cell adenocarcinoma | |
| | Cystadenocarcinoma | |
| | Endometroid adenocarcinoma | |
| | Papillary serous adenocarcinoma | |
| Pancreas | Acinar cell carcinoma | Malignant islet cell tumor |
| | Adenocarcinoma | |
| | Intraductal papillary carcinoma | |
| Prostate | Adenocarcinoma | |
| Soft Tissue Sarcoma | Angiosarcoma | |
| | Carcinosarcoma | |
| | Chondrosarcoma | |
| | Desmoplastic small round cell tumor | |
| | Ewing's sarcoma | |
| | Fibromyxosarcoma | |
| | Fibrosarcoma | |
| | Gastrointestinal stromal tumor | |
| | Leiomyosarcoma | |
| | Liposarcoma | |
| | Malignant Schwannoma | |
| | Osteosarcoma | |
| Thyroid | Follicular carcinoma | |
| | Hurthle cell carcinoma | |
| | Medullary carcinoma | |
| | Papillary carcinoma | |

2) Use specimens for which the phenotypic characterization was established unambiguously.

3) Maintain overall balance between training and test datasets.

4) For lower prevalence cancers (e.g., bladder, hepatocellular and pancreas), incorporate all available specimens.

5) For all cancers that are not low prevalence cancers, incorporate all metastatic specimens.

6) Use sufficient number of specimens to achieve reasonably narrow (95%) confidence intervals on the sensitivity of individual tests.

The tissue distribution for the tissue of unknown origin training, test, and model building datasets is given in the following table:

| Tissue | Symbol | Training | Test | Model Building |
|---|---|---|---|---|
| Bladder | BL | 30 | 30 | 62 |
| Breast | BR | 224 | 222 | 444 |

-continued

| Tissue | Symbol | Training | Test | Model Building |
|---|---|---|---|---|
| Colorectal | CO | 119 | 118 | 253 |
| Gastric | GA | 40 | 39 | 52 |
| Germ Cell | GC | 61 | 60 | 121 |
| Kidney | KI | 77 | 76 | 151 |
| Hepatocellular | LI | 22 | 23 | 41 |
| Non-small Cell Lung | LU | 109 | 108 | 221 |
| Non-Hodgkin's Lymphoma | LY | 49 | 48 | 97 |
| Melanoma | ME | 35 | 34 | 69 |
| Ovarian | OV | 85 | 81 | 189 |
| Pancreas | PA | 20 | 20 | 43 |
| Prostate | PR | 53 | 52 | 105 |
| Soft Tissue Sarcoma | SC | 65 | 63 | 122 |
| Thyroid | TH | 35 | 36 | 69 |
| Total | | 1024 | 1010 | 2039 |

The model building dataset was compiled by combining training and test datasets. As a result, the vast majority of training and test specimens were used for the final model building. However, the combined set also incorporated additional specimens acquired after the best algorithm was chosen, and it reflects additional cleanup of specimens not conforming to the finalized list of test morphologies given in the table above.

During the tissue of unknown origin development, various criteria of performance were utilized, depending on the specific algorithm used. In most instances, the overall error rate (e), and sensitivities of the individual tests i ($sens_i$), computed over the independent test set were given as:

$$e = \frac{FN}{N}$$

$$\text{Positive percent agreement} = sens_i = 100 * \frac{TP_i}{N_i}, 1 \leq i \leq 15$$

where FN (false negatives) was the total number of test set specimens misclassified by the algorithm, N=1010 the number of specimens in the test set, $TP_i$ (true positives) was the number of correctly classified specimens for each cancer type, and $N_i$ was the number of test specimens for each cancer type. The cancer types considered in the tissue of unknown origin test are given in the Table above.

Additionally, specificity (spec) and diagnostic odds ratios (DOR) were used during the test development and model building (the criteria were applied to each individual tissue of origin and, to simplify notation, the index i was omitted):

$$\text{Negative percent agreement} = spec = 100 * \left(1 - \left(\frac{TN}{FP+TN}\right)\right)$$

$$DOR = \frac{sens}{1-sens} \Big/ \frac{1-spec}{spec} = \frac{TP}{FN} \Big/ \frac{FP}{TN}$$

where TN, FP, TP, and FN are the number of true negative, false positive, true positive and false negative specimens, respectively, for the given tissue of origin.

The model that was developed using the 2039 samples in the model building dataset were applied to 477 specimens of known phenotypic classification (known tissue of origin) that were not included in the 2039 samples. The 2039 samples in the model building dataset and the 477 specimens of known phenotypic classification were all from human cancer patients. Of the 477 specimens, fifty percent were metastatic tumors and fifty percent were poorly differentiated primary tumors. Like the 2039 samples in the model building dataset, nucleic acid abundance data was collected from each of 477 samples from any of several different labs. Thus, microarray data for some of the 477 samples was obtained from lab 1, microarray data for some of the 477 samples was obtained in lab 2, and so forth until microarray data for each of the 477 samples was obtained.

The phenotypic characterization of each of the 477 specimens from among the fifteen possible phenotypic characterizations given in the table above was determined on a specimen by specimen basis. For each respective specimen in the 477 specimens, there was computed, for each respective pair of phenotypic characterizations ($T_p$, $T_q$) in phenotypic characterization pairs formed from the 15 phenotypic characterizations in the table above, a decision function having a pairwise probability function $g_{pq}(Z, W_{pq})$:

$$g_{pq}(Z, W_{pq}) = \sum_{R_i \in p} w'_i s(Z, R_i) - \sum_{R_j \in q} w''_j s(Z, R_j) + b$$

where, $R_i = \{r_{i1}, \ldots, r_{i1500}\}$ was the set of 1500 cellular constituent abundance values for the 1500 genes measured from a sample i, from the model building population (training population), where sample i has phenotypic characterization $T_p$ in the set of 15 different possible phenotypic characterizations;

$R_j = \{r_{j1}, \ldots, r_{j1500}\}$ was the set of 1550 cellular constituent abundance values for the 1500 genes measured from a sample j, from the model building population (training population), where sample j has phenotypic characterization $T_q$ in the set of 15 different possible phenotypic characterizations;

$Z = \{z_1, \ldots, z_{1500}\}$ was the set of 1500 cellular constituent abundance values for the 1500 genes measured from a specimen in the set of 477 specimens;

$s(Z, R_i)$ was a score of a kernel function whose input is (Z, $R_i$) where, for each respective cellular constituent abundance value $z_i$ in Z, the respective cellular constituent abundance value $z_i$ was matched to the corresponding cellular constituent abundance value $r_i$ in $R_i$;

$s(Z, R_j)$ was a score of a kernel function whose input is (Z, $R_j$) where, for each respective cellular constituent abundance value $z_j$ in Z, the respective cellular constituent abundance value $z_j$ was matched to the corresponding cellular constituent abundance value $r_j$ in $R_j$;

b is a bias term;

$w'_i$ was a weight associated with $R_i$; and $w''_j$ was a weight associated with $R_{jj}$.

Then, for each of the 477 test biological specimens, there was computed a respective pairwise probability $p_{pq}$ that the test biological specimen originated from phenotypic characterization $T_p$ using the pairwise probability function $g_{pq}(Z, W_{pq})$, thereby forming a plurality of pairwise probabilities $p_{pq}(Z)$. The plurality of pairwise probabilities $p_{pq}(Z)$ were converted to a set $M = \{p_1, \ldots, p_{15}\}$ probabilities, where each probability $p_j$ in the set of $\{p_1, \ldots, p_{15}\}$ probabilities was a probability for a phenotypic characterization in the corresponding set of $\{T_1, \ldots, T_{15}\}$ phenotypic characterizations such that $$\sum_{i=1}^{15} p_j$$

was equal to, in this study, 100. In this study, a sample having any probability $p_j$ in the set of $\{p_1, \ldots, p_{15}\}$ probabilities that was greater than or equal to 30 was deemed to have originated from the tissue corresponding to $p_j$ either as the tumor or the biopsy site. Thus, for example, if the score $p_j$ was greater than or equal to 30 and the corresponding tissue was bladder cancer, then the sample was deemed to be bladder, either as the tumor or the biopsy site. If two $p_j$ in the set of $\{p_1, \ldots, p_{15}\}$ probabilities were both greater than or equal to 30 for a given sample, and one of these $p_j$ indicated the biopsy site, then the other $p_j$ indicated the tumor with the probability described above. If two $p_j$ in the set of $\{p_1, \ldots, p_{15}\}$ probabilities were both greater than or equal to 30 for a given sample, but neither $p_j$ indicated the biopsy site, then the result was deemed indeterminate and no tissue of origin was indicated. If the maximum $p_j$ for a given sample was less than 30, then the result was deemed indeterminate and no tissue of origin was indicated. In the clinical validation study, a $p_j$ less than 5 allowed that tissue to be ruled out as a tissue of origin with a probability of greater than 95%. The results of the study are given in the following table, where "CI" stands for confidence interval.

The interpretation of the $p_j$ in the tissue of origin test report was aided by considering the clinical validation results in terms of conditional probabilities. Conditional probabilities illustrate the likelihood that a true positive tissue call was obtained when a $p_j$ of $\geq 30$ was reported (Table A), or that a true negative tissue call was obtained when a $p_j$ of <5 was reported (Table B). Probabilities for each of the 15 tissues in the tissue of origin test panel are given below in Tables A and B.

TABLE A

Probability that a $p_j \geq 30$ represents a true positive call for that tissue type in the specimen (includes biopsy site)

| Tissue Type | Probability | 95% CI |
|---|---|---|
| Bladder | 100.0 | [84.6, 100.0] |
| Breast | 90.1 | [80.7, 95.9] |
| Colorectal | 94.6 | [85.1, 98.9] |
| Gastric | 82.4 | [56.6, 96.2] |
| Germ Cell | 100.0 | [66.4, 100.0] |
| Hepatocellular | 100.0 | [79.4, 100.0] |
| Kidney | 97.4 | [86.5, 99.9] |
| Non-Hodgkin's Lymphoma | 100.0 | [89.4, 100.0] |
| Non-small Cell Lung | 94.1 | [80.3, 99.3] |
| Melanoma | 95.5 | [77.2, 99.9] |
| Ovarian | 100.0 | [94.6, 100.0] |
| Pancreas | 91.7 | [61.5, 99.8] |
| Prostate | 100.0 | [84.6, 100.0] |

| Phenotypic Characterization | Expected Positive | Expected Negative | Positive Percent Agreement (95% CI) | Negative Percent Agreement (95% CI) | Diagnostic Odds Ratios (95% CI) |
|---|---|---|---|---|---|
| Bladder | 28 | 449 | 78.6 [59.0, 91.7] | 100.0 [99.2, 100.0] | 3105.0 [162.1, 59461.8] |
| Breast | 68 | 409 | 94.1 [85.6, 98.4] | 98.3 [96.5, 99.3] | 916.6 [260.9, 3220.0] |
| Colorectal | 56 | 421 | 92.9 [82.7, 98.0] | 99.5 [98.3, 99.9] | 2717.0 [485.7, 15199.1] |
| Gastric | 17 | 460 | 82.4 [56.6, 96.2] | 99.3 [98.1, 99.9] | 709.3 [69.4, 7253.1] |
| Germ Cell | 12 | 465 | 75.0 [42.8, 94.5] | 100.0 [99.2, 100.0] | 2521.6 [96.4, 65981.6] |
| Hepatocellular | 17 | 460 | 88.2 [63.6, 98.5] | 99.8 [98.8, 100.0] | 1895.1 [74.2, 48411.4] |
| Kidney | 40 | 437 | 95.0 [83.1, 99.4] | 99.8 [98.7, 100.0] | 8265.0 [506.8, 134780.4] |
| Melanoma | 24 | 453 | 83.3 [62.6, 95.3] | 99.8 [98.8, 100.0] | 2255.0 [196.2, 25921.6] |
| Non-Hodgkin's Lymphoma | 33 | 444 | 93.8 [79.2, 99.2] | 99.5 [98.4, 99.9] | 3315.0 [292.2, 37610.1] |
| Non-small cell Lung | 31 | 446 | 87.1 [70.2, 96.4] | 98.9 [97.4, 99.6] | 594.0 [110.1, 3204.0] |
| Ovarian | 69 | 408 | 92.8 [83.9, 97.6] | 99.8 [98.6, 100.0] | 5196.8 [532.3, 50731.9] |
| Pancreas | 13 | 464 | 76.9 [46.2, 95.0] | 99.8 [98.8, 100.0] | 1540.0 [128.8, 18406.1] |
| Prostate | 25 | 452 | 88.0 [68.8, 97.5] | 100.0 [99.2, 100.0] | 5805.0 [230.0, 146535.3] |
| Soft-tissue Sarcoma | 31 | 446 | 83.9 [66.3, 94.5] | 99.3 [98.0, 99.9] | 766.1 [147.4, 3983.2] |
| Thyroid | 13 | 464 | 100.0 [75.3, 100.0] | 99.6 [98.4, 99.9] | 4984.2 [228.1, 108912.4] |
| Overall [95% CI] | 477 | | 89.5 [86.4, 92.1] | 99.6 [99.4, 99.7] | 1958.0 [1159.5, 3306.4] |

TABLE A-continued

Probability that a $p_j \geq 30$ represents a true positive call
for that tissue type in the specimen (includes biopsy site)

| Tissue Type | Probability | 95% CI |
|---|---|---|
| Soft Tissue Sarcoma | 86.7 | [69.3, 96.2] |
| Thyroid | 93.3 | [68.1, 99.8] |
| Overall | 95.9 | [93.6, 97.5] |

TABLE B

Probability that a $p_j < 5$ represents a true negative call
for that tissue type in the specimen

| Tissue Type | Probability | 95% CI |
|---|---|---|
| Bladder | 99.5 | [98.4, 99.9] |
| Breast | 99.4 | [98.0, 99.9] |
| Colorectal | 93.7 | [90.7, 96.0] |
| Gastric | 98.6 | [97.0, 99.5] |
| Germ Cell | 99.3 | [98.1, 99.9] |
| Hepatocellular | 96.4 | [94.2, 97.9] |
| Kidney | 99.7 | [98.6, 100.0] |
| Non-Hodgkin's Lymphoma | 91.1 | [87.9, 93.6] |
| Non-small Cell Lung | 97.0 | [94.6, 98.5] |
| Melanoma | 99.8 | [98.7, 100.0] |
| Ovarian | 99.7 | [98.2, 100.0] |
| Pancreas | 100.0 | [99.1, 100.0] |
| Prostate | 99.8 | [98.8, 100.0] |
| Soft Tissue Sarcoma | 98.1 | [96.3, 99.2] |
| Thyroid | 99.6 | [98.4, 99.9] |
| Overall | 98.1 | [97.8, 98.5] |

Overall accuracy across all fifteen tissues, using conditional probabilities and the recommended threshold for a positive call, was approximately 96%. Individual probabilities ranged from approximately 82% to greater than 99%. Additionally, overall accuracy across all 15 tissues, using conditional probabilities and the recommended threshold for a negative call, was approximately 98%. Individual probabilities ranged from approximately 91% to >99%.

An example of optionally outputting one or more $p_i$ in the set $\{1, \ldots, 15\}$ to a user interface device, a monitor, a computer readable storage medium, or a local or remote computer system or displaying one or more $p_i$ in the set $\{1, \ldots, 15\}$ is given in FIG. 3 where the $p_j$ for each of the 15 possible phenotypic characterizations is given for sample J06_0317P2A. The test illustrated in FIG. 3 shows that there is a 91.3 percent chance that the tissue of origin for the tumor is thyroid.

Reproducibility—concordance between laboratories. The reproducibility of the test was established in a study performed at four laboratories using 52 tumor specimens representative of those intended for use. Each tumor specimen was divided into equivalent aliquots. Each specimen received full processing at each laboratory, from tissue specimen to reported result. This study was designed to measure true clinical reproducibility by including key sources of expected variation such as variation across a single frozen tumor, variations in processing and protocols at different laboratories, multiple operators, and variations across the fifteen tissues types included on the test panel.

Reproducibility - concordance between laboratories

| Site | # Specimens, paired | % Concordance | % Discordance |
|---|---|---|---|
| Site 1 vs. Site 2 | 45 | 93.3 | 6.7 |
| Site 1 vs. Site 3 | 46 | 93.5 | 6.5 |
| Site 1 vs. Site 4* | 46 | 91.3 | 8.7 |
| Site 2 vs. Site 3 | 47 | 93.6 | 6.4 |
| Site 2 vs. Site 4* | 45 | 93.3 | 6.7 |
| Site 3 vs. Site 4* | 44 | 95.5 | 4.6 |
| Overall | 273 | 93.4 | 6.6 |

*One specimen originated from gastric was depleted.

The table set forth below shows performance (percent of correct identifications) of the tissue of origin test for tissue specimens that are "on-panel" (i.e., one of the fifteen tissues in the tissue of origin test panel) and the extent of cross-reactivity (TOO calls) for tissue specimens that are "off-panel" (i.e. not one of the fifteen tissues on the TOO Test panel). Off-panel tissue specimens originated from uterine cervix (n=42), endometrium (n=49), esophagus (n=28), small cell carcinoma of lung (n=4), and squamous cell carcinoma of the head and neck (Sq. H&N); n=18). Results for the 477 on-panel specimens and the 141 off-panel specimens are presented as percent of positive calls for specific tissues tests on the TOO panel. Cross-reactivity less than 5% is not reported.

TABLE 6

Pathwork Tissue of Origin Test: Cross-reactivity

| Bladder (BL) | | | |
|---|---|---|---|
| Tissue | n | BL (+) | % |
| Bladder | 28 | 22 | 78.6% |
| Cervix | 42 | 6 | 14.3% |
| Sq. Head & Neck | 18 | 2 | 11.1% |

| Breast (BR) | | | |
|---|---|---|---|
| Tissue | n | BR (+) | % |
| Breast | 68 | 64 | 94.1% |
| Cervix | 42 | 9 | 21.4% |
| Sq. Head & Neck | 18 | 2 | 11.1% |
| Pancreas | 13 | 1 | 7.7% |

| Colorectal (CO) | | | |
|---|---|---|---|
| Tissue | n | CO (+) | % |
| Colorectal | 56 | 52 | 92.9% |
| Cervix | 42 | 10 | 23.8% |
| Esophagus | 28 | 4 | 14.3% |

| Gastric (GA) | | | |
|---|---|---|---|
| Tissue | n | GA (+) | % |
| Gastric | 17 | 14 | 82.4% |
| Esophagus | 28 | 14 | 50.0% |
| Pancreas | 13 | 1 | 7.7% |

| Germ Cell (GC) | | | |
|---|---|---|---|
| Tissue | n | GC (+) | % |
| Germ Cell | 12 | 9 | 75.0% |

TABLE 6-continued

Pathwork Tissue of Origin Test: Cross-reactivity

Hepatocellular (LI)

| Tissue | n | LI (+) | % |
|---|---|---|---|
| Hepatocellular | 17 | 15 | 88.2% |

Kidney (KI)

| Tissue | n | KI (+) | % |
|---|---|---|---|
| Kidney | 40 | 38 | 95.0% |

Non-Hodgkin's Lymphoma (LY)

| Tissue | n | LY (+) | % |
|---|---|---|---|
| Non-Hodgkin's Lymphoma | 33 | 31 | 93.9% |

Non-small Cell Lung (LU)

| Tissue | n | LU (+) | % |
|---|---|---|---|
| Non-small Cell Lung | 31 | 27 | 87.1% |
| Small Cell Lung | 4 | 4 | 100.0% |
| Sq. Head & Neck | 18 | 6 | 33.3% |
| Cervix | 42 | 6 | 14.3% |
| Gastric | 17 | 1 | 5.9% |

Melanoma (ME)

| Tissue | n | ME (+) | % |
|---|---|---|---|
| Melanoma | 24 | 20 | 83.3% |

Ovarian (OV)

| Tissue | n | OV (+) | % |
|---|---|---|---|
| Ovarian | 69 | 64 | 92.8% |
| Endometrium | 49 | 43 | 87.8% |
| Cervix | 42 | 5 | 11.9% |

Pancreas (PA)

| Tissue | n | OV (+) | % |
|---|---|---|---|
| Pancreas | 13 | 10 | 76.9% |

Prostate (PR)

| Tissue | n | PR (+) | % |
|---|---|---|---|
| Prostate | 25 | 22 | 88.0% |

Soft Tissue Sarcoma (SC)

| Tissue | n | SC (+) | % |
|---|---|---|---|
| Soft Tissue Sarcoma | 31 | 26 | 83.9% |
| Germ Cell | 12 | 1 | 8.3% |

Thyroid (TH)

| Tissue | n | TH (+) | % |
|---|---|---|---|
| Thyroid | 13 | 13 | 100.0% |
| Sq. Head & Neck | 18 | 1 | 5.6% |

7 REFERENCES CITED

All references cited herein are incorporated herein by reference in their entirety and for all purposes to the same extent as if each individual publication or patent or patent application was specifically and individually indicated to be incorporated by reference in its entirety herein for all purposes.

8 MODIFICATIONS

Many modifications and variations of this invention can be made without departing from its spirit and scope, as will be apparent to those skilled in the art. The specific embodiments described herein are offered by way of example only, and the invention is to be limited only by the terms of the appended claims, along with the full scope of equivalents to which such claims are entitled.

What is claimed is:

1. A computer implemented method of determining, for each respective phenotypic characterization in a set of $\{T_1, \ldots, T_k\}$ phenotypic characterizations, a probability that a test biological specimen has the respective phenotypic characterization, the method comprising:

(A) learning a pairwise probability function $g_{pq}(X, W_{pq})$ using a training population, for a pair of phenotypic characterizations $(T_p, T_q)$ in the set of $\{T_1, \ldots, T_k\}$ phenotypic characterizations, wherein
  (i) there are at least five training samples in the training population for each phenotypic characterization in the set of $\{T_1, \ldots, T_k\}$ phenotypic characterizations;
  (ii) Y is the set of all training samples in the training population that exhibits either phenotypic characterization $T_p$ or phenotypic characterization $T_q$, and each $Y_i$ in Y is the set of $\{y_{i1}, \ldots, y_{in}\}$ cellular constituent abundance values for a plurality of cellular constituents measured from a sample i, from the training population, which exhibits either phenotypic characterization $T_p$ or phenotypic characterization $T_q$;
  (iii) $W_{pq}$ is a set of parameters derived from Y in the learning step (A) for a pair of phenotypic characterizations $(T_p, T_q)$ by substituting each $Y_i$ into $g_{pq}(X, W_{pq})$, as X, during said learning step (A);
  (iv) k is 3 or greater;
  (v) n is at least 1; and
  (vi) p is not equal to q;

(B) repeating the learning step (A) for a different pair of phenotypic characterizations $(T_p, T_q)$, using the training population, for all unique pairs of phenotypic characterizations in the set of $\{T_1, \ldots, T_k\}$ phenotypic characterizations, thereby deriving a plurality of pairwise probability functions $G=\{g_{1,2}(X, W_{1,2}), \ldots, g_{k-1, k}(X, W_{k-1, k})\}$;

(C) computing a plurality of pairwise probability values $P=\{p_{1,2}, \ldots, p_{k-1, k}\}$, wherein each pairwise probability value $p_{pq}$ in P is equal to $g_{pq}(Z, W_{pq})$ in G, the probability that the test biological specimen has phenotypic characterization $T_p$ and does not have phenotypic characterization $T_q$, wherein Z is a set of $\{z_1, \ldots, z_n\}$ cellular constituent abundance values measured from the test biological specimen for said plurality of cellular constituents;

(D) optionally converting P to a set M of k probabilities, wherein $M=\{p_1, p_2, \ldots, p_k\}$, wherein each probability $p_j$ in M is a probability for a phenotypic characterization in the set of $\{T_1, \ldots, T_k\}$ phenotypic characterizations that the test biological specimen has the phenotypic characterization such that $$\sum_{j=1}^{k} p_j$$

is equal to a predetermined constant; and (E) outputting one or more pairwise probabilities $p_{pq}$ in P to a user, a user interface device, a monitor, a computer readable storage medium, or a local or remote computer system when step (D) is not performed; or displaying one or more pairwise probabilities $p_{pq}$ in P when step (D) is not performed, or outputting one or more $p_j$ in M and/or one or more pairwise probabilities $p_{pq}$ in P to a user, a user interface device, a monitor, a computer readable storage medium, or a local or remote computer system when step (D) is performed; or displaying one or more $p_j$ in M and/or one or more pairwise probabilities $p_{pq}$ in P when step (D) is performed.

2. The computer implemented method of claim 1, wherein $$g_{pq}(Z, W_{pq}) = \sum_{R_i \in p} w'_i s(Z, R_i) - \sum_{R_j \in q} w''_j s(Z, R_j) + b$$

and wherein $R_i = \{r_{i1}, \ldots, r_{in}\}$ is the set of n cellular constituent abundance values for the plurality of cellular constituents measured from a sample i, from the training population, wherein sample i has phenotypic characterization $T_p$;

$R_j = \{r_{j1}, \ldots, r_{jn}\}$ is the set of n cellular constituent abundance values for the plurality of cellular constituents measured from a sample j, from the training population, wherein sample j has phenotypic characterization $T_q$;

$s(Z, R_i)$ is a score of a kernel function whose input is (Z, $R_i$) where, for each respective cellular constituent abundance value $z_i$ in Z, the respective cellular constituent abundance value $z_i$ is matched to the corresponding cellular constituent abundance value $r_i$ in $R_i$;

$s(Z, R_j)$ is a score of a kernel function whose input is (Z, $R_j$) where, for each respective cellular constituent abundance value $z_j$ in Z, the respective cellular constituent abundance value $z_j$ is matched to the corresponding cellular constituent abundance value $r_j$ in $R_j$;

b is a bias term;

$w'_i$ is a weight associated with $R_i$; and $w'_j$ is a weight associated with $R_j$.

3. The computer implemented method of claim 2, wherein $s(Z, R_i)$ is equal to the value of the kernel function $e^{(-\gamma[(z_1-r_{i1})^2+(z_2-r_{i2})^2+\ldots(z_n-r_{in})^2])}$, wherein $z_1, \ldots, z_n$ are cellular constituent abundance values in Z that respectively correspond to cellular constituent abundance values $r_{i1}, \ldots, r_{in}$ in $R_i$; and wherein $s(Z, R_j)$ is equal to the value of the kernel function $e^{(-\gamma[(z_1-r_{j1})^2+(z_2-r_{j2})^2+\ldots(z_n-r_{jn})^2])}$, where $z_1, \ldots, z_n$ are cellular constituent abundance values in Z that respectively correspond to cellular constituent abundance values $r_{j1}, \ldots, r_{jn}$ in $R_j$.

4. The computer implemented method of claim 2, the method further comprising determining values, for the given pair of phenotypic characterization $(T_p, T_q)$, for the set of weights $w'_i s$, $w''_j$, and b used in $g_{pq}(Z, W_{pq})$ before the computing step (C) by subjecting each set of cellular constituent abundance values in the training population that was measured from samples that have phenotypic characterization $T_p$ or $T_q$ to a support vector machine.

5. The computer implemented method of claim 2, wherein $$g_{pq}(Z, W_{pq}) = \frac{1}{1 + e^{Af(Z, W_{pq})+B}}$$

and wherein A and B are parameters derived from logistic regression of $s(Z, R_i)$ and the plurality of phenotypic characterizations.

6. The computer implemented method of claim 1, wherein a phenotypic characterization in the plurality of phenotypic characterizations is an organ type, an abnormal state in an organ, an tissue type, an abnormal state in a tissue, a cell type, an abnormal cell type, a cell morphology, an abnormal cell morphology, a disease state, a disease prognosis, or a therapeutic response.

7. The computer implemented method of claim 1, wherein the set of cellular constituent abundance values Z for the plurality of cellular constituents measured from the test biological specimen and the set of cellular constituent abundance values $Y_i$ for the plurality of cellular constituents measured from the sample i from the training population are measured from a microarray comprising probes arranged with a density of 100 different probes per 1 $cm^2$ or higher.

8. The computer implemented method of claim 1, wherein the set of cellular constituent abundance values Z for the plurality of cellular constituents measured from the test biological specimen and the set of cellular constituent abundance values $Y_i$ for the plurality of cellular constituents measured from the sample i from the training population are measured from a microarray comprising probes arranged with a density of at least 2,500 different probes per 1 $cm^2$.

9. The computer implemented method of claim 1, wherein the set of cellular constituent abundance values Z for the plurality of cellular constituents measured from the test biological specimen and the set of cellular constituent abundance values $Y_i$ for the plurality of cellular constituents measured from the sample i from the training population are measured from a microarray comprising at least 10,000 different probes.

10. The computer implemented method of claim 1, wherein the set of cellular constituent abundance values Z for the plurality of cellular constituents measured from the test biological specimen and the set of cellular constituent abundance values $Y_i$ for the plurality of cellular constituents measured from the sample i from the training population are measured from an expression microarray, a comparative genomic hybridization microarray, an exon microarray, or a microRNA microarray.

11. The computer implemented method of claim 1, wherein the set of cellular constituent abundance values Z for the plurality of cellular constituents measured from the test biological specimen and the set of cellular constituent abundance values $Y_i$ for the plurality of cellular constituents measured from the sample i from the training population are measured from a microarray comprising between 10 oligonucleotides and $5 \times 10^6$ oligonucleotides.

12. The computer implemented method of claim 1, wherein the plurality of cellular constituents is between 5 mRNAs and 50,000 mRNAs and the cellular constituent abundance values are amounts of each mRNA.

13. The computer implemented method of claim 1, wherein the plurality of cellular constituents is between 50 proteins and 200,000 proteins and the cellular constituent abundance values are amounts of each protein.

14. The computer implemented method of claim 1, wherein, for each respective phenotypic characterization in the plurality of phenotypic characterizations, the training population comprises at least three samples that have the respective phenotypic characterization.

15. The computer implemented method of claim 1, wherein each phenotypic characterization in the plurality of phenotypic characterizations is a cancer tissue of origin and wherein the plurality of phenotypic characterizations comprises bladder cancer, breast cancer, colorectal cancer, gastric cancer, germ cell cancer, kidney cancer, hepatocellular cancer, non-small cell lung cancer, non-Hodgkin's lymphoma, melanoma, ovarian cancer, pancreatic cancer, prostate cancer, soft tissue sarcoma, and thyroid cancer.

16. The computer implemented method of claim 1, wherein the plurality of phenotypic characterizations is between 2 phenotypic characterizations and 100 phenotypic characterizations.

17. The computer implemented method of claim 1, further comprising receiving the set of cellular constituent abundance values Z from a remote source over a computer network, and communicating the one or more pairwise probabilities $p_{pq}$ in P and/or the one or more $p_j$ in M to the remote source over said computer network.

18. The computer implemented method of claim 17, wherein the remote source is a remote computer or a remote computer system.

19. The computer implemented method of claim 1, wherein the converting step (C) comprises deeming the set of probabilities $\{p_1, p_2, \ldots, p_k\}$ that minimize the criterion $f(p_1, p_2, \ldots, p_k)$ over $p_i$, where $f(\ )$ is defined as $$f(p_1, p_2, \ldots, p_k) = \sum_{i=1}^{k} \sum_{j=1, j \neq i}^{k} \left( p_i P_{T_i, T_j}(Z, W_{ij}) - p_j P_{T_j, T_i}(Z, W_{ji}) \right)^2$$

subject to the constraints that $\Sigma^k_{i=1} p_i =$ a predetermined constant and $p_i \geq 0$.

20. The computer implemented method of claim 1, wherein said learning of the pairwise probability function $g_{pq}(X, W_{pq})$ comprises using a decision tree, predictive analysis of microarrays, a multiple additive regression tree, a neural network, a clustering algorithm, principal component analysis, a nearest neighbor analysis, a linear discriminant analysis, a quadratic discriminant analysis, a support vector machine, an evolutionary method, a projection pursuit, a radial basis function, or weighted voting.

21. An apparatus for determining, for each respective phenotypic characterization in a set of $\{T_1, \ldots, T_k\}$ phenotypic characterizations, a probability that a test biological specimen has the respective characterization, the apparatus comprising:
- a processor; and
- a memory, coupled to the processor, the memory storing a module comprising:
  - (A) instructions for learning a pairwise probability function $g_{pq}(X, W_{pq})$ using a training population, for a pair of phenotypic characterizations $(T_p, T_q)$ in the set of $\{T_1, \ldots, T_k\}$ phenotypic characterizations, wherein:
    - (i) there are at least five training samples in the training population for each phenotypic characterization in the set of $\{T_1, \ldots, T_k\}$ phenotypic characterizations;
    - (ii) Y is the set of all training samples in the training population that exhibits either phenotypic characterization $T_p$ or phenotypic characterization $T_q$, and each $Y_i$ in Y is the set of $\{y_{i1}, \ldots, y_{in}\}$ cellular constituent abundance values for a plurality of cellular constituents measured from a sample i, from the training population, which exhibits either phenotypic characterization $T_p$ or phenotypic characterization $T_q$;
    - (iii) $W_{pq}$ is a set of parameters derived from Y by the instructions for learning (A) for a pair of phenotypic characterizations $(T_p, T_q)$ by substituting each $Y_i$ into $g_{pq}(X, W_{pq})$, as X, during said learning step (A);
    - (iv) k is 3 or greater;
    - (v) n is at least 1; and
    - (vi) p is not equal to q,
  - (B) instructions for repeating the instructions for learning (A) for a different pair of phenotypic characterizations $(T_p, T_q)$, using the training population, for all unique pairs of phenotypic characterizations in the set of $\{T_1, \ldots, T_k\}$ phenotypic characterizations, thereby deriving a plurality of pairwise probability functions $G = \{g_{1,2}(X, W_{1,2}), \ldots, g_{k-1,k}(X, W_{k-1,k})\}$;
  - (C) instructions for computing a plurality of pairwise probability values $P = \{p_{1,2}, \ldots, p_{k-1,k}\}$, wherein each pairwise probability value $p_{pq}$ in P is equal to $g_{pq}(Z, W_{pq})$ in G, the probability that the test biological specimen has phenotypic characterization $T_p$ and does not have phenotypic characterization $T_q$, wherein Z is a set of $\{z_1, \ldots, z_n\}$ cellular constituent abundance values measured from the test biological specimen for said plurality of cellular constituents;
  - (D) optionally, instructions for converting P to a set M of k probabilities, wherein $M = \{p_1, p_2, \ldots, p_k\}$, wherein each probability $p_j$ in M is a probability for a phenotypic characterization in the set of $\{T_1, \ldots, T_k\}$ phenotypic characterizations that the biological specimen has the phenotypic characterization such that $$\sum_{j=1}^{k} p_j$$

is equal to a predetermined constant; and

- (E) instructions for outputting one or more pairwise probabilities $p_{pq}$ in P to a user, a user interface device, a monitor, a computer readable storage medium, or a local or remote computer system when step (D) is not performed; or instructions for displaying one or more pairwise probabilities $p_{pq}$ in P when step (D) is not performed, or
  - instructions for outputting one or more $p_j$ in M and/or one or more pairwise probabilities $p_{pq}$ in P to a user, a user interface device, a monitor, a computer readable storage medium, or a local or remote computer system when step (D) is performed; or instructions for displaying one or more $p_j$ in M and/or one or more pairwise probabilities $p_{pq}$ in P when step (D) is performed.

22. The apparatus of claim 21, said module further comprising instructions for:
- receiving the set of cellular constituent abundance values Z from a remote source over a computer network, and
- communicating the one or more pairwise probabilities $p_{pq}$ in P or the one or more $p_j$ in M to the remote source over said computer network.

23. The apparatus of claim 21, wherein the memory further comprises Y and an indication of the phenotypic characterization of each sample i in the training population.

24. The apparatus of claim 21, wherein the network is the Internet.

25. A computer-readable medium storing a computer program executable by a computer to determine, for each respective phenotypic characterization in a set of $\{T_1, \ldots, T_k\}$ phenotypic characterizations, a probability that a test biological specimen has the respective phenotypic characterization, the computer program comprising:

(A) instructions for learning a pairwise probability function $g_{pq}(X, W_{pq})$ using a training population, for a pair of phenotypic characterizations $(T_p, T_q)$ in the set of $\{T_1, \ldots, T_k\}$ phenotypic characterizations, wherein:
  (i) there are at least five training samples in the training population for each phenotypic characterization in the set of $\{T_1, \ldots, T_k\}$ phenotypic characterizations;
  (ii) Y is the set of all training samples in the training population that exhibits either phenotypic characterization $T_p$ or phenotypic characterization $T_q$, and each $Y_i$ in Y is the set of $\{y_{i1}, \ldots, y_{in}\}$ cellular constituent abundance values for a plurality of cellular constituents measured from a sample i, from the training population, which exhibits either phenotypic characterization $T_p$ or phenotypic characterization $T_q$;
  (iii) $W_{pq}$ is a set of parameters derived from Y in the learning step (A) for a pair of phenotypic characterizations $(T_p, T_q)$ by substituting each $Y_i$ into $g_{pq}(X, W_{pq})$, as X, by the instructions for learning (A);
  (iv) k is 3 or greater;
  (v) n is at least 1; and
  (vi) p is not equal to q, (B) instructions for repeating the instructions for learning (A) for a different pair of phenotypic characterizations $(T_p, T_q)$, using the training population, for all unique pairs of phenotypic characterizations in the set of $\{T_1, \ldots, T_k\}$ phenotypic characterizations, thereby deriving a plurality of pairwise probability functions $G=\{g_{1,2}(X, W_{1,2}), \ldots, g_{k-1, k}(X, W_{k-1, k})\}$;

(C) instructions for computing a plurality of pairwise probability values $P=\{p_{1,2}, \ldots, p_{k-1, k}\}$, wherein each pairwise probability value $p_{pq}$ in P is equal to $g_{pq}(Z, W_{pq})$ in G, the probability that the test biological specimen has phenotypic characterization $T_p$ and does not have phenotypic characterization $T_q$, wherein Z is a set of $\{z_1, \ldots, z_n\}$ cellular constituent abundance values measured from the test biological specimen for said plurality of cellular constituents;

(D) optionally, instructions for converting P to a set M of k probabilities, wherein $M=\{p_1, p_2, \ldots, p_k\}$, wherein each probability $p_j$ in M is a probability for a phenotypic characterization in the set of $\{T_1, \ldots, T_k\}$ phenotypic characterizations that the biological specimen has the phenotypic characterization such that $$\sum_{j=1}^{k} p_j$$

is equal to a predetermined constant;

(E) instructions for outputting one or more pairwise probabilities $p_{pq}$ in P to a user, a user interface device, a monitor, a computer readable storage medium, or a local or remote computer system when step (D) is not performed; or instructions for displaying one or more pairwise probabilities $p_{pq}$ in P when step (D) is not performed, or instructions for outputting one or more $p_j$ in M and/or one or more pairwise probabilities $p_{pq}$ in P to a user, a user interface device, a monitor, a computer readable storage medium, or a local or remote computer system when step (D) is performed; or instructions for displaying one or more $p_j$ in M and/or one or more pairwise probabilities $p_{pq}$ in P when step (D) is performed.

* * * * *